United States Patent [19]
Holton et al.

[11] Patent Number: 6,005,120
[45] Date of Patent: Dec. 21, 1999

[54] TRICYCLIC AND TETRACYCLIC TAXANES

[75] Inventors: Robert A. Holton, Tallahassee, Fla.; Carmen Somoza, Corvallis, Oreg.; Hyeong Baik Kim, Newark, Del.; Mitsuru Shindo, Tokyo, Japan; Ronald J. Biediger, Houston, Tex.; P. Douglas Boatman, Bellevue, Wash.; Chase Smith, Ada, Ohio; Feng Liang, Durham, N.C.; Krishna Murthi, Charlottesville, Va.

[73] Assignee: Florida State University, Tallahassee, Fla.

[21] Appl. No.: 08/778,173

[22] Filed: Jan. 2, 1997

Related U.S. Application Data

[63] Continuation-in-part of application No. PCT/US94/08350, Jul. 20, 1994, and a division of application No. 08/383,775, Feb. 6, 1995, Pat. No. 5,637,732, which is a division of application No. 08/189,058, Jan. 27, 1994, Pat. No. 5,405,972, which is a continuation-in-part of application No. 08/138,229, Oct. 15, 1993, abandoned, which is a continuation-in-part of application No. 08/095,161, Jul. 20, 1993, abandoned.

[51] Int. Cl.$^6$ .................. C07D 317/70; C07D 305/14
[52] U.S. Cl. .................. 549/229; 549/214; 549/432; 549/510; 549/511
[58] Field of Search .................. 549/214, 229, 549/432, 510, 511

[56] References Cited

U.S. PATENT DOCUMENTS

| | | | |
|---|---|---|---|
| Re. 34,277 | 6/1993 | Denis et al. | 549/510 |
| 4,814,470 | 3/1989 | Colin et al. | 514/449 |
| 4,857,653 | 8/1989 | Colin et al. | 549/511 |
| 4,876,399 | 10/1989 | Holton et al. | 568/817 |
| 4,924,011 | 5/1990 | Denis et al. | 549/510 |
| 4,924,012 | 5/1990 | Colin et al. | 549/510 |
| 5,015,744 | 5/1991 | Holton | 549/510 |
| 5,175,315 | 12/1992 | Holton | 549/510 |
| 5,229,526 | 7/1993 | Holton et al. | 549/213 |
| 5,248,796 | 9/1993 | Chen et al. | 549/510 |
| 5,254,703 | 10/1993 | Holton | 549/510 |
| 5,274,137 | 12/1993 | Nicolaou et al. | 549/510 |
| 5,290,957 | 3/1994 | Correa et al. | 549/510 |
| 5,292,921 | 3/1994 | Correa et al. | 560/29 |
| 5,416,225 | 5/1995 | Danishefsky et al. | 549/341 |
| 5,461,169 | 10/1995 | Nicolaou et al. | 549/510 |
| 5,481,007 | 1/1996 | Nicolaou et al. | 549/229 |
| 5,488,116 | 1/1996 | Danishefsky et al. | 549/214 |
| 5,508,447 | 4/1996 | Magnus | 509/354 |
| 5,527,924 | 6/1996 | Danishefsky et al. | 549/22 |
| 5,597,931 | 1/1997 | Danishefsky et al. | 549/214 |

OTHER PUBLICATIONS

Klein Synthesis of 9–Dihydrotaxol: A Novel Bioactive Taxol Tetrahedron Letters, vol. 34, No. 13 (1993) pp. 2047–2050.

Holton et al. "A Novel Lanthanide–Induced Rearrangement" Journal of Organic Chemistry, vol. 53 (1988) pp. 5981–5983.

Holton "Synthesis of the Taxane Ring System" Journal of American Chemical Society, vol. 106 (1984) p. 5731.

Holton et al., "Synthesis of Taxusin" Journal of American Chemical Society, vol. 110 (1988) p. 6558.

Hanessian et al. "A Practical Synthesis of 2–Deoxy Aldonolactones via a $SMI_2$–Mediated α–Deoxygenation Reaction" Tetrahedron Letters, vol. 33, No. 5 (1992) pp. 573–576.

Farina et al., "The Chemistry of Taxanes: Unexpected Rearrangement of Baccatin III During Chemoselective Debenzoylation with $Bu_3SnOMe/LiCl$" Tetrahedron Letters, vol. 33, No. 28 (1992) pp. 3979–3982.

Chen et al., "Taxol Structure–Activity Relationships: Synthesis and Biological Evaluation of 2–Deoxytaxol" Tetrahedron Letters, vol. 34, No. 20 (1993) pp. 3205–3206.

Chen et al., "Synthesis of 7–Deoxy–and 7,10–Dideoxytaxol via Radical Intermediates" Journal of Organic Chemistry, vol. 58 (1993) pp. 5028–5029.

Chaudhary et al. "Synthesis of 10–Deactoxytaxol and 10–Deoxytaxotere" Tetrahedron Letters, vol. 34, No. 31 (1993) pp. 4921–4924.

Samaranayake et al. "Modified Taxols. 5. Reaction of Taxol with Electrophilic Reagents and Preparation of a Rearranged Taxol Derivatives with Tubulin Assembly Activity" Journal of Organic Chemistry, vol. 56 (1991) pp. 5114–5119.

Borman "Total Synthesis of Anticancer Agent Taxol Achieved by Two Different Routes" C & EN (Feb. 21, 1994) pp. 32–34.

Kingston et al. "Progress in the Chemistry of Organic Natural Products 61", pp. 1–3 and 81–143, 1993.

Holton et al. "First Total Synthesis of Taxol. 1. Functionalization of the B Ring" Journal of American Chemical Soxiety, vol. 116 No. 4 (1994) pp. 1597–1598.

Holton et al. "First Total Synthesis of Taxol. 2. Completion of the C and D Rings" Journal of American Chemical Society, vol. 116, No. 4, (1994) pp. 1599–1600.

Nicolaou et al. "A Convergent Strategy Towards Taxol. A Facile Enantioselective entry Into a Fully Functionalized Ring A System" Journal of American Chemical Society, Chem. Commun., No. 16, (Aug. 1992) pp. 1117–1120.

G. Georg et al. "ACS Symposium Series 583—Taxane Anticancer Agents, Basic Science and Current Status" 207th National Meeting of the Am. Chem. Soc., San Diego, CA (Mar. 12–17, 1994).

*Primary Examiner*—Ba K. Trinh
*Attorney, Agent, or Firm*—Senniger, Powers, Leavitt & Roedel

[57] ABSTRACT

The synthesis of taxol and other tricyclic and tetracyclic taxanes.

16 Claims, No Drawings

TRICYCLIC AND TETRACYCLIC TAXANES

CROSS REFERENCE TO RELATED APPLICATIONS

This application is a divisional of application Ser. No. 08/383,775, filed Feb. 6, 1995, now U.S. Pat. No. 5,637,732 which is a divisional of application Ser. No. 08/189,058, filed Jan. 27, 1994, now U.S. Pat. No. 5,405,972 which is a continuation-in-part of application Ser. No. 08/138,229, filed Oct. 15, 1993 now abandoned, which is a continuation-in-part of application Ser. No. 08/095,161, filed Jul. 20, 1993 now abandoned. This application is also a continuation-in-part of PCT/US94/08350, filed Jul. 20, 1994.

This invention was made with Government support under NHI Grant #CA 42031 and NIH Grant #CA 55131 awarded by the National Institutes of Health. The Government has certain rights in the invention.

BACKGROUND OF THE INVENTION

The present invention is directed to the synthesis of taxol and other tricyclic and tetracyclic taxanes and novel intermediates thereof.

The taxane family of terpenes, of which taxol is a member, has attracted considerable interest in both the biological and chemical arts. Taxol is a promising cancer chemotherapeutic agent with a broad spectrum of antileukemic and tumor-inhibiting activity. Taxol has the following structure:

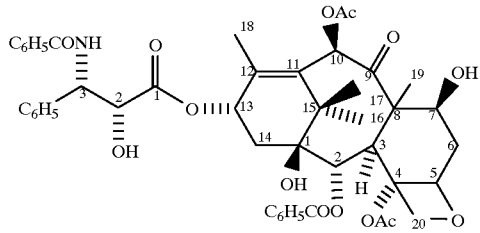

wherein Ac is acetyl.

The supply of taxol is presently being provided by the bark from *Taxus brevifollia* (Western Yew). However, taxol is found only in minute quantities in the bark of these slow growing evergreens. Consequently, chemists in recent years have expended their energies in trying to find a viable synthetic route for the preparation of taxol. To date, the results have not been entirely satisfactory.

A semi-synthetic approach to the preparation of taxol has been described by Greene, et al. in JACS 110, 5917 (1988), and involves the use of a congener of taxol, 10-deacetyl baccatin III which has the structure of formula II shown below:

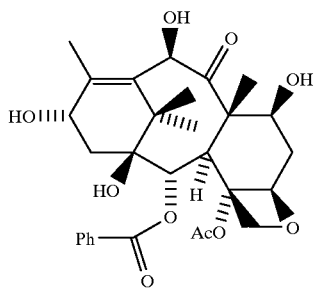

10-deacetyl baccatin III is more readily available than taxol since it can be obtained from the needles of *Taxus baccata*. According to the method of Greene et al., 10-deacetyl baccatin III ("10-DAB") is converted to taxol by attachment of the C-10 acetyl group and by attachment of the C-13 β-amido ester side chain through the esterification of the C-13 alcohol with a β-amido carboxylic acid unit.

Denis et al. in U.S. Pat. No. 4,924,011 disclose another process for preparing derivatives of baccatin III or of 10-deacetylbaccatin III of general formula

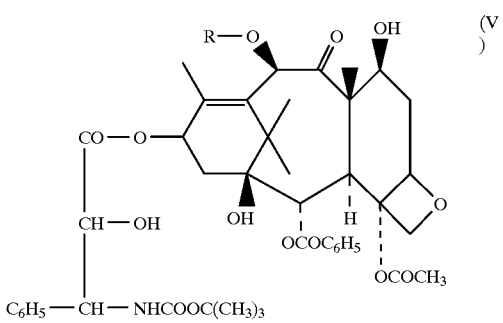

in which R' denotes hydrogen or acetyl. As reported, an acid of general formula:

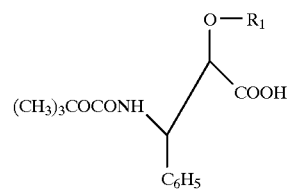

in which $R_1$ is a hydroxy-protecting group, is condensed with a taxane derivative of general formula:

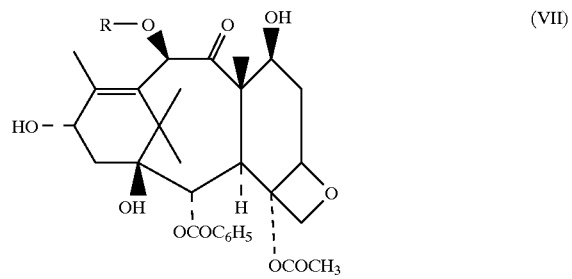

in which $R_2$ is an acetyl hydroxy-protecting group and $R_3$ is a hydroxy-protecting group, and the protecting groups $R_1$, $R_3$ and, where appropriate, $R_2$ are then replaced by hydrogen.

Other semisynthetic approaches for the preparation of taxol and for the preparation of other taxanes which possess tumor-inhibiting properties have been reported in recent years, but each of these approaches requires 10-DAB or baccatin III as a starting material. As such, the supply of taxol and other taxane derivatives remains dependent at least to some extent upon the collection of various parts of plants from the remote corners of the world and the extraction of 10-DAB and/or baccatin III therefrom.

SUMMARY OF THE INVENTION

Among the objects of the present invention, therefore, is the provision of a process for the synthesis of taxol and other tetracyclic taxanes; the provision of such a process which is highly diastereoselective; the provision of such a process which proceeds in relatively high yield; and the provision of key intermediates and processes for their preparation.

Briefly, therefore, the present invention is directed to a process for the preparation of taxol and other tricyclic and tetracyclic taxanes.

In accordance with one aspect of the present invention, the process comprises reacting a compound having the formula

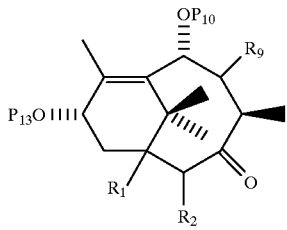

with BrMgN(iPr)$_2$, an aldehyde (or ketone), followed by phosgene and an alcohol to form a compound having the formula:

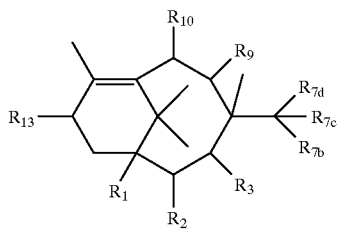

wherein
  $R_1$ is hydrogen or protected hydroxy; $R_2$ is hydrogen or protected hydroxy;
  $R_3$ is oxo;
  $R_{7b}$ is hydrogen, alkyl, cyano, hydroxy, protected hydroxy, or —OCOR$_{36}$;
  $R_{7c}$ and $R_{7d}$ are independently hydrogen, alkyl, alkenyl, alkynyl, aryl or heteroaryl;
  $R_9$ is hydrogen, protected hydroxy, or oxo;
  $R_{10}$ is —OP$_{10}$;
  $R_{13}$ is —OP$_{13}$;
  $R_{36}$ is hydrogen, alkyl, alkenyl, alkynyl, alkoxy, aryloxy, —NX$_8$X$_{10}$, —SX$_{10}$, monocyclic aryl or monocyclic heteroaryl;
  $X_8$ is hydrogen, alkyl, alkenyl, alkynyl, aryl, or heteroaryl;
  $X_{10}$ is alkyl, alkenyl, alkynyl, aryl, or heteroaryl; and
  $P_{10}$ and $P_{13}$ are hydroxy protecting groups.

In accordance with another aspect of the present invention, the process comprises reacting a compound having the formula

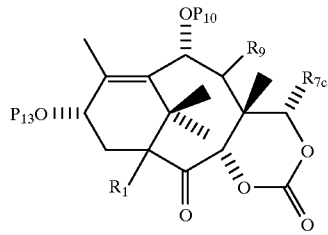

with lithium tetramethylpiperidide to form a compound having the formula:

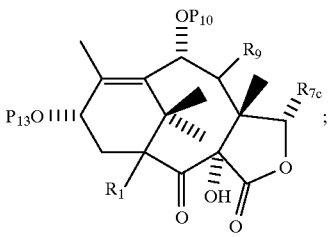

wherein
  $R_1$ is hydrogen or protected hydroxy;
  $R_{7c}$ is hydrogen, alkyl, alkenyl, alkynyl, aryl or heteroaryl;
  $R_9$ is hydrogen, protected hydroxy, or oxo; and
  $P_{10}$ and $P_{13}$ are hydroxy protecting groups.

In accordance with another aspect of the present invention, the process comprises reacting a compound having the formula:

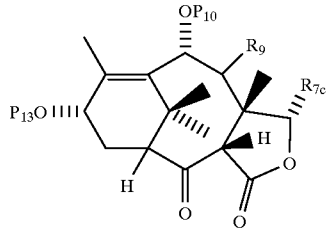

with lithium tetramethylpiperidide and camphosulfonyl oxaziridine to form a compound having the formula:

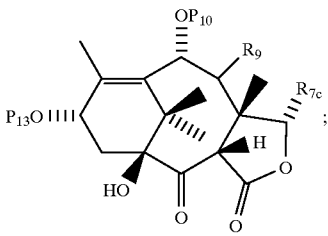

wherein $R_9$ is hydrogen, protected hydroxy, or oxo; $R_{7c}$ is hydrogen, alkyl, alkenyl, alkynyl, aryl or heteroaryl; and $P_{10}$ and $P_{13}$ are hydroxy protecting groups.

In accordance with another aspect of the present invention, the process comprises reacting a compound having the formula:

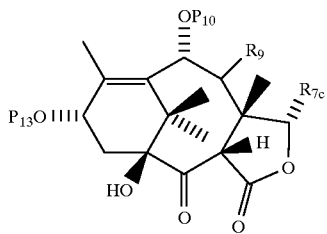

with a hydride reducing agent, preferably Red-Al, to form a compound having the formula:

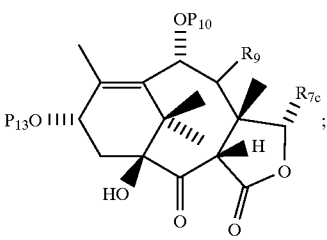

wherein $R_9$ is hydrogen, protected hydroxy, or oxo; $R_{7c}$ is hydrogen, alkyl, alkenyl, alkynyl, aryl or heteroaryl; and $P_{10}$ and $P_{13}$ are hydroxy protecting groups.

In accordance with another aspect of the present invention, the process comprises reacting a compound having the formula:

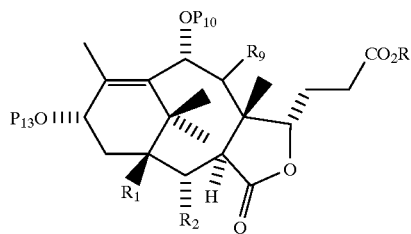

with lithium diisopropylamide to form a compound having the formula

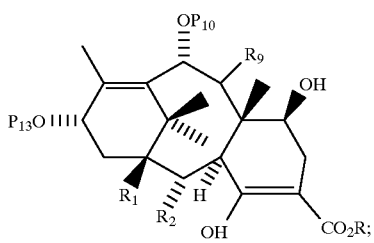

wherein R is lower alkyl, $R_1$ is hydrogen, protected hydroxy or $R_1$ and $R_2$ together form a carbonate, $R_2$ is hydrogen, protected hydroxy or $R_1$ and $R_2$ together form a carbonate, $R_9$ is hydrogen, protected hydroxy, or oxo; and $P_{10}$ and $P_{13}$ are hydroxy protecting groups.

In accordance with another aspect of the present invention, the process comprises reacting a compound having the formula:

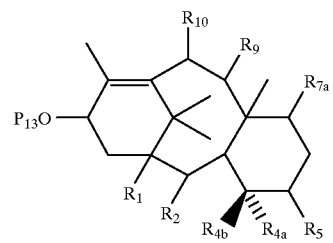

with DBU to form a compound having the formula:

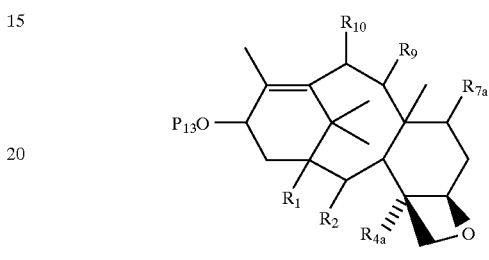

wherein
$R_1$ is hydrogen, hydroxy, protected hydroxy or —$OCOR_{30}$, or together with $R_2$ is a carbonate;

$R_2$ is hydrogen, hydroxy, protected hydroxy, oxo, or —$OCOR_{31}$, or together with $R_1$ is a carbonate;

$R_{4a}$ is hydrogen, alkyl, hydroxy, or protected hydroxy, or together with $R_2$ is a carbonate;

$R_{4b}$ is hydroxymethylene;

$R_5$ is —OMs, —OTs or a bromide;

$R_{7a}$ is hydrogen, protected hydroxy, or —$OCOR_{34}$, or together with $R_9$ is a carbonate;

$R_9$ is hydrogen, oxo, hydroxy, protected hydroxy, or —$OCOR_{33}$, or together with $R_{7a}$ or $R_{10}$ is a carbonate;

$R_{10}$ is hydrogen, oxo, hydroxy, protected hydroxy, or —$OCOR_{29}$, or together with $R_9$ is a carbonate;

$P_{13}$ is a hydroxy protecting group;

$R_{29}$, $R_{30}$, $R_{31}$, $R_{33}$ and $R_{34}$ are independently hydrogen, alkyl, alkenyl, alkynyl, alkoxy, aryloxy, —$NX_8X_{10}$, —$SX_{10}$, monocyclic aryl or monocyclic heteroaryl;

$X_8$ is hydrogen, alkyl, alkenyl, alkynyl, aryl, or heteroaryl; and $X_{10}$ is alkyl, alkenyl, alkynyl, aryl, or heteroaryl.

In accordance with another aspect of the present invention, the process comprises reacting a compound having the formula:

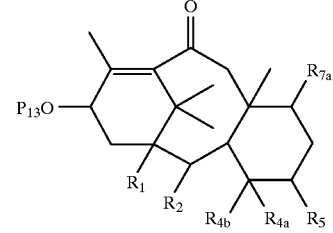

with KOtBu and $(PhSeO)_2O$ to form a compound having the formula:

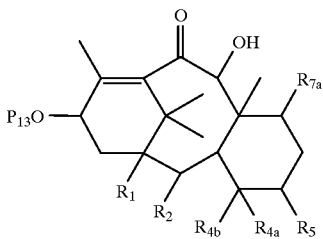

which rearranges in the presence of additional KOtBu, silica gel, or other acids or bases, or with heat to a compound having the formula:

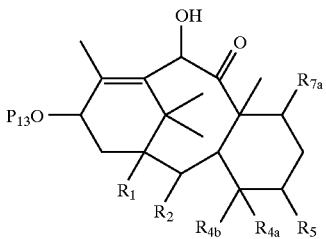

wherein $R_1$ is hydrogen, hydroxy, protected hydroxy, or —$OCOR_{30}$, or together with $R_2$ is a carbonate;

$R_2$ is hydrogen, protected hydroxy, or —$OCOR_{31}$, or together with $R_1$ or $R_{4a}$ is a carbonate;

$R_{4a}$ is hydrogen, alkyl, hydroxy, protected hydroxy, or —$OCOR_{27}$, together with $R_{4b}$ is an oxo, or together with $R_2$, $R_{4b}$, or $R_5$ is a carbonate;

$R_{4b}$ is hydrogen, alkyl, alkenyl, alkynyl, aryl, heteroaryl, or cyano, together with $R_{4a}$ is an oxo, together with $R_{4a}$ or $R_5$ is a carbonate, or together with $R_5$ and the carbons to which they are attached form an oxetane ring;

$R_5$ is hydrogen, protected hydroxy, —$OCOR_{37}$, together with $R_{4a}$ or $R_{4b}$ is a carbonate, or together with $R_{4b}$ and the carbons to which they are attached form an oxetane ring;

$R_{7a}$ is hydrogen, halogen, protected hydroxy, or —$OCOR_{34}$;

$P_{13}$ is a hydroxy protecting group;

$R_{27}$, $R_{30}$, $R_{31}$, $R_{34}$ and $R_{37}$ are independently hydrogen, alkyl, alkenyl, alkynyl, alkoxy, aryloxy, —$NX_8X_{10}$, —$SX_{10}$, monocyclic aryl or monocyclic heteroaryl;

$X_8$ is hydrogen, alkyl, alkenyl, alkynyl, aryl, heteroaryl, or heterosubstituted alkyl, alkenyl, alkynyl, aryl or heteroaryl; and $X_{10}$ is alkyl, alkenyl, alkynyl, aryl, heteroaryl, or heterosubstituted alkyl, alkenyl alkynyl, aryl or heteroaryl.

In general, the process of the present invention may be used to prepare taxanes having the formula:

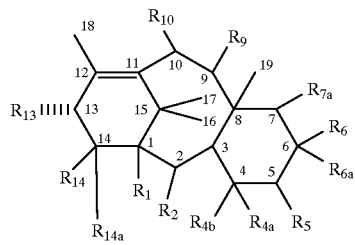

wherein $R_1$ is hydrogen, hydroxy, protected hydroxy, or —$OCOR_{30}$;

$R_2$ is hydrogen, hydroxy, —$OCOR_{31}$, or oxo;

$R_{4a}$ is hydrogen, alkyl, alkenyl, alkynyl, aryl, heteroaryl, cyano, hydroxy, —$OCOR_{27}$, or together with $R_{4b}$ forms an oxo, oxirane or methylene;

$R_{4b}$ is hydrogen, together with $R_{4a}$ forms an oxo, oxirane or methylene, or together with $R_5$ and the carbon atoms to which they are attached form an oxetane ring;

$R_5$ is hydrogen, halogen, hydroxy, protected hydroxy, —$OCOR_{37}$, oxo, or together with $R_{4b}$ and the carbon atoms to which they are attached form an oxetane ring;

$R_6$ is hydrogen, alkyl, alkenyl, alkynyl, aryl, or heteroaryl, hydroxy, protected hydroxy or together with $R_{6a}$ forms an oxo;

$R_{6a}$ is hydrogen, alkyl, alkenyl, alkynyl, aryl, or heteroaryl, hydroxy, protected hydroxy or together with $R_6$ forms an oxo;

$R_{7a}$ is hydrogen, halogen, hydroxy, protected hydroxy, —$OCOR_{34}$, oxo, or —$OR_{28}$;

$R_9$ is hydrogen, hydroxy, protected hydroxy, acyloxy, or oxo;

$R_{10}$ is hydrogen, —$OCOR_{29}$, hydroxy, protected hydroxy, or oxo;

$R_{13}$ is hydroxy, protected hydroxy, MO- or

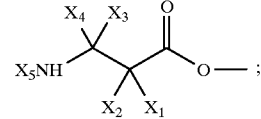

$R_{14}$ is hydrogen, alkyl, alkenyl, alkynyl, aryl, or heteroaryl;

$R_{14a}$ is hydrogen, alkyl, alkenyl, alkynyl, aryl, or heteroaryl, hydroxy, protected hydroxy or together with $R_1$ forms a carbonate;

$R_{28}$ is a functional group which increases the solubility of the taxane;

$R_{27}$, $R_{29}$, $R_{30}$, $R_{31}$, $R_{34}$ and $R_{37}$ are independently hydrogen, alkyl, alkenyl, alkynyl, monocyclic aryl or monocyclic heteroaryl;

$X_1$ is —$OX_6$, —$SX_7$, or —$NX_8X_9$;

$X_2$ is hydrogen, alkyl, alkenyl, alkynyl, aryl, or heteroaryl;

$X_3$ and $X_4$ are independently hydrogen, alkyl, alkenyl, alkynyl, aryl, or heteroaryl;

$X_5$ is —$COX_{10}$, —$COOX_{10}$, —$COSX_{10}$, —$CONX_8X_{10}$, or —$SO_2X_{11}$;

$X_6$ is hydrogen, alkyl, alkenyl, alkynyl, aryl, heteroaryl, hydroxy protecting group, or a functional group which increases the water solubility of the taxane derivative;

$X_7$ is alkyl, alkenyl, alkynyl, aryl, heteroaryl, or sulfhydryl protecting group;

$X_8$ is hydrogen, alkyl, alkenyl, alkynyl, aryl, heteroaryl, or heterosubstituted alkyl, alkenyl, alkynyl, aryl or heteroaryl;

$X_9$ is an amino protecting group;

$X_{10}$ is alkyl, alkenyl, alkynyl, aryl, heteroaryl, or heterosubstituted alkyl, alkenyl alkynyl, aryl or heteroaryl;

$X_{11}$ is alkyl, alkenyl, alkynyl, aryl, heteroaryl, —$OX_{10}$, or —$NX_8X_{14}$;

$X_{14}$ is hydrogen, alkyl, alkenyl, alkynyl, aryl, or heteroaryl; and

M comprises ammonium or is a metal.

The present invention is additionally directed to an intermediate for use in the preparation of a tricyclic or tetracyclic taxane having the formula:

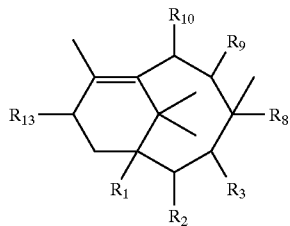

5 wherein $R_1$ is hydrogen, hydroxy, protected hydroxy or —$OCOR_{30}$, or together with $R_2$ is a carbonate;

$R_2$ is hydrogen, hydroxy, protected hydroxy, oxo, or —$OCOR_{31}$, or together with $R_1$ is a carbonate;

$R_3$ is hydrogen, hydroxy, protected hydroxy, —$OCOR_{32}$, or oxo;

$R_8$ is hydrogen, alkyl, alkenyl, alkynyl, aryl or heteroaryl;

$R_9$ is hydrogen, hydroxy, protected hydroxy, oxo, or —$OCOR_{33}$, or together with $R_{10}$ is a carbonate;

$R_{10}$ is hydrogen, hydroxy, protected hydroxy, oxo, or —$OCOR_{29}$, or together with $R_9$ is a carbonate;

$R_{13}$ is hydrogen, hydroxy, protected hydroxy, —$OCOR_{35}$ or MO-;

$R_{29}$, $R_{30}$, $R_{31}$, $R_{32}$, $R_{33}$, and $R_{35}$ are independently hydrogen, alkyl, alkenyl, alkynyl, alkoxy, aryloxy, —$NX_8X_{10}$, —$SX_{10}$, monocyclic aryl or monocyclic heteroaryl;

$X_8$ is hydrogen, alkyl, alkenyl, alkynyl, aryl, or heteroaryl;

$X_{10}$ is alkyl, alkenyl, alkynyl, aryl, or heteroaryl; and

M comprises ammonium or is a metal.

The present invention is further directed to an intermediate for use in the preparation of a tricyclic or tetracyclic taxane having the formula:

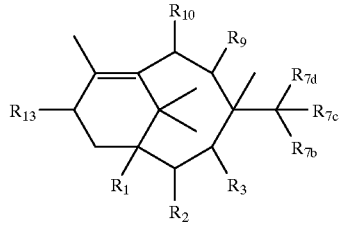

8 wherein $R_1$ is hydrogen, hydroxy, protected hydroxy or —$OCOR_{30}$, or together with $R_2$ is a carbonate;

$R_2$ is hydrogen, hydroxy, protected hydroxy, oxo, or —$OCOR_{31}$, or together with $R_1$ is a carbonate;

$R_3$ is hydrogen, hydroxy, protected hydroxy, —$OCOR_{32}$, or oxo, or together with $R_{7b}$ is a carbonate;

$R_{7b}$ is hydrogen, alkyl, cyano, hydroxy, protected hydroxy, or —$OCOR_{36}$, or together with $R_3$ or $R_9$ is a carbonate;

$R_{7c}$ and $R_{7d}$ are independently hydrogen, alkyl, alkenyl, alkynyl, aryl or heteroaryl;

$R_9$ is hydrogen, hydroxy, protected hydroxy, oxo, or —$OCOR_{33}$, or together with $R_{7b}$ or $R_{10}$ is a carbonate;

$R_{10}$ is hydrogen, hydroxy, protected hydroxy, oxo, or —$OCOR_{29}$, or together with $R_9$ is a carbonate;

$R_{13}$ is hydrogen, hydroxy, protected hydroxy, —$OCOR_{35}$ or MO-;

$R_{29}$, $R_{30}$, $R_{31}$, $R_{32}$, $R_{33}$, $R_{35}$ and R36 are independently hydrogen, alkyl, alkenyl, alkynyl, alkoxy, aryloxy, —$NX_8X_{10}$, —$SX_{10}$, monocyclic aryl or monocyclic heteroaryl;

$X_8$ is hydrogen, alkyl, alkenyl, alkynyl, aryl, or heteroaryl;

$X_{10}$ is alkyl, alkenyl, alkynyl, aryl, or heteroaryl; and

M comprises ammonium or is a metal.

The invention is further directed to an intermediate for use in the preparation of a tricyclic or tetracyclic taxane having the formula:

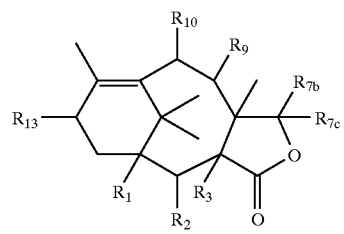

11 wherein $R_1$ is hydrogen, hydroxy, protected hydroxy or —$OCOR_{30}$, or together with $R_2$ is a carbonate;

$R_2$ is hydrogen, hydroxy, protected hydroxy, oxo, or —$OCOR_{31}$, or together with $R_1$ is a carbonate;

$R_3$ is hydrogen, hydroxy, protected hydroxy, or —$OCOR_{32}$;

$R_{7b}$ is hydrogen, alkyl, cyano, hydroxy, protected hydroxy, or —$OCOR_{36}$;

$R_{7c}$ is hydrogen, alkyl, alkenyl, alkynyl, aryl or heteroaryl;

$R_9$ is hydrogen, hydroxy, protected hydroxy, oxo, or —$OCOR_{33}$, or together with $R_{10}$ is a carbonate;

$R_{10}$ is hydrogen, hydroxy, protected hydroxy, oxo, or —$OCOR_{29}$, or together with $R_9$ is a carbonate;

$R_{13}$ is hydrogen, hydroxy, protected hydroxy, —$OCOR_{35}$ or MO-;

$R_{29}$, $R_{30}$, $R_{31}$, $R_{32}$, $R_{33}$, $R_{35}$ and $R_{36}$ are independently hydrogen, alkyl, alkenyl, alkynyl, alkoxy, aryloxy, —$NX_8X_{10}$, —$SX_{10}$, monocyclic aryl or monocyclic heteroaryl;

$X_8$ is hydrogen, alkyl, alkenyl, alkynyl, aryl, or heteroaryl;

$X_{10}$ is alkyl, alkenyl, alkynyl, aryl, or heteroaryl; and

M comprises ammonium or is a metal.

The present invention is further directed to an intermediate for use in the preparation of a tricyclic or tetracyclic taxane having the formula:

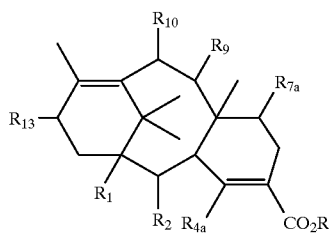

16 wherein
R is $C_1$–$C_8$ alkyl,
$R_1$ is hydrogen, hydroxy, protected hydroxy or —$OCOR_{30}$, or together with $R_2$ is a carbonate;
$R_2$ is hydrogen, hydroxy, protected hydroxy, oxo, or —$OCOR_{31}$, together with $R_1$ is a carbonate, or together with $R_4$ is a carbonate;
$R_{4a}$ is hydrogen, alkyl, hydroxy, protected hydroxy, or —$OCOR_{27}$, or together with $R_2$ is a carbonate;
$R_{7a}$ is hydrogen, halogen, hydroxy, protected hydroxy, —$OR_{28}$, —$OCOR_{34}$, or together with $R_9$ is a carbonate;
$R_9$ is hydrogen, oxo, hydroxy, protected hydroxy, —$OR_{28}$, or —$OCOR_{33}$, or together with $R_{7a}$ or $R_{10}$ is a carbonate;
$R_{10}$ is hydrogen, oxo, hydroxy, protected hydroxy, —$OR_{28}$, or —$OCOR_{29}$, or together with $R_9$ is a carbonate;
$R_{13}$ is hydrogen, hydroxy, protected hydroxy, 13 $OCOR_{35}$ or MO-;
$R_{28}$ is a functional group which increases the solubility of the taxane derivative;
$R_{27}$, $R_{29}$, $R_{30}$, $R_{31}$, $R_{33}$, $R_{34}$, and $R_{35}$ are independently hydrogen, alkyl, alkenyl, alkynyl, alkoxy, aryloxy, —$NX_8X_{10}$, —$SX_{10}$, monocyclic aryl or monocyclic heteroaryl;
$X_8$ is hydrogen, alkyl, alkenyl, alkynyl, aryl, or heteroaryl;
$X_{10}$ is alkyl, alkenyl, alkynyl, aryl, or heteroaryl; and
M comprises ammonium or is a metal.

The invention is further directed to an intermediate for use in the preparation of a tricyclic or tetracyclic taxane having the formula:

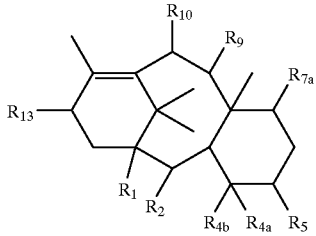

26a wherein
$R_1$ is hydrogen, hydroxy, protected hydroxy or —$OCOR_{30}$, or together with $R_2$ is a carbonate;
$R_2$ is hydrogen, hydroxy, protected hydroxy, oxo, or —$OCOR_{31}$, or together with $R_1$ or $R_{4a}$ is a carbonate;
$R_{4a}$ is hydrogen, alkyl, hydroxy, protected hydroxy, or —$OCOR_{27}$, together with $R_{4b}$ is an oxo, or together with $R_2$, $R_{4b}$, or $R_5$ is a carbonate;
$R_{4b}$ is hydrogen, alkyl, alkenyl, alkynyl, aryl, heteroaryl, or cyano, together with $R_{4a}$ is an oxo, together with $R_{4a}$ or $R_5$ is a carbonate, or together with $R_5$ and the carbons to which they are attached form an oxetane ring;
$R_5$ is hydrogen, hydroxy, protected hydroxy, —$OCOR_{37}$, oxo, together with $R_{4a}$ or $R_{4b}$ is a carbonate, or together with $R_{4b}$ and the carbons to which they are attached form an oxetane ring;

$R_{7a}$ is hydrogen, halogen, hydroxy, protected hydroxy, —$OR_{28}$, or —$OCOR_{34}$, or together with $R_9$ is a carbonate;
$R_9$ is hydrogen, oxo, hydroxy, protected hydroxy, —$OR_{28}$, or —$OCOR_{33}$, or together with $R_{7a}$ or $R_{10}$ is a carbonate;
$R_{10}$ is hydrogen, oxo, hydroxy, protected hydroxy, —$OR_{28}$, or —$OCOR_{29}$, or together with $R_9$ is a carbonate;
$R_{13}$ is hydrogen, hydroxy, protected hydroxy, —$OCOR_{35}$, MO- or

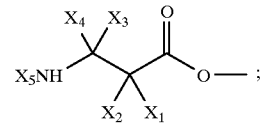

$R_{28}$ is a functional group which increases the solubility of the taxane derivative;
$R_{27}$, $R_{29}$, $R_{30}$, $R_{31}$, $R_{33}$, $R_{34}$, $R_{35}$ and $R_{37}$ are independently hydrogen, alkyl, alkenyl, alkynyl, alkoxy, aryloxy, —$NX_8X_{10}$, —$SX_{10}$, monocyclic aryl or monocyclic heteroaryl;
$X_1$ is —$OX_6$, —$SX_7$, or —$NX_8X_9$;
$X_2$ is hydrogen, alkyl, alkenyl, alkynyl, aryl, or heteroaryl;
$X_3$ and $X_4$ are independently hydrogen, alkyl, alkenyl, alkynyl, aryl, or heteroaryl;
$X_5$ is —$COX_{10}$, —$COOX_{10}$, —$COSX_{10}$, —$CONX_8X_{10}$, or —$SO_2X_{11}$;
$X_6$ is hydrogen, alkyl, alkenyl, alkynyl, aryl, heteroaryl, hydroxy protecting group, or a functional group which increases the water solubility of the taxane derivative;
$X_7$ is alkyl, alkenyl, alkynyl, aryl, heteroaryl, or sulfhydryl protecting group;
$X_8$ is hydrogen, alkyl, alkenyl, alkynyl, aryl, or heteroaryl;
$X_9$ is an amino protecting group;
$X_{10}$ is alkyl, alkenyl, alkynyl, aryl, or heteroaryl;
$X_{11}$ is alkyl, alkenyl, alkynyl, aryl, heteroaryl, —$OX_{10}$, or —$NX_8X_{14}$;
$X_{14}$ is hydrogen, alkyl, alkenyl, alkynyl, aryl, or heteroaryl; and
M comprises ammonium or is a metal The present invention is additionally directed to compounds having the formulae

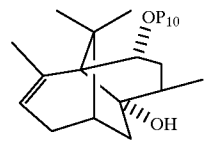

3

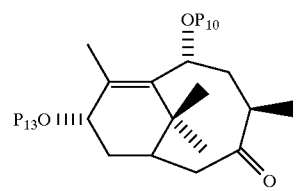

5

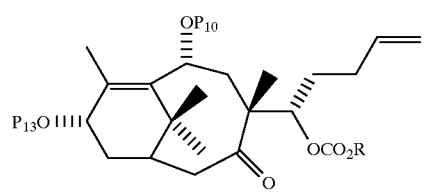
6
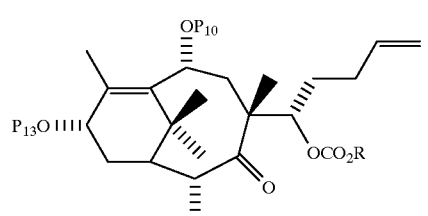
7
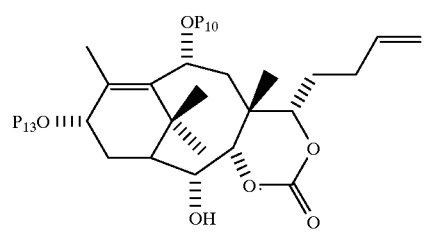
8
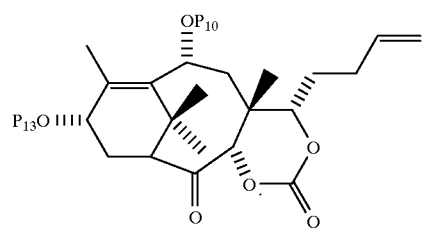
9
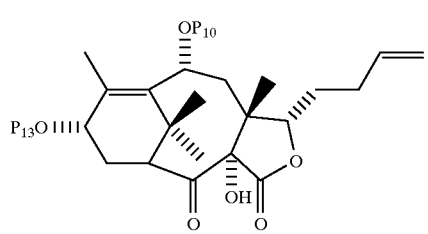
10
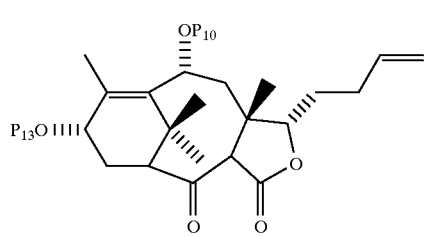
11
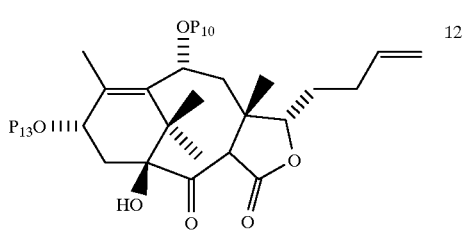
12
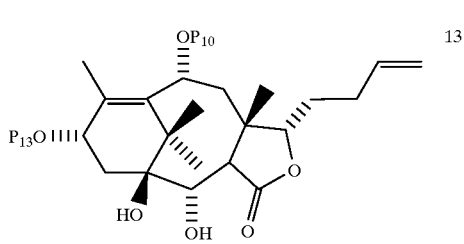
13
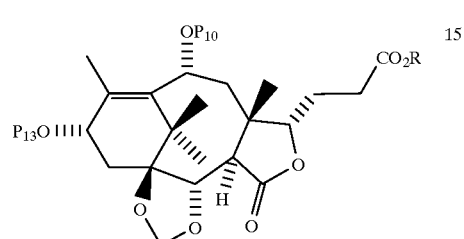
15
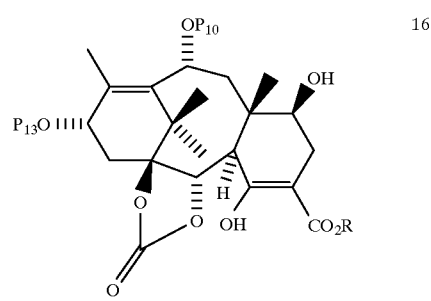
16
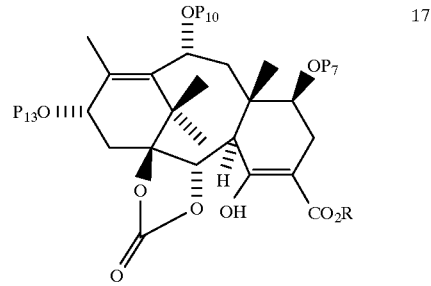
17

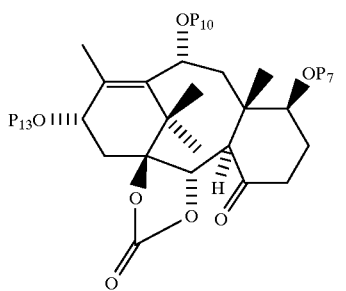

18

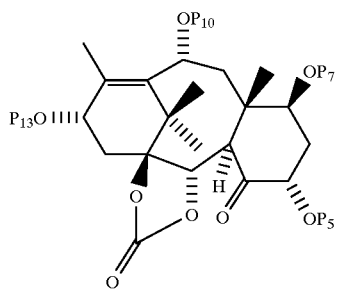

22a

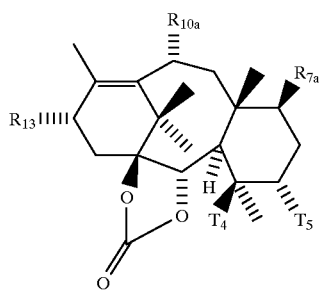

23a

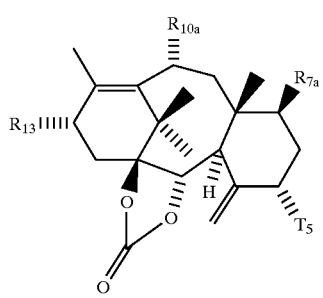

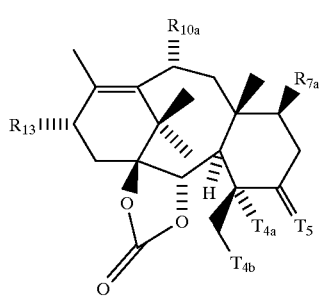

26a

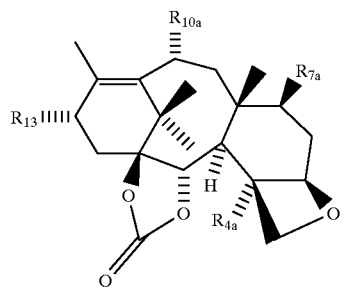

29

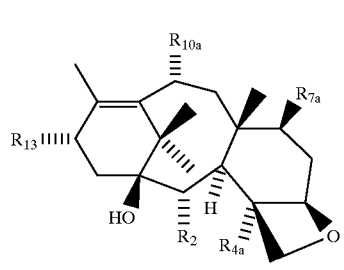

30

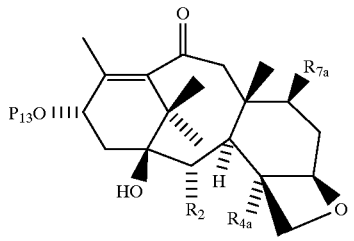

32 wherein
R is lower alkyl,
$T_4$ is hydroxy or protected hydroxy,
$T_{4a}$ and $T_{4b}$ are independently alkoxy, alkoxycarbonyloxy, acyloxy, sulfonyloxy, hydroxy, or protected hydroxy, or together form a carbonate,
$T_5$ is alkoxy, alkoxycarbonyloxy, acyloxy, sulfonyloxy, hydroxy, or protected hydroxy,
$P_5$, $P_7$, $P_{10}$ and $P_{13}$ are hydroxy protecting groups, and
$R_2$, $R_{4a}$, $R_{7a}$, $R_{10a}$, and $R_{13}$ are as previously defined.
These compounds are key intermediates in the synthesis of taxol and other taxanes. The present invention is also directed to processes for the preparation of these key intermediates.

Other objects and features of this invention will be in part apparent and in part pointed out hereinafter.

DETAILED DESCRIPTION OF THE PREFERRED EMBODIMENTS

As used herein "Ar" means aryl; "Ph" means phenyl; "Me" means methyl; "Et" means ethyl; "iPr" means isopropyl; "tBu" and "t-Bu" means tert-butyl; "R" means lower alkyl unless otherwise defined; "Ac" means acetyl; "py" means pyridine; "TES" means triethylsilyl; "TMS" means trimethylsilyl; "TBS" means $Me_2$t-BuSi-; "Tf" means $—SO_2CF_3$; "BMDA" means $BrMgNiPr_2$; "Swern" means $(COCl)_2$, $Et_3N$; "LTMP" means lithium tetramethylpiperidide; "MOP" means 2-methoxy-2-propyl; "BOM" means benzyloxymethyl; "LDA" means lithium diisopropylamide; "LAH" means lithium aluminum hydride; "Red-Al" means sodium bis(2-methoxyethoxy) aluminum hydride; "Ms" means $CH_3SO_2$-; "TASF" means tris(diethylamino) sulfonium-difluorotrimethylsilicate; "Ts" means toluenesulfonyl; "TBAF" means tetrabutyl ammonium fluoride; "TPAP" means tetrapropylammonium perruthenate; "DBU" means diazabicycloundecane; "DMAP" means p-dimethylamino pyridine; "LHMDS" means lithium hexamethyldisilazide; "DMF", means dimethylformamide; "AIBN" means azo-(bis)-isobutyronitrile; "10-DAB" means 10-desacetylbaccatin III; "FAR" means 2-chloro-1,1,2-trifluorotriethylamine; "mCPBA" means metachloroperbenzoic acid; "DDQ" means dicyanodichloroquinone; "sulfhydryl protecting group" includes, but is not limited to, hemithioacetals such as 1-ethoxyethyl and methoxymethyl, thioesters, or thiocarbonates; "amine protecting group" includes, but is not limited to, carbamates, for example, 2,2,2-trichloroethylcarbamate or tertbutylcarbamate; "protected hydroxyl" means -OP wherein P is a hydroxy protecting group; and "hydroxy protecting group" includes, but is not limited to, acetals having two to ten carbons, ketals having two to ten carbons, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloroethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other hydroxyl, sulfhydryl and amine protecting groups may be found in "Protective Groups in Organic Synthesis" by T. W. Greene, John Wiley and Sons, 1981.

The alkyl groups described herein are preferably lower alkyl containing from one to six carbon atoms in the principal chain and up to 15 carbon atoms. They may be straight or branched chain and include methyl, ethyl, propyl, isopropyl, butyl, hexyl and the like. They may be hydrocarbon or heterosubstituted with the various substituents defined herein, including heteroalkyl, alkenyl, heteroalkenyl, alkynyl, heteroalkynyl, aryl, heteroaryl, and heterosubstituted heteroaryl.

The alkenyl groups described herein are preferably lower alkenyl containing from two to six carbon atoms in the principal chain and up to 15 carbon atoms. They may be straight or branched chain and include ethenyl, propenyl, isopropenyl, butenyl, isobutenyl, hexenyl, and the like. They may be hydrocarbon or heterosubstituted with the various substituents defined herein, including alkyl, heteroalkyl, heteroalkenyl, alkynyl, heteroalkynyl, aryl, heteroaryl, and heterosubstituted heteroaryl.

The alkynyl groups described herein are preferably lower alkynyl containing from two to six carbon atoms in the principal chain and up to 15 carbon atoms. They may be straight or branched chain and include ethynyl, propynyl, butynyl, isobutynyl, hexynyl, and the like. They may be hydrocarbon or heterosubstituted with the various substituents defined herein, including alkyl, heteroalkyl, alkenyl, heteroalkenyl, heteroalkynyl, aryl, heteroaryl, and heterosubstituted heteroaryl.

The aryl moieties described herein contain from 6 to 15 carbon atoms and include phenyl. They may be hydrocarbon or heterosubstituted with the various substituents defined herein, including alkyl, heteroalkyl, alkenyl, heteroalkenyl, alkynyl, heteroalkynyl, heteroaryl, and heterosubstituted heteroaryl. Phenyl is the more preferred aryl.

The heteroaryl moieties described herein contain from 5 to 15 atoms and include, furyl, thienyl, pyridyl and the like. They may be hydrocarbon or heterosubstituted with the various substituents defined herein, including alkyl, heteroalkyl, alkenyl, heteroalkenyl, alkynyl, heteroalkynyl, aryl, and heterosubstituted heteroaryl.

The acyl moieties described herein contain alkyl, alkenyl, alkynyl, aryl or heteroaryl groups.

The alkoxycarbonyloxy moieties described herein comprise lower alkyl, alkenyl, alkynyl or aryl groups.

The hydrocarbon substituents described herein may be alkyl, alkenyl, alkynyl, or aryl, and the heterosubstituents of the heterosubstituted alkyl, alkenyl, alkynyl, aryl, and heteroaryl moieties described herein contain nitrogen, oxygen, sulfur, halogens and/or one to six carbons, and include lower alkoxy such as methoxy, ethoxy, butoxy, halogen such as chloro or fluoro, and nitro, heteroaryl such as furyl or thienyl, alkanoxy, hydroxy, protected hydroxy, acyl, acyloxy, nitro, amino, and amido.

An exemplary synthesis of baccatin III or 10-DAB is depicted hereinbelow in Reaction Scheme A. The starting material, diol 2, can be prepared from patchino (commonly known as B-patchouline epoxide) which is commercially available. The patchino is first reacted with an organometallic, such as lithium t-butyl followed by oxidation with an organic peroxide, such as t-butylperoxide in the presence of titanium tetraisopropoxide to form a tertiary alcohol. The tertiary alcohol is then reacted with a Lewis acid, such as boron trifluoride at low temperature, in the range from 40° C. to −100° C.; in the presence of an acid, such as trifluoromethane sulfonic acid. A graphical depiction of this reaction scheme along with an experimental write-up for the preparation of diol 2 can be found in U.S. Pat. No. 4,876,399.

Reaction Scheme A
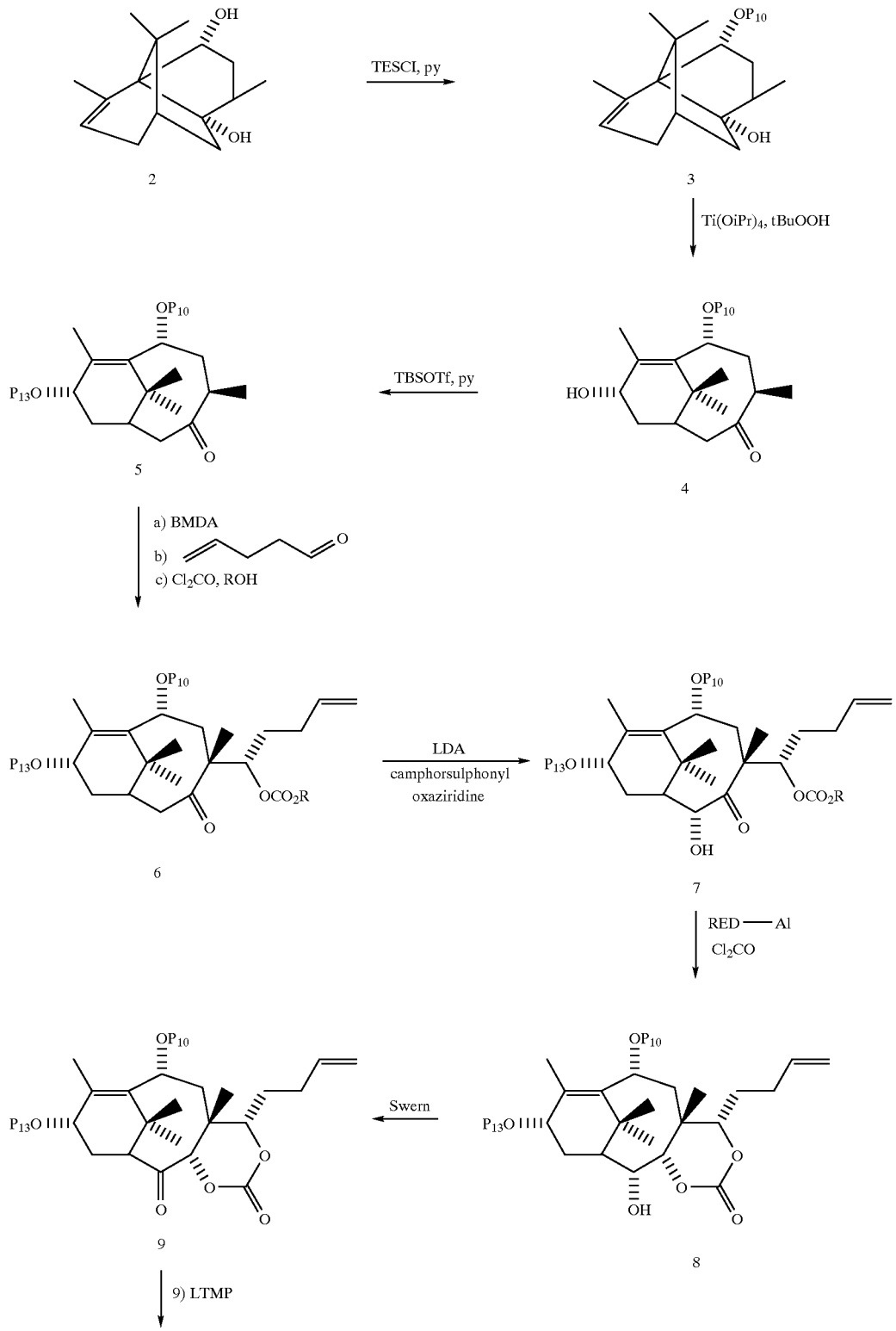

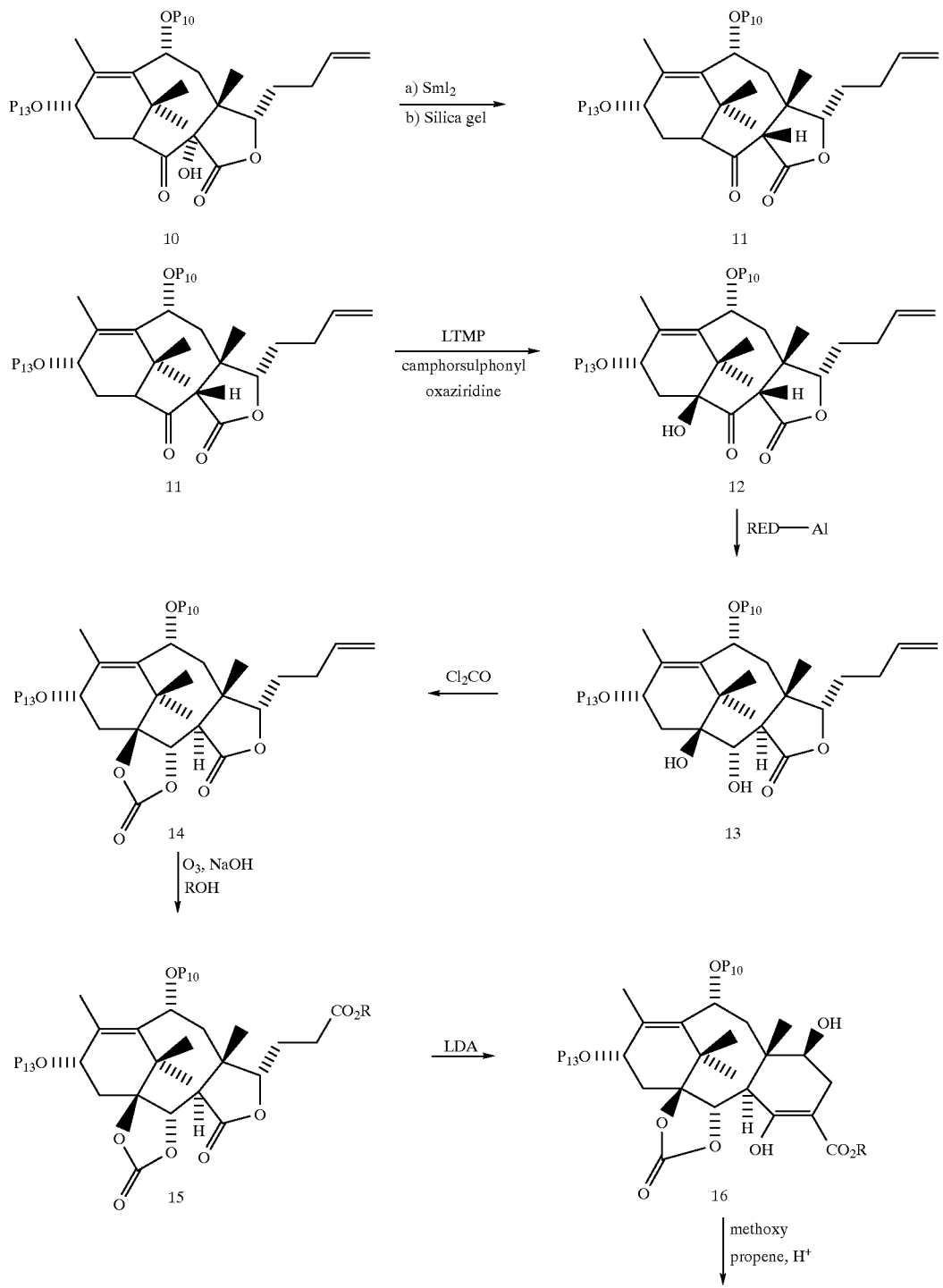

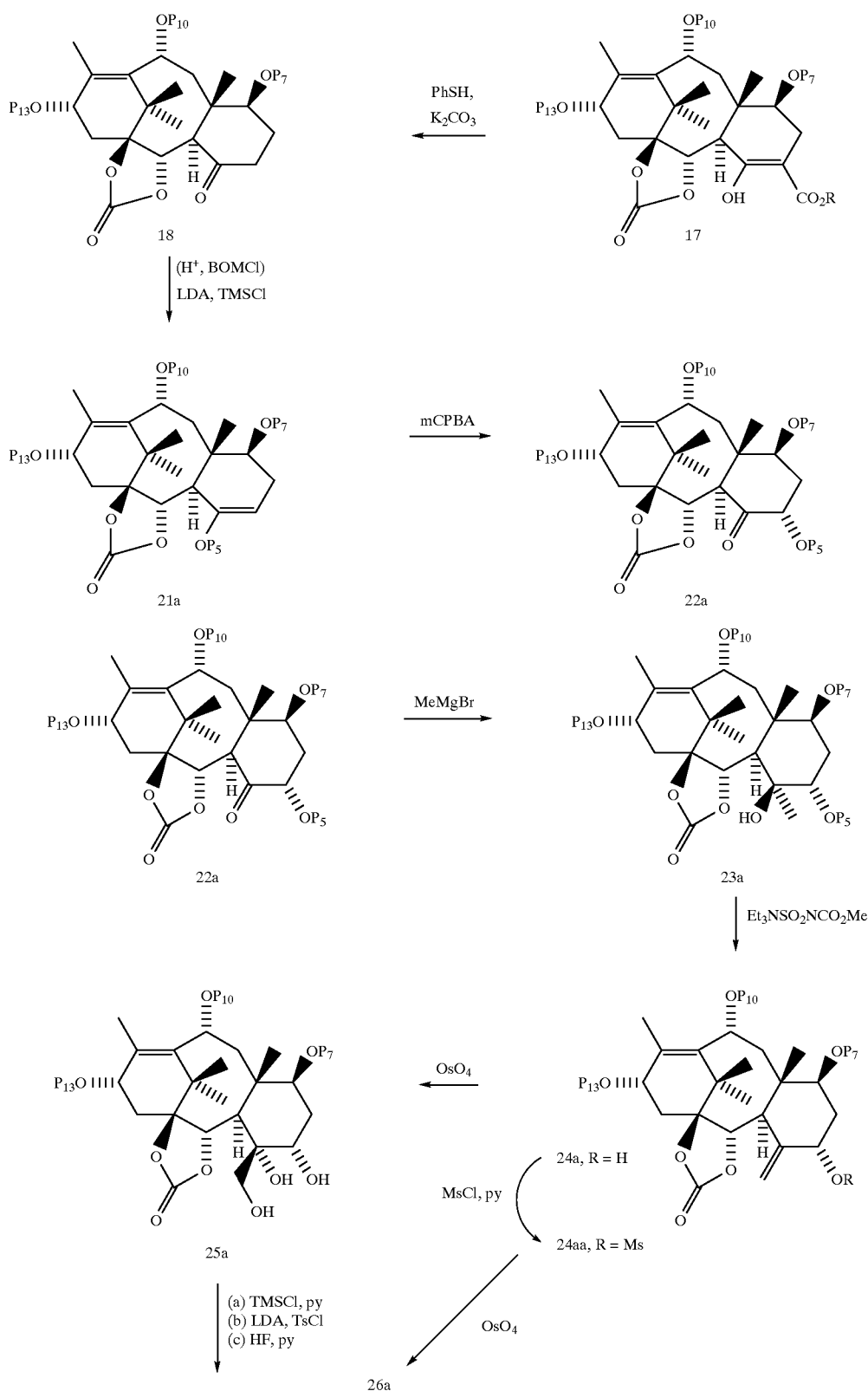

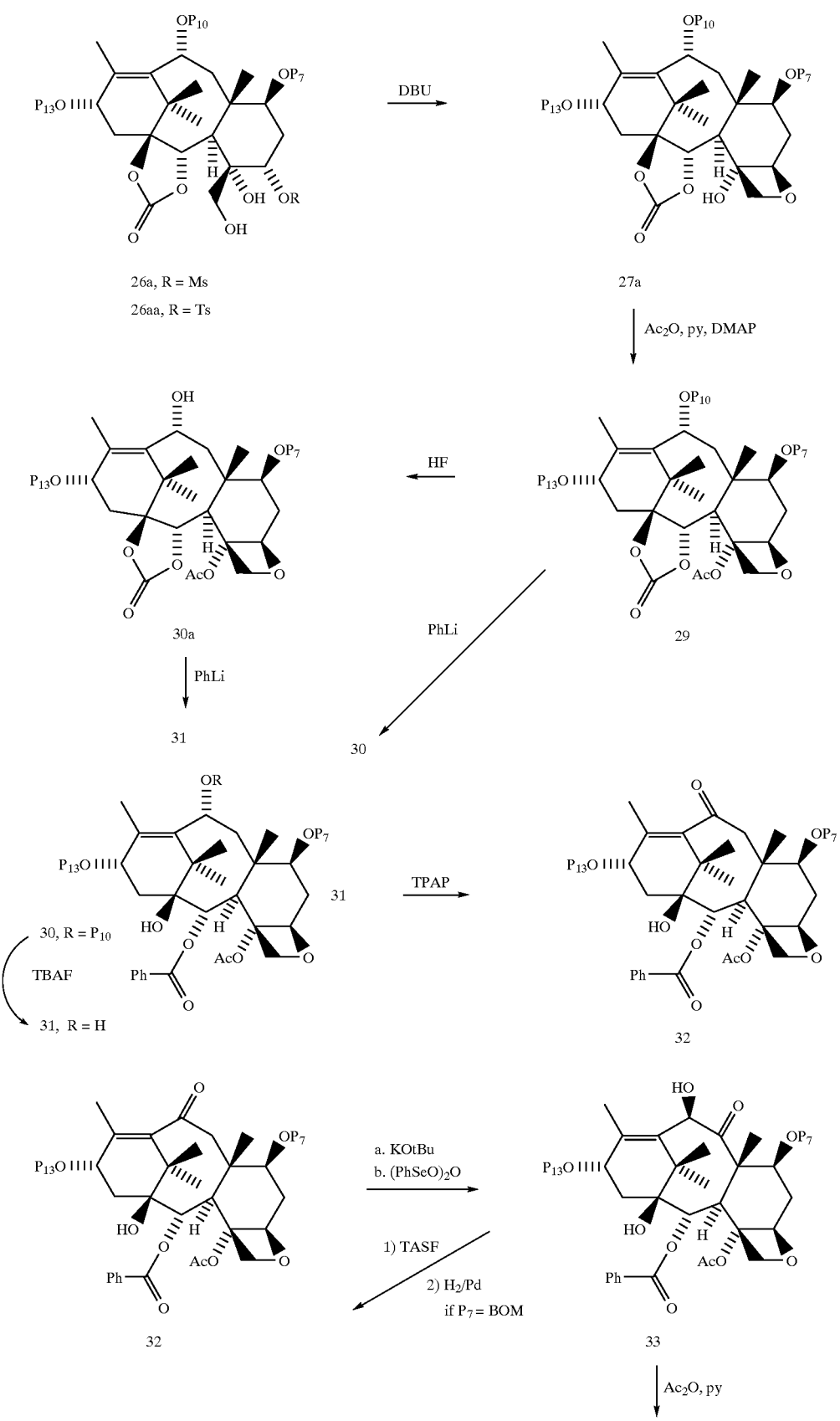

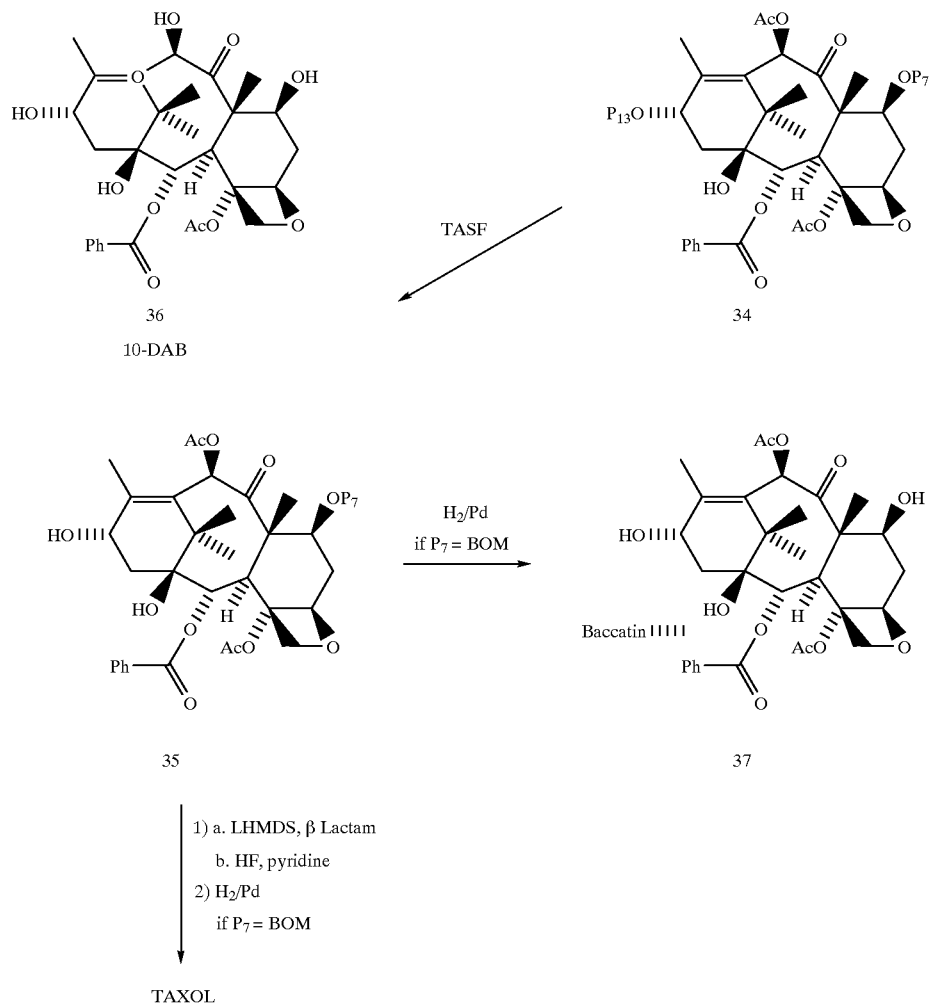

In Reaction Scheme A, $P_5$ is TMS, $P_7$ is MOP or BOM, $P_{10}$ is TES, $P_{13}$ is TBS, and R is ethyl in compounds 6 and 7, methyl in compounds 15, 16, and 17, Ms in compounds 24aa and 26a, and Ts in compound 26aa. It should be understood, however, that $P_5$, $P_7$, $P_{10}$, and $P_{13}$ may be other hydroxy protecting groups and R may comprise other lower alkyl substituents in compounds 6, 7, 15, 16 and 17.

Reaction Scheme A may be varied between compounds 18 and 29 as set forth below in Reaction Scheme A', with the reactions leading to compound 18 and following compound 29 being as set forth in Reaction Scheme A.

Reaction Scheme A'
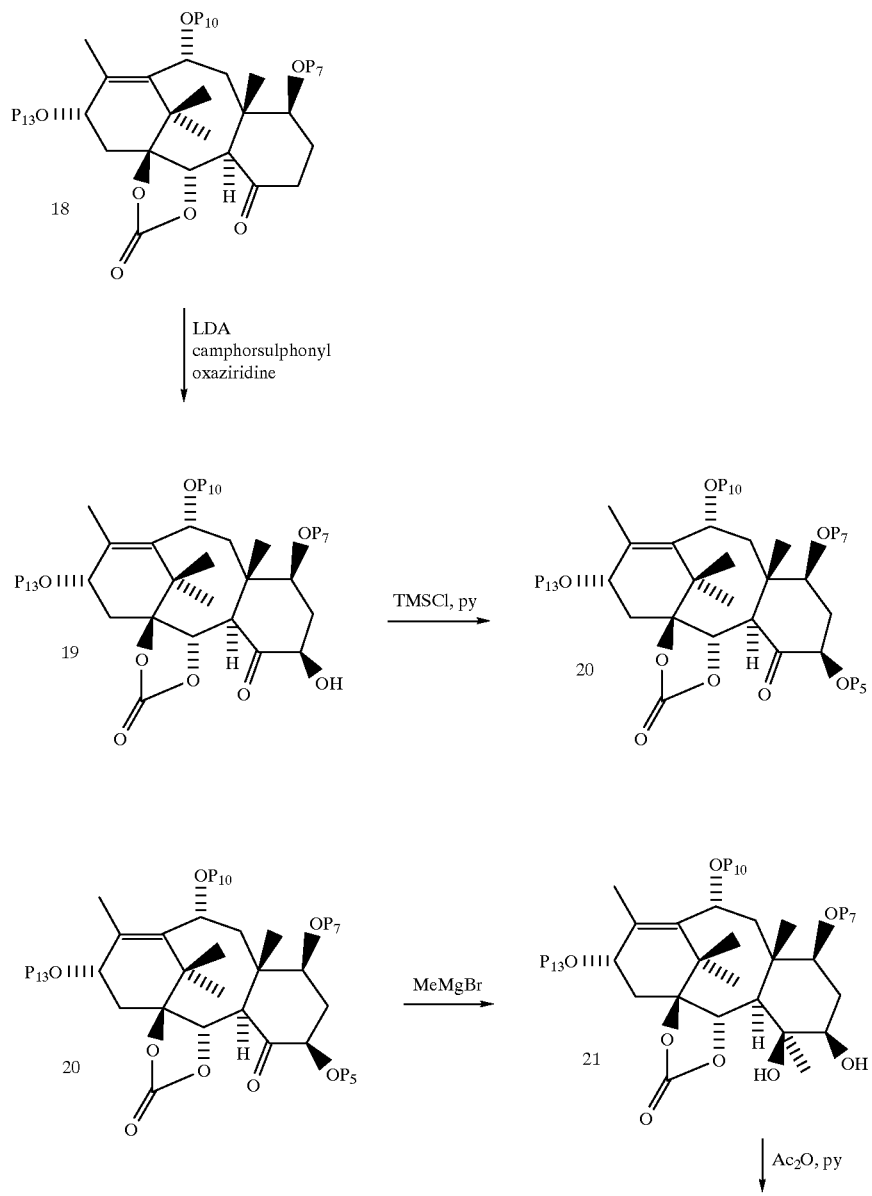

31 32
-continued
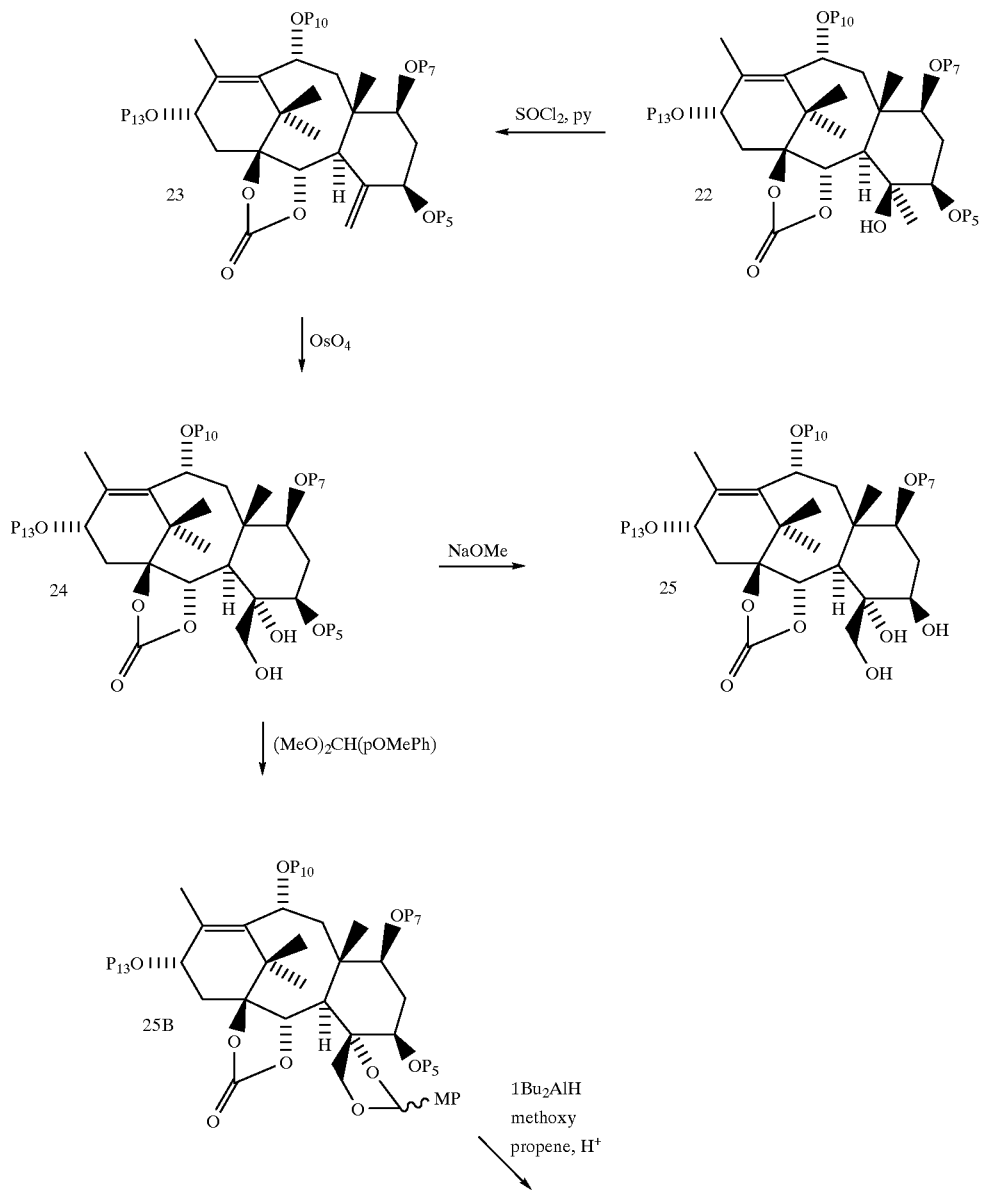

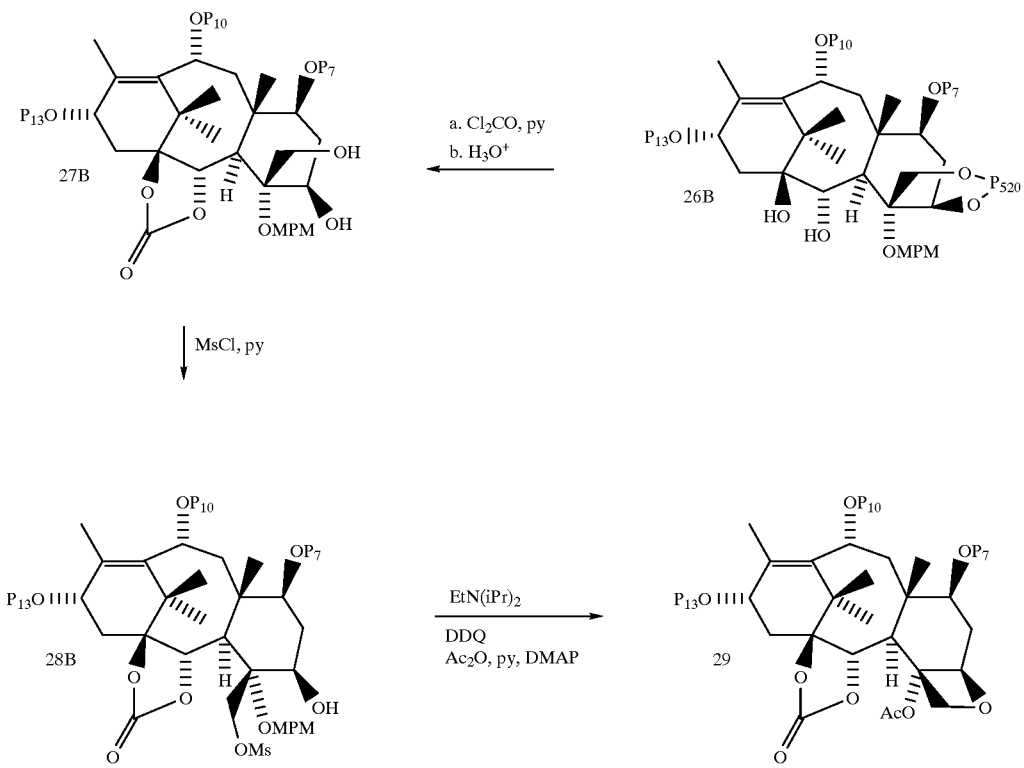

In Reaction Scheme A', $P_5$ is TMS or Ac, $P_7$ is MOP or BOM, $P_{10}$ is TES, $P_{13}$ is TBS and $P_{520}$ is acetal or ketal, preferably acetonide. It should be understood, however, that $P_5$, $P_7$, $P_{10}$, and $P_{13}$ and $P_{520}$ may be other hydroxy protecting groups.

In general, tricyclic and tetracyclic taxanes bearing C13 side chains may be obtained by reacting a β-lactam with alkoxides having the taxane tricyclic or tetracyclic nucleus and a C-13 metallic oxide substituent to form compounds having a β-amido ester substituent at C-13. The β-lactams have the following structural formula:

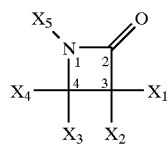

wherein $X_1$–$X_5$ are as defined above. The alkoxides having the tricyclic or tetracyclic taxane nucleus and a C-13 metallic oxide or ammonium oxide substituent have the following structural formula:

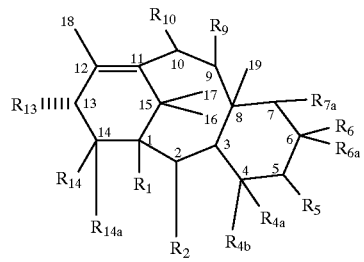

wherein $R_1$, $R_2$, $R_{4a}$, $R_{4b}$, $R_5$, $R_6$, $R_{6a}$, $R_{7a}$, $R_9$, $R_{10}$, $R_{14}$, and $R_{14a}$ are as previously defined, $R_{13}$ is -OM and M comprises ammonium or is a metal optionally selected from Group IA, IIA, transition (including lanthanides and actinides), IIB, IIIA IVA, VA, or VIA metals (CAS version) If M comprises ammonium, it is preferably tetraalkylammonium and the alkyl component of the tetraalkylammonium substituent is preferably $C_1$–$C_{10}$ alkyl such as methyl or butyl. Most preferably, the alkoxide has the tetracyclic taxane nucleus and corresponds to the structural formula:

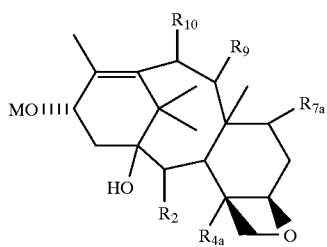

wherein M, $R_2$, $R_{4a}$, $R_{7a}$, $R_9$, and $R_{10}$ are as previously defined.

As set forth in Reaction Scheme A, taxol may be prepared by converting 7-protected Baccatin III 35 to the corresponding alkoxide and reacting the alkoxide with a β-lactam in which $X_1$ is protected hydroxy, $X_3$ is phenyl and $X_5$ is benzoyl. Protecting groups such as 2-methoxypropyl ("MOP"), 1-ethoxyethyl ("EE") are preferred, but a variety of other standard protecting groups such as the triethylsilyl group or other trialkyl (or aryl) silyl groups may be used.

Taxanes having alternative side chain substituents may be prepared through the use of β-lactams which comprise the alternative substituents.

Taxanes having alternative C9 substituents may be prepared by selectively reducing the C9 keto substituent of taxol, 10-DAB, Baccatin III or one of the other intermediates disclosed herein to yield the corresponding C9 β-hydroxy derivative. The reducing agent is preferably a borohydride and, most preferably, tetrabutylammoniumboro-hydride ($Bu_4NBH_4$) or triacetoxyborohydride.

As illustrated in Reaction Scheme 1, the reaction of baccatin III with $Bu_4NBH_4$ in methylene chloride yields 9-desoxo-9β-hydroxybaccatin III 5. After the C7 hydroxy group is protected with the triethylsilyl protecting group, for example, a suitable side chain may be attached to 7-protected-9β-hydroxy derivative 6 as elsewhere described herein. Removal of the remaining protecting groups thus yields 9β-hydroxy-desoxo taxol or other 9β-hydroxytetracylic taxane having a C13 side chain.

REACTION SCHEME 1

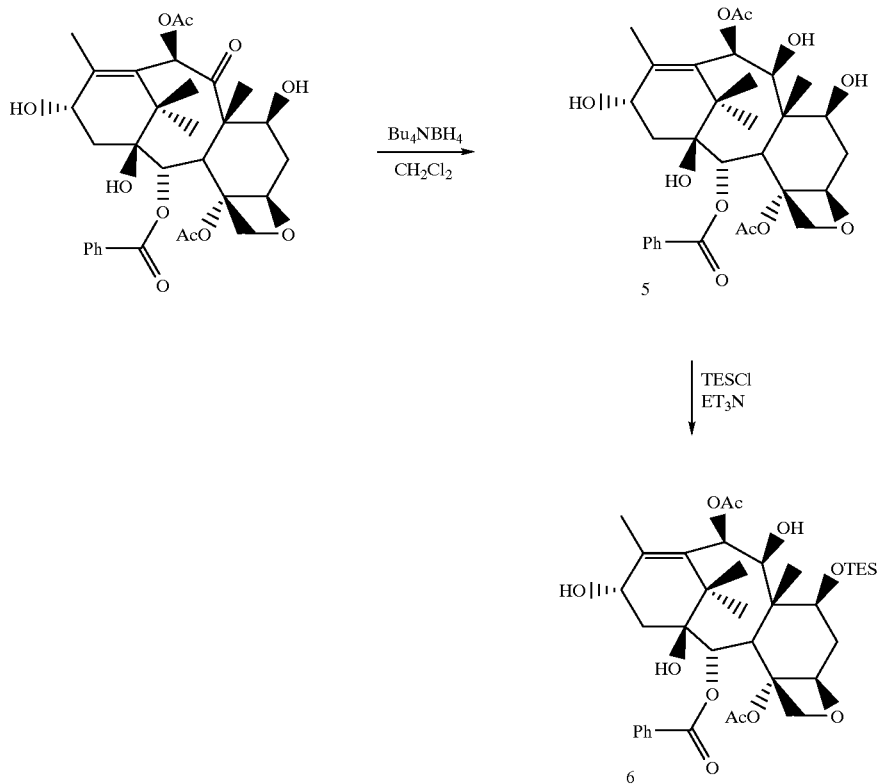

Alternatively, the C13 hydroxy group of 7-protected-9β-hydroxy derivative 6 may be protected with trimethylsilyl or other protecting group which can be selectively removed relative to the C7 hydroxy protecting group as illustrated in Reaction Scheme 2, to enable further selective manipulation of the various substituents of the taxane. For example, reaction of 7,13-protected-9β-hydroxy derivative 7 with KH causes the acetate group to migrate from C10 to C9 and the hydroxy group to migrate from C9 to C10, thereby yielding 10-desacetyl derivative 8. Protection of the C10 hydroxy group of 10-desacetyl derivative 8 with triethylsilyl yields derivative 9. Selective removal of the C13 hydroxy protecting group from derivative 9 yields derivative 10 to which a suitable side chain may be attached as described above.

REACTION SCHEME 2

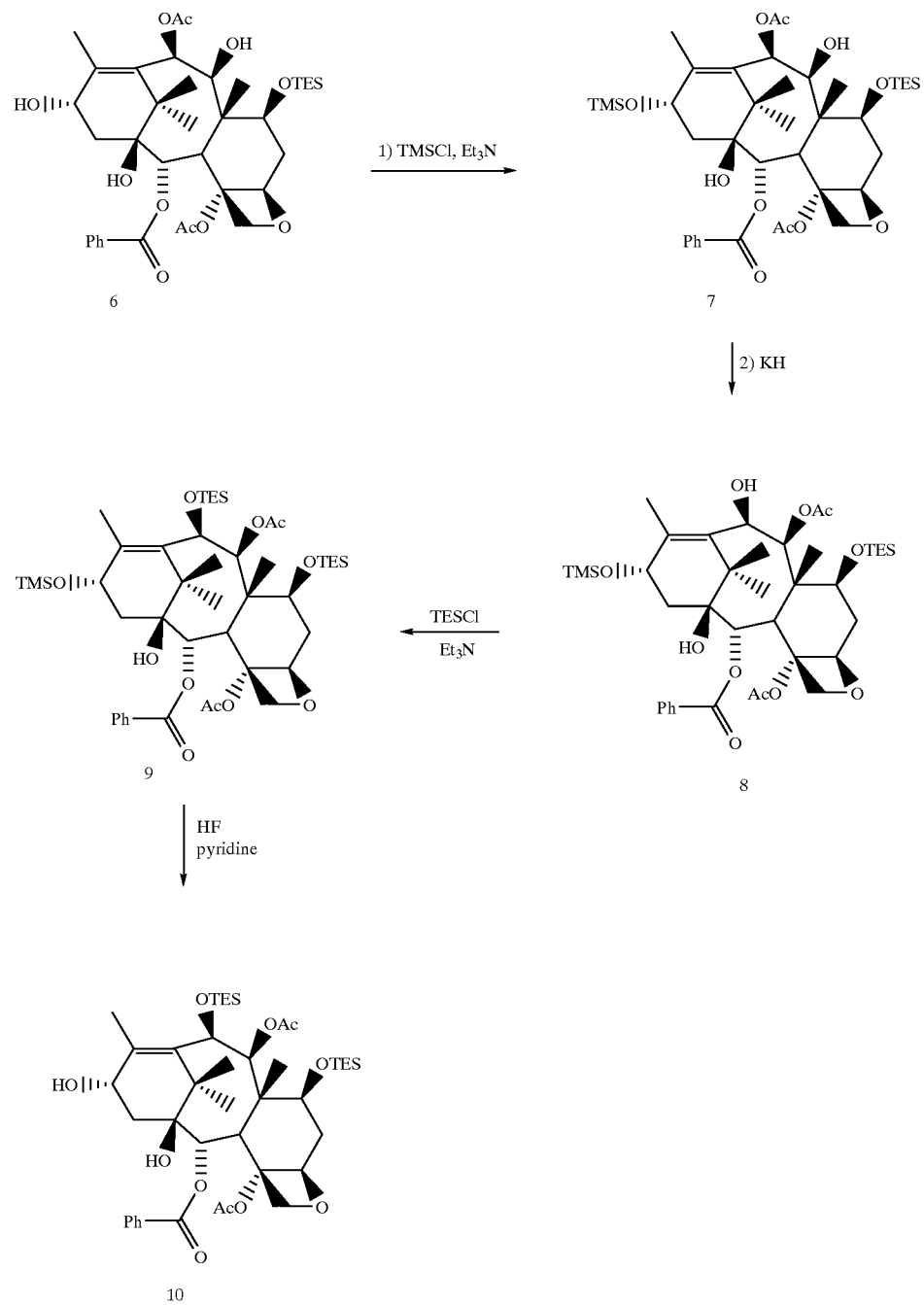

As shown in Reaction Scheme 3, 10-oxo derivative 11 can be provided by oxidation of 10-desacetyl derivative 8. Thereafter, the C13 hydroxy protecting group can be selectively removed followed by attachment of a side chain as described above to yield 9-acetoxy-10-oxo-taxol or other 9-acetoxy-10-oxotetracylic taxanes having a C13 side chain. Alternatively, the C9 acetate group can be selectively removed by reduction of 10-oxo derivative 11 with a reducing agent such as samarium diiodide to yield 9-desoxo-10-oxo derivative 12 from which the C13 hydroxy protecting group can be selectively removed followed by attachment of a side chain as described above to yield 9-desoxo-10-oxo-taxol or other 9-desoxo-10-oxotetracylic taxanes having a C13 side chain.

REACTION SCHEME 3

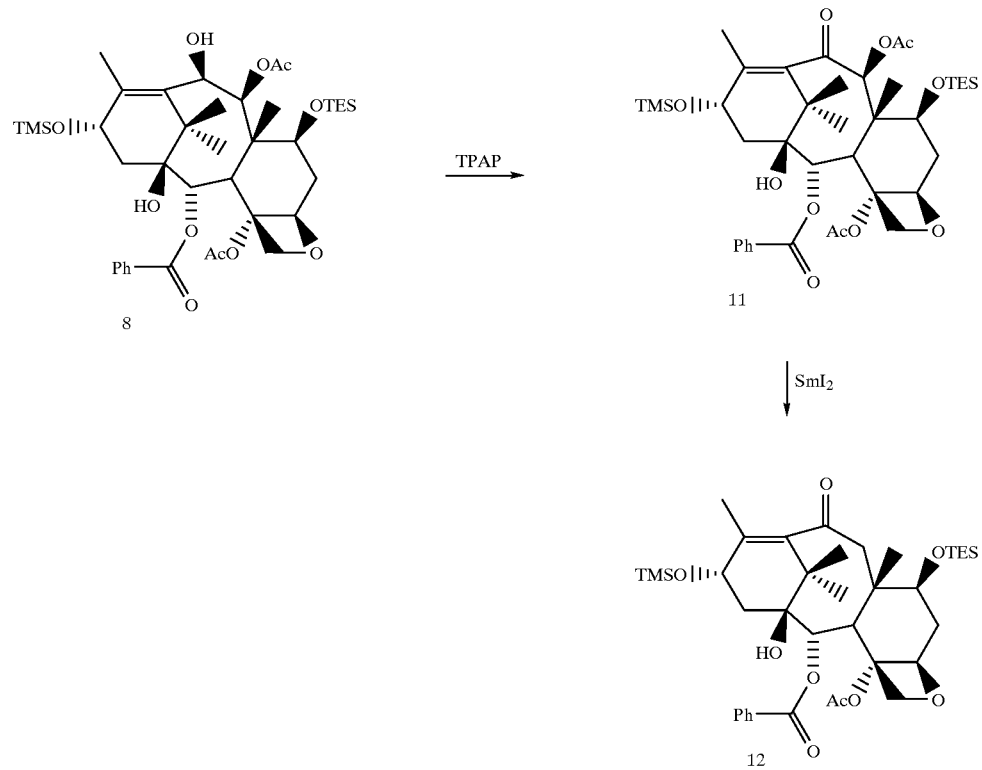

Reaction Scheme 4 illustrates a reaction in which 10-DAB is reduced to yield pentaol 13. The C7 and C10 hydroxyl groups of pentaol 13 can then be selectively protected with the triethylsilyl or another protecting group to produce triol 14 to which a C13 side chain can be attached as described above or, alternatively, after further modification of the tetracylic substituents.

REACTION SCHEME 4

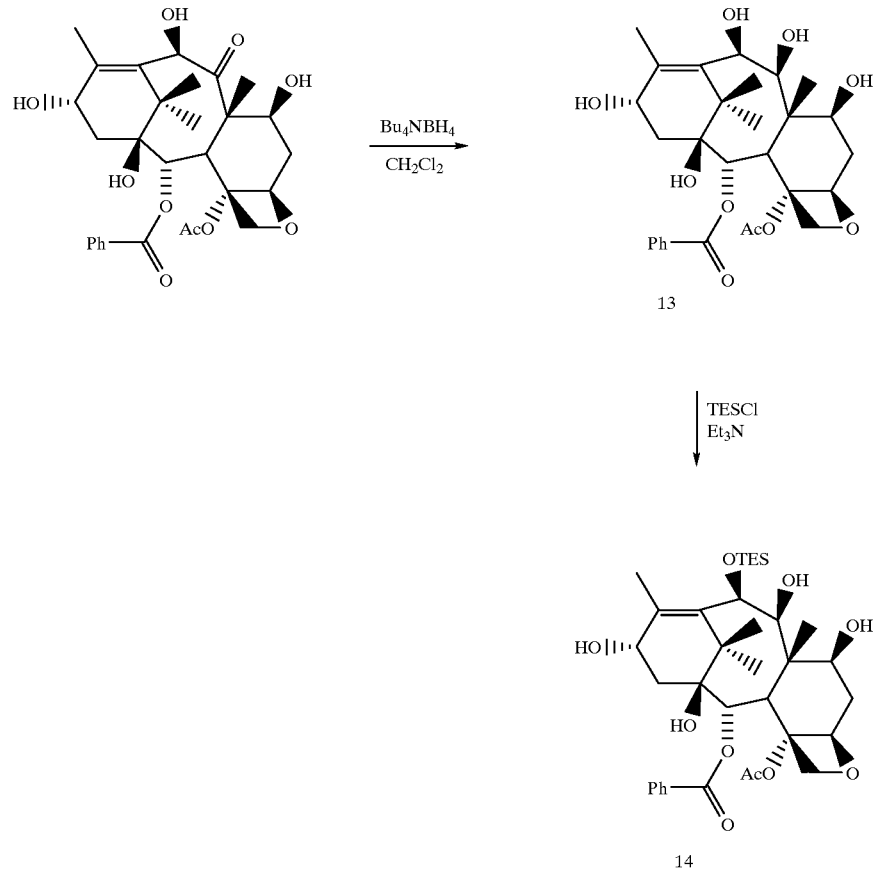

Taxanes having C9 and/or C10 acyloxy substituents other than acetate can be prepared using 10-DAB as a starting material as illustrated in Reaction Scheme 5. Reaction of 10-DAB with triethylsilyl chloride in pyridine yields 7-protected 10-DAB 15. The C10 hydroxy substituent of 7-protected 10-DAB 15 may then be readily acylated with any standard acylating agent to yield derivative 16 having a new C10 acyloxy substituent. Selective reduction of the C9 keto substituent of derivative 16 yields 9β-hydroxy derivative 17 to which a C13 side chain may be attached. Alternatively, the C10 and C9 groups can be caused to migrate as set forth in Reaction Scheme 2, above.

REACTION SCHEME 5

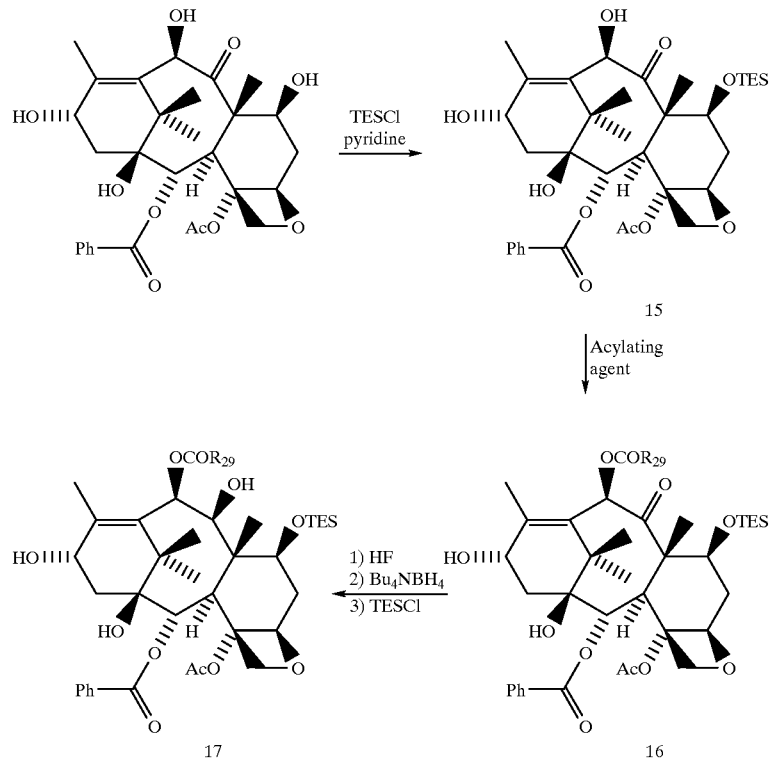

Taxanes having alternative C2 and/or C4 esters can be prepared using baccatin III and 10-DAB as starting materials. The C2 and/or C4 esters of baccatin III and 10-DAB can be selectively reduced to the corresponding alcohol(s) using reducing agents such as LAH or Red-Al, and new esters can thereafter be substituted using standard acylating agents such as anhydrides and acid chlorides in combination with an amine such as pyridine, triethylamine, DMAP, or diisopropyl ethyl amine. Alternatively, the C2 and/or C4 alcohols may be converted to new C2 and/or C4 esters through formation of the corresponding alkoxide by treatment of the alcohol with a suitable base such as LDA followed by an acylating agent such as an acid chloride.

Baccatin III and 10-DAB analogs having different substituents at C2 and/or C4 can be prepared as set forth in Reaction Schemes 6–10. To simplify the description, 10-DAB is used as the starting material. It should be understood, however, that baccatin III derivatives or analogs may be produced using the same series of reactions (except for the protection of the C10 hydroxy group) by simply replacing 10-DAB with baccatin III as the starting material. 9-desoxo derivatives of the baccatin III and 10-DAB analogs having different substituents at C2 and/or C4 can then be prepared by reducing the C9 keto substituent of these analogs and carrying out the other reactions described above.

In Reaction Scheme 6, protected 10-DAB 3 is converted to the triol 18 with lithium aluminum hydride. Triol 18 is then converted to the corresponding C4 ester using $Cl_2CO$ in pyridine followed by a nucleophilic agent (e.g., Grignard reagents or alkyllithium reagents).

Scheme 6

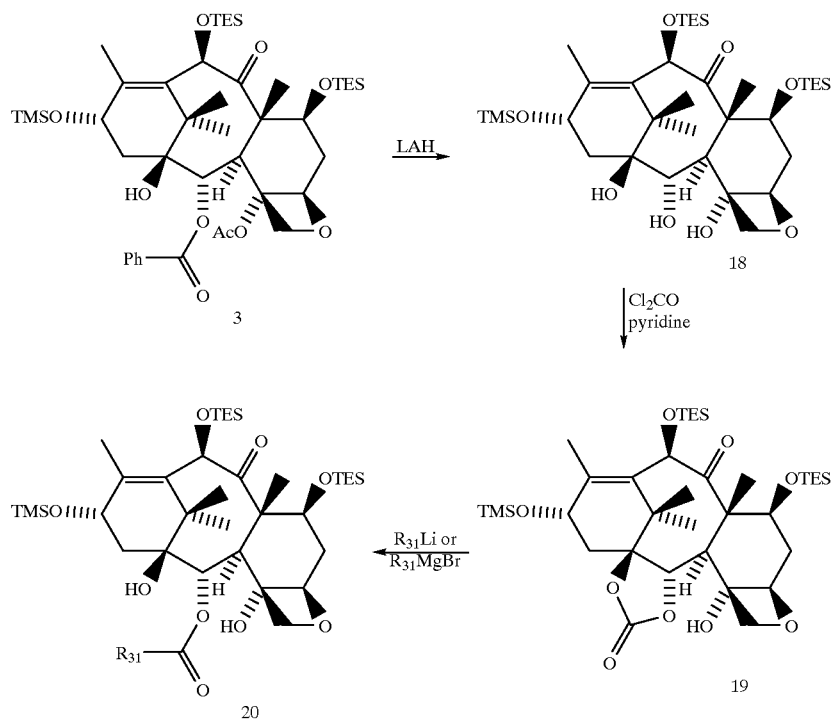

Deprotonation of triol 18 with LDA followed by introduction of an acid chloride selectively gives the C4 ester. For example, when acetyl chloride was used, triol 18 was converted to 1,2 diol 4 as set forth in Reaction Scheme 7.

Triol 18 can also readily be converted to the 1,2 carbonate 19. Acetylation of carbonate 19 under vigorous standard conditions provides carbonate 21 as described in Reaction Scheme 8; addition of alkyllithiums or Grignard reagents to carbonate 19 provides the C2 ester having a free hydroxyl group at C4 as set forth in Reaction Scheme 6.

Scheme 7

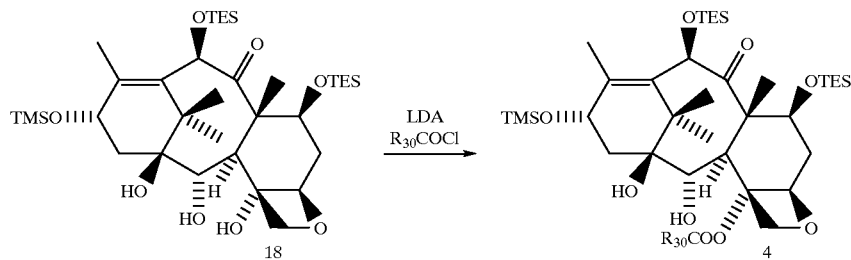

Scheme 8
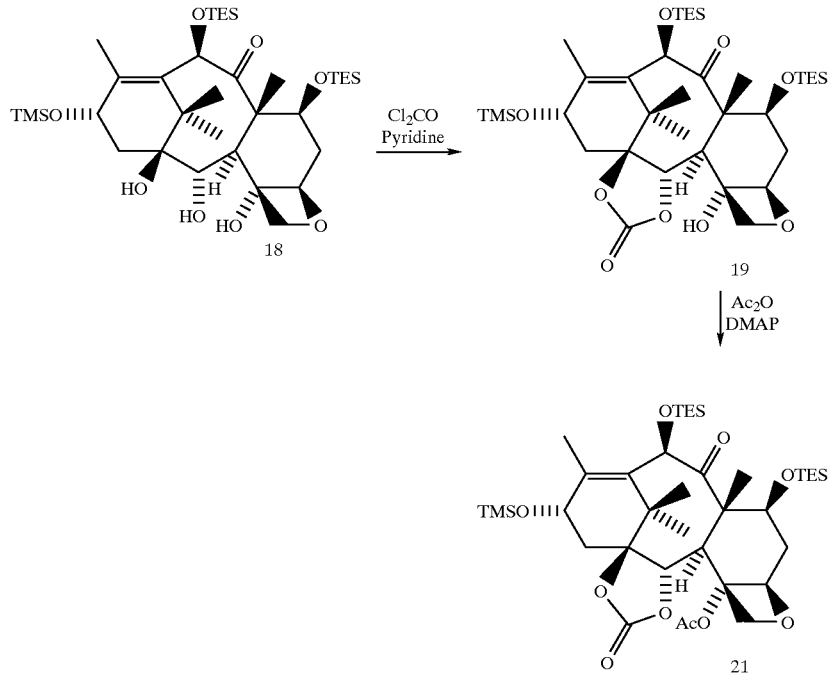
As set forth in Reaction Scheme 9, other C4 substituents can be provided by reacting carbonate 19 with an acid chloride and a tertiary amine to yield carbonate 22 which is then reacted with alkyllithiums or Grignard reagents to provide 10-DAB derivatives having new substituents at C2.
Scheme 9
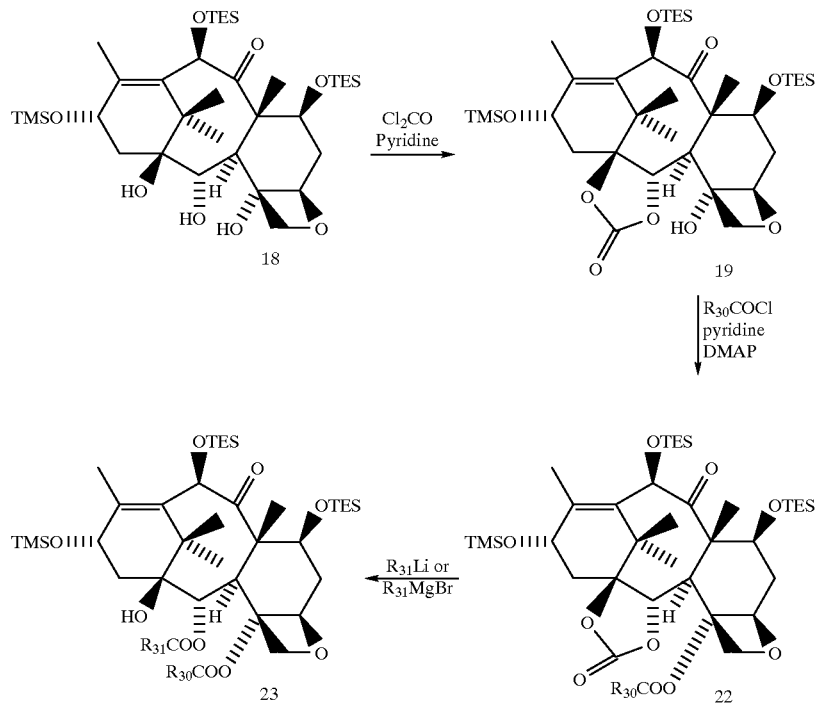

Alternatively, baccatin III may be used as a starting material and reacted as shown in Reaction Scheme 10. After being protected at C7 and C13, baccatin III is reduced with LAH to produce 1,2,4,10 tetraol 24. Tetraol 24 is converted to carbonate 25 using $Cl_2CO$ and pyridine, and carbonate 25 is acylated at C10 with an acid chloride and pyridine to produce carbonate 26 (as shown) or with acetic anhydride and pyridine (not shown). Acetylation of carbonate 26 under vigorous standard conditions provides carbonate 27 which is then reacted with alkyl lithiums to provide the baccatin III derivatives having new substituents at C2 and C10.

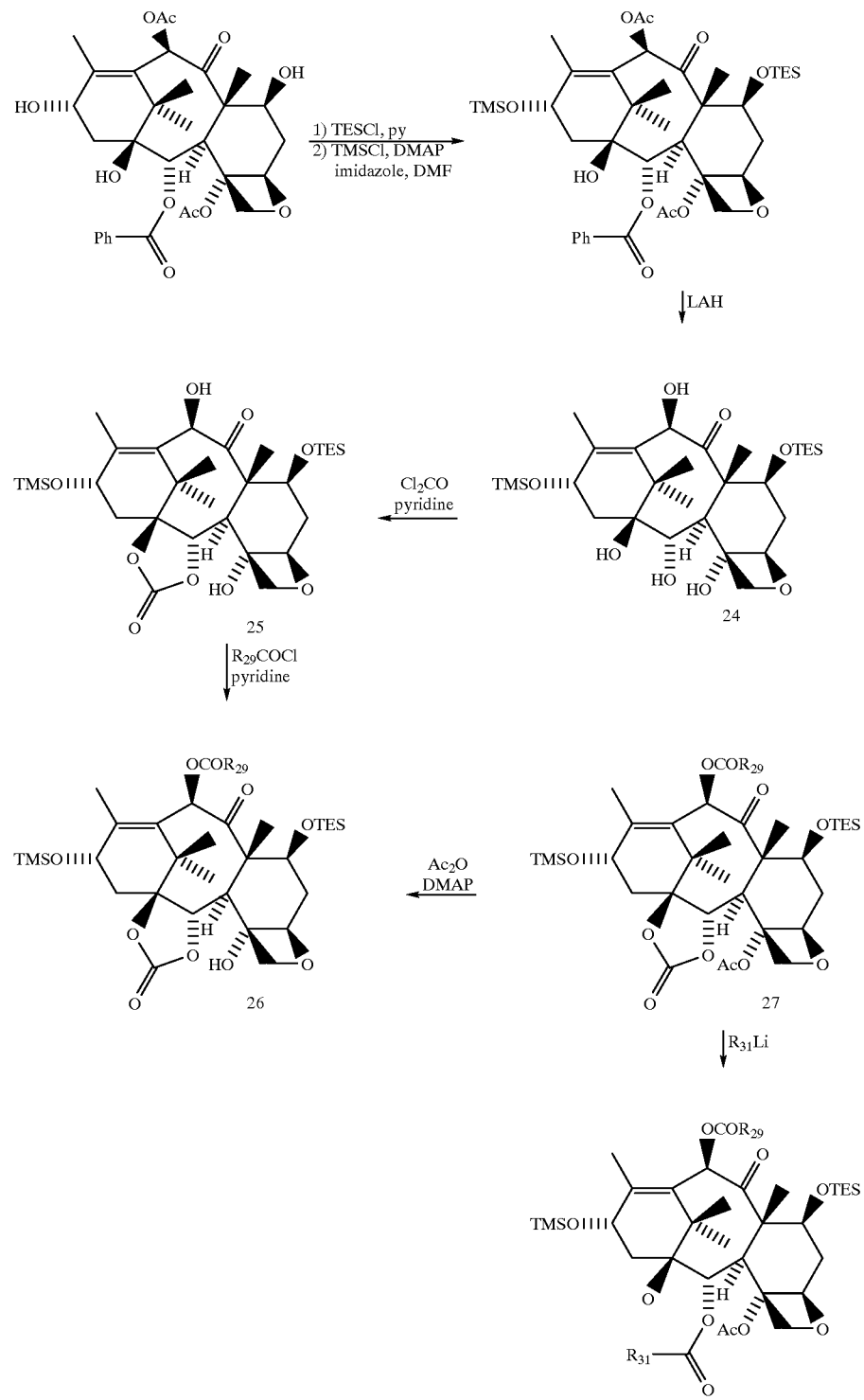

Scheme 10

10-desacetoxy derivatives of baccatin III and 10-desoxy derivatives of 10-DAB may be prepared by reacting baccatin III or 10-DAB (or their derivatives) with samarium diiodide. Reaction between the tetracyclic taxane having a C10 leaving group and samarium diiodide may be carried out at 0° C. in a solvent such as tetrahydrofuran. Advantageously, the samarium diiodide selectively abstracts the C10 leaving group; C13 side chains and other substituents on the tetracyclic nucleus remain undisturbed. Thereafter, the C9 keto substituent may be reduced to provide the corresponding 9-desoxo-9β-hydroxy-10-desacetyoxy or 10-desoxy derivatives as otherwise described herein.

C7 dihydro and other C7 substituted taxanes can be prepared as set forth in Reaction Schemes 11, 12 and 12a.

REACTION SCHEME 11

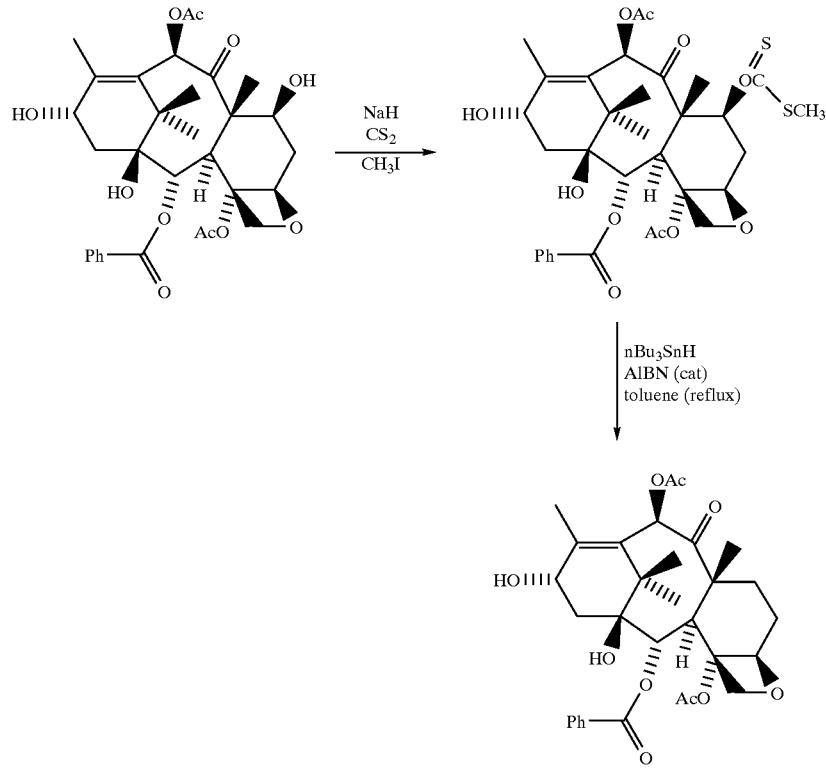

REACTION SCHEME 12

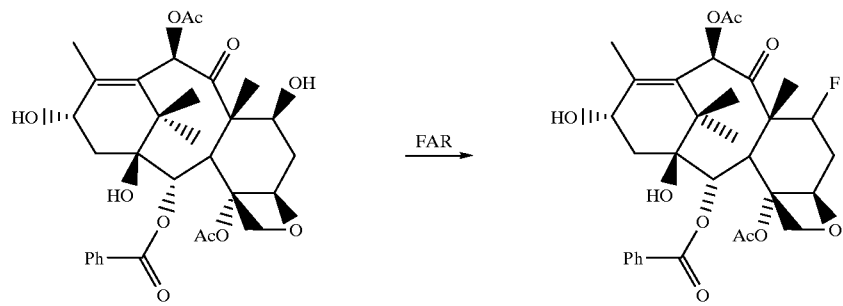

-continued

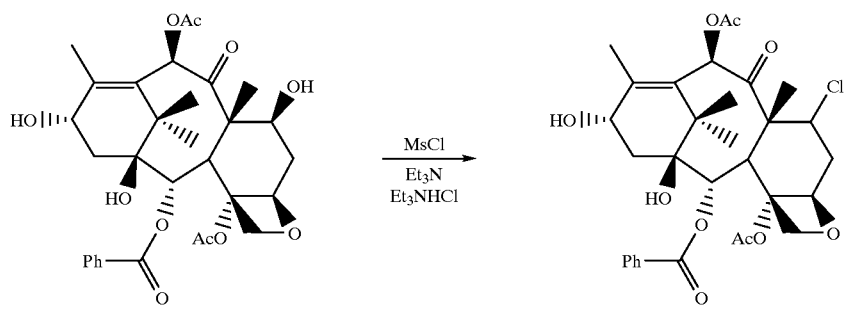

REACTION SCHEME 12a

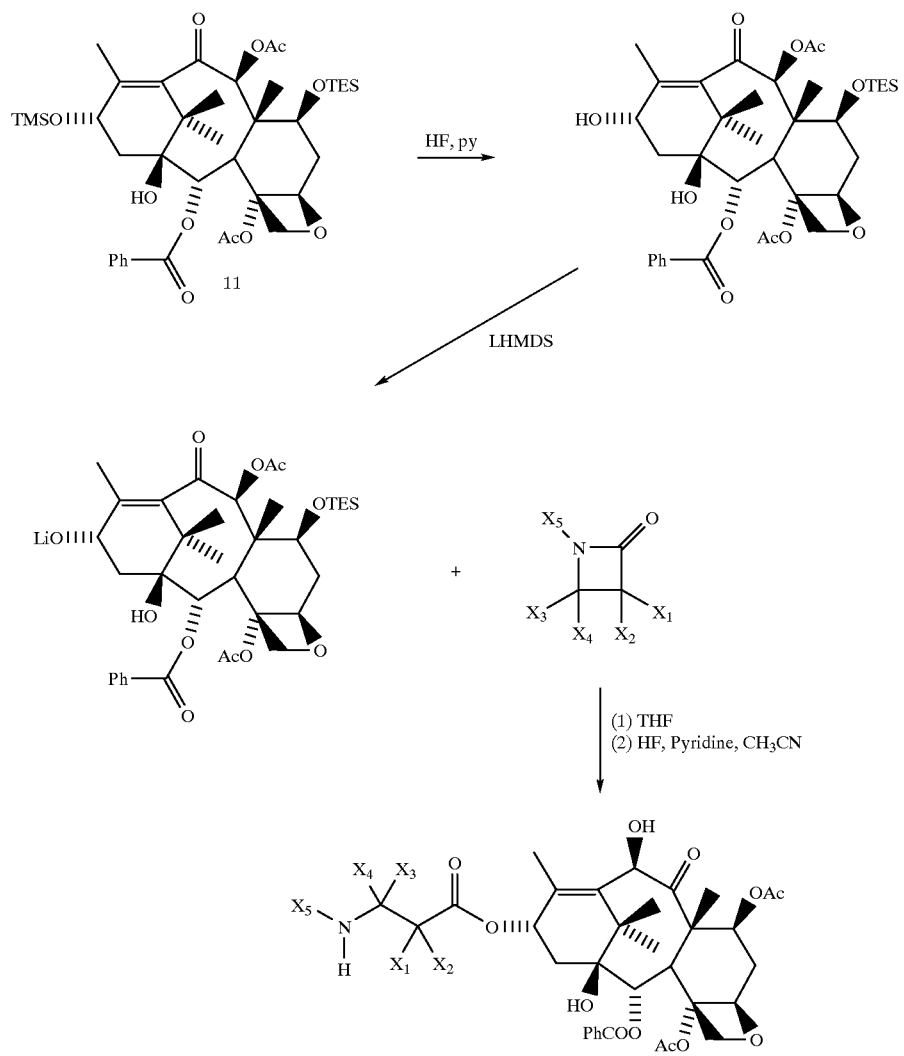

As shown in Reaction Scheme 12, Baccatin III may be converted into 7-fluoro baccatin III by treatment with FAR at room temperature in THF solution. Other baccatin derivatives with a free C7 hydroxyl group behave similarly. Alternatively, 7-chloro baccatin III can be prepared by treatment of baccatin III with methane sulfonyl chloride and triethylamine in methylene chloride solution containing an excess of triethylamine hydrochloride.

Taxanes having C7 acyloxy substituents can be prepared as set forth in Reaction Scheme 12a, 7,13-protected 10-oxoderivative 11 is converted to its corresponding C13 alkoxide by selectively removing the C13 protecting group and replacing it with a metal such as lithium. The alkoxide is then reacted with a β-lactam or other side chain precursor. Subsequent hydrolysis of the C7 protecting groups causes a migration of the C7 hydroxy substituent to C10, migration of the C10 oxo substituent to C9, and migration of the C9 acyloxy substituent to C7.

As shown in Reaction Scheme 13, 7-O-triethylsilyl baccatin III can be converted to a tricyclic taxane through the action of trimethyloxonium tetrafluoroborate in methylene chloride solution. The product diol then reacts with lead tetraacetate to provide the corresponding C4 ketone.

protected intermediate having a C3 carbonyl group and a C8a hydrogen. A variety of ketones or aldehydes can be used as a reactant in this process.

Formation of a cyclic carbonate from any 1,2 or 1,3 diol subunit in any intermediate can be carried out by using phosgene as a reactant. Carbonyl groups can be reduced by hydride reagents or metallic species to the corresponding alcohols. Alcohols can be oxidized using a variety of oxidizing agents as exemplified in the Reaction Schemes, to the corresponding carbonyl groups.

The compounds disclosed in this application have several asymmetric carbons and may exist in diastereomeric, racemic, or optically active forms. All of these forms are

REACTION SCHEME 13

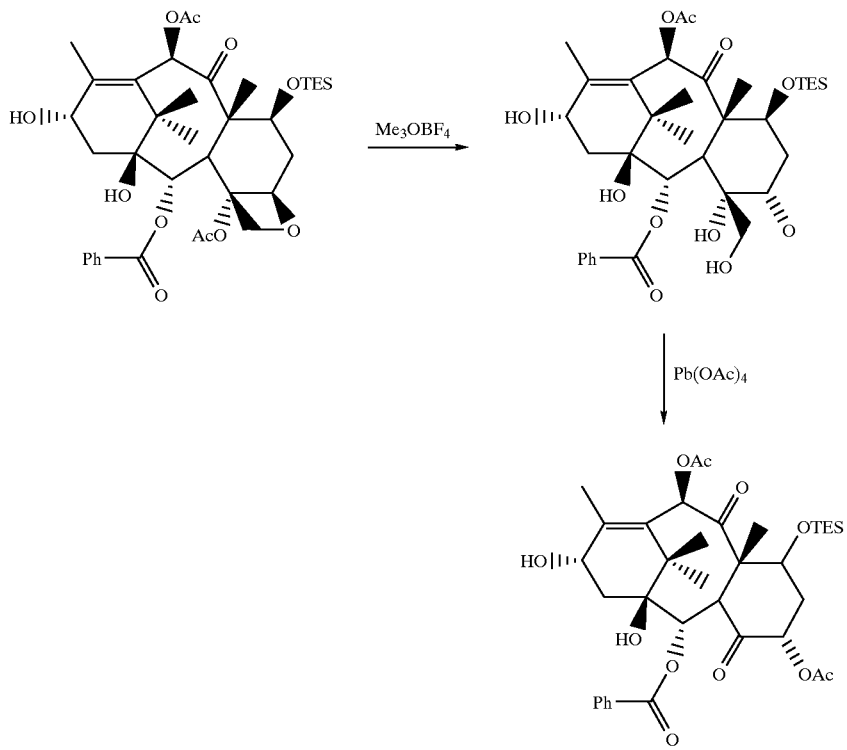

The subprocesses of Reaction scheme A can be applied at various stages. For example, the process for the conversion of compound 30 to compound 33 can be applied to any intermediate having a hydroxyl group at C-10 and two hydrogens at C-9, e.g., the process for introducing C9 and C10 carbonyl and hydroxyl groups can be applied to suitably protected intermediates 4 through 29.

Likewise, the process for introduction of C1 and C2 oxygen-containing functional groups (conversion of 6 to 13 in Reaction Scheme A) can be applied to any intermediate having a C3 carbonyl group.

Similarly, the process for introducing C2 and C4 acyl groups as exemplified in Reaction Schemes 6 through 10 can be applied to any intermediate having a C1, C2 carbonate.

Also, the process for forming the oxetane ring, as exemplified in the conversion of 24a to 27a in Reaction Scheme A, can be applied to a variety of intermediates having a C4 carbonyl group.

The aldol process exemplified in the conversion of 5 to 6 in Reaction Scheme A can be applied to any suitably contemplated within the scope of this invention. More specifically, the present invention includes the enantiomers, diasteriomers, racemic mixtures, and other mixtures of the compounds disclosed herein.

The following examples illustrate the invention.

EXAMPLES

Reaction Scheme A

Triethylsilyloxy alcohol 3. To a solution of diol 2 (3.16 g, 13.4 mmol) and DMAP (70 mg, 0.57 mmol) in CH$_2$Cl$_2$ (65 mL) at room temperature was added triethylamine (3.7 mL, 26.6 mmol) followed by dropwise addition of TESCl (2.7 mL, 16.1 mmol). After 1.75 h, the reaction mixture was diluted with 150 mL of hexane, then poured into 100 mL of a saturated aqueous NaHCO$_3$ solution and 150 mL of hexane. The organic phase was washed with two 100 mL portions of saturated aqueous NaHCO$_3$ solution and with 100 mL of water, dried over anhydrous Na$_2$SO$_4$, and concentrated under reduced pressure to give 4.88 g of crude triethylsilyloxyalcohol 3. An analytical sample was obtained by plug filtration through a short pad of silica gel washing with hexane and then eluting the pure compound 3 ($P_{10}$=TES) (colorless oil) with 5% ethyl acetate in hexane.

3 ($P_{10}$=TES): $^1$H NMR (300 MHz, CDCl$_3$) δ 0.61 (q, J=7.7 Hz, 6H, TES CH$_2$), 0.89 (s, 3H, CH$_3$ 16), 0.96 (t, J=7.7 Hz, 9H, TES CH$_3$), 1.03 (d, J=7.1 Hz, 3H, CH$_3$ 19), 1.07 (s, 3H, CH$_3$ 17), 1.23 (d, J=14.3 Hz, 1H, H2α), 1.56 (dd, J=6.0, 6.0 Hz, 1H, H7),.1.76 (ddd, J=5.0, 11.0, 13.7 Hz, 1H, H9), 1.90 (ddd, J=2.2, 8.8, 15.4 Hz, 1H, H9), 1.96 (m, 1H, H14α), 2.37 (m, 2H, H2β, H14β), 2.51 (ddd, J=7.7, 7.7, 10.4 Hz, 1H, H8α), 2.94 (s, 1H, OH-3), 4.21 (dd, J=2.2, 5.0 Hz, 1H, H10), 5.43 (dd, J=2.8, 2.8 Hz, 1H, H13). $^{13}$C NMR (75 MHz, CDCl$_3$) δ (ppm) 4.8 (TES CH$_2$), 6.7 (TES CH$_3$), 15.02 (CH$_3$ 19), 23.0 (CH$_3$ 17), 26.2 (CH$_3$ 18), 28.0 (CH$_3$ 16), 33.6 (C14), 41.5 (C8), 44.2 (C2), 45.0 (C1), 45.2 (C15), 45.8 (C9), 69.6 (C11), 74.9 (C10), 96.0 (C3), 123.0 (C13), 143.7 (C12); IR (CHCl$_3$) ν 3530, 2970, 2930, 2900, 1460, 1340, 1140, 1100, 1080, 1045, 1010, 970, 915, 650 cm$^{-1}$; MS (CI) 351 (M+1, 58), 333 (100), 219 (34).

Hydroxy Ketone 4. To a vigorously stirred solution of the crude compound 3 ($P_{10}$=TES) in anhydrous CH$_2$Cl$_2$ (30 mL) at 0° C. under nitrogen was added Ti (O$^i$Pr)$_4$ (13.5 mL, 43.1 mmol) followed by dropwise addition of anhydrous 2M $^t$-BuOOH in hexane (18 mL, 36 mmol). After 45 min dimethylsulfide (15 mL) was added slowly over a period of 5 min. The solution was stirred for 10 min at 0° C., then 15 min at room temperature and then moved to a 55° C. bath where it was heated under reflux for 8 h. The solvents were evaporated under reduced pressure, the resulting thick syrup was dissolved in ethyl acetate (850 mL) and 3.5 mL of H$_2$O was added dropwise with vigorous stirring. The resulting mixture was stirred at room temperature for 1 h and then filtered through a pad of Celite which was further washed with two protions of 100 mL of ethyl acetate. Evaporation of the solvent under reduced pressure afforded an oil that was filtered through a short pad of silica gel eluting with 10% ethyl acetate in hexane to give 4.78 g of pure hydroxyketone 4 ($P_{10}$=TES) (colorless oil).

4 ($P_{10}$=TES): $^1$H NMR (300 MHz, CDCl$_3$) δ 0.58 (q, J=7.7 Hz, 6H, TES CH$_2$), 0.94 (t, J=7.7 Hz, 12H, CH$_3$ 19, TES CH$_3$), 0.98 (s, 3H, CH$_3$ 17), 1.31 (s, 3H, CH$_3$ 16), 1.71 (dd, J=5.0, 11.5 Hz, 1H, H2α), 1.85 (m, 3H, H1, H9β, H14β), 1.96 (s, 3H, CH$_3$ 18), 2.15 (d, J=12.1, 1H, OH-13), 2.22 (ddd, J=4.9, 13.2, 15.9 Hz, 1H, H9α), 2.56 (dddd, J=3.8, 7.1, 13.7, 13.7 Hz, 1H, H8α), 2.75 (dd, J=2.2, 11.0 Hz, 1H, H2β), 2.80 (ddd, J=4.4, 7.7, 11.0 Hz, 1H, H14β), 4.10 (t, J=11.0 HZ, 1H, H13β), 4.56 (d, J=5.0 Hz, 1H, H10β); $^{13}$C NMR (75 MHz, CDCl$_3$) δ (ppm) 4.3 (TES CH$_2$), 6.5 (TES CH$_3$), 13.4 (CH$_3$ 18), 18.4 (CH$_3$19), 25.8 (CH$_3$ 17), 27.1 (CH$_3$ 16), 34.7 (C14), 38.2 (C15), 38.8 (C2), 44.0 (C8), 44.2 (C9), 47.8 (C1), 67.3 (C13), 69.7 (C10), 137.3 (C11), 138.8 (C12), 219.2 (C3); IR (CHCl$_3$) ν 3550, 2960, 2880, 1660, 1460, 1410, 1240, 1200, 1160, 1140, 1080, 1050, 1000, 980, 900, 810 cm$^{-1}$; MS (CI) 367 (M+1, 2), 349 (100), 331 (55).

Ketone 5. To a solution of hydroxyketone 4 ($P_{10}$=TES) in anhydrous pyridine (25 mL) at −23° C. under nitrogen was added dropwise TBSOTf (3.2 mL, 13.9 mmol). After 5 min, the flask was moved to an ice bath and stirred for 1.75 h. The solution was diluted with 75 mL of hexane at 0° C. and then decanted from the insoluble oil into saturated aqueous NaHCO$_3$ solution (200 mL). The remaining oil was extracted with three 75 mL portions of hexane. The combined organic phases were washed with two 50 mL portions of saturated aqueous NaHCO$_3$ solution and then with 50 mL of water, dried over anhydrous Na$_2$SO$_4$ and concentrated under reduced pressure. The yellowish oily residue was purified by filtration through a short pad of silica gel eluting with 10% ethyl acetate in hexane to give 4.78 g of pure ketone 5 ($P_{10}$=TES, $P_{13}$=TBS) (94% yield from 2).

5 ($P_{10}$=TES, $P_{13}$=TBS): $^1$H NMR (300 MHz, CDCl$_3$) δ 0.03 (s, 3H, TBS CH$_3$), 0.05 (s, 3H, TBS CH$_3$), 0.57 (q, J=8.2 Hz, 6H, TES CH$_2$), 0.93 (t, J=8.2 Hz, 9H, TES CH$_3$), 0.93 (s, 9H, TBS t-Bu), 0.96 (d, J=1.8 Hz, 3H, CH$_3$ 19), 1.06 (s, 3H, CH$_3$ 17), 1.33 (s, 3H, CH$_3$ 16), 1.68 (dd, J=5.5, 11.5 Hz, 1H, H2α), 1.84 (m, 2H, H1, H9β), 1.89 (s, 3H, CH$_3$ 18), 1.92 (dd, J=6.0, 14.3 Hz, 1H, H14α), 2.21 (ddd, J=5.5, 13.2, 15.4 Hz, 1H, H9α), 2.39 (ddd, J=8.2, 10.4, 14.3 Hz, 1H, H14β), 2.52 (ddd, J=3.9, 7.1, 13.6 Hz, 1H, H8α), 2.66 (dd, J=2.8, 11.5 Hz, 1H, H2β), 4.45 (dd, J=5.5, 10.4 Hz, 1H, H13β), 4.61 (d, J=5.0 Hz, 1H, H10β); $^{13}$C NMR δ (ppm) −5.4 (TBS CH$_3$), −4.6 (TES CH$_3$), 4.3 (TES CH$_2$), 6.5 (TES CH$_3$), 14.1 (CH$_3$ 18), 17.9 (TBS C(CH$_3$)$_3$), 19.1 (CH$_3$ 19), 25.4 (CH$_3$ 17), 25.8 (TBS C(CH$_3$)$_3$), 26.8 (CH$_3$ 16), 33.5 (C14), 38.6 (C15), 39.4 (C2), 43.7 (C8), 44.4 (C9), 47.5 (C1), 67.5 (C13), 69.5 (C10), 136.8 (C11), 138.8 (C12), 213.5 (C3); IR (CHCl$_3$) ν 2950, 2900, 1680, 1460, 1420, 1395, 1365, 1250, 1200, 1110, 1080, 1000, 900, 860, 840 cm$^{-1}$; MS (CI) 481 (M+1, 3), 463 (16), 349 (100), 331 (50); Anal. Calcd. for C$_{27}$H$_{52}$O$_3$Si$_2$: C, 67.44; H, 10.90. Found: C, 67.31; H, 10.78.

Ketocarbonate 6. To asairred solution of diisopropylamine (0.60 mL, 4.28 mmol) in THF (11 mL) under nitrogen at room temperature was added 1.26 mL of a 3.1 M solution (3.89 mmol) of MeMgBr in ether. After 3 h, a solution of ketone 5 ($P_{10}$=TES, $P_{13}$=TBS) (750 mg, 1.56 mmol) in THF (3.5 mL) was added dropwise at room temperature. After 1.5 h, the reaction mixture was cooled to −23° C. and a solution of 4-pentenal (327 mg, 3.89 mmol) in THF (4 mL) was added dropwise down the side of the flask. After 1 h, 10 ml, of a saturated aqueous NH$_4$Cl solution was added. Ater 2 min, the reaction mixture was diluted with 100 mL of hexane, then poured into 100 mL of H$_2$O. The organic phase was washed with 100 mL of H$_2$O and 100 mL of brine, and dried over anhydrous Na$_2$SO$_4$ and concentrated under reduced pressure to give 0.92 g of a yellow oil. To a solution of the crude mixture in CH$_2$Cl$_2$ (10 mL) and pyridine (10 mL) under nitrogen at −23° C. was added 2.3 mL of 4 M solution (9.36 mmol) of phosgene in toluene dropwise and the reaction mixture was warmed to −10° C. After 30 min, ethanol (3.7 mL) was added and the resulting mixture was stirred for 30 min. The reaction mixture was then diluted with 300 mL of hexane, washed with 200 mL of a saturated aqueous NaHCO$_3$ solution, 200 mL, of a 10% aqueous CuSO$_4$ solution, 200 mL of H$_2$O, 200 mL of a saturated aqueous NaHCO$_3$ solution and 200 mL of brine, dried over anhydrous Na$_2$SO$_4$ and concentrated under reduced pressure to give 1.05 g of a yellow solid. The crude mixture was filtered through silica gel with 10% ethyl acetate in hexanes to give 965 mg of a white solid which was further purified by silica gel chromatography eluting with 2% ethyl acetate in hexanes to yield 745 mg (75%) of ketocarbonate 6 ($P_{10}$=TES, $P_{13}$=TBS, R=Et) as a white solid. The product was isolated as a 6:1 ratio of conformational isomers. The following NMR data is for the predominant conformer.

6 ($P_{10}$=TES, $P_{13}$=TBS, R=Et): mp 103–104° C.; $^1$H NMR (500 MHz, CDCl$_3$) δ 0.08 (s, 3H, TBS CH$_3$), 0.08 (s, 3H, TBS CH$_3$), 0.56 (q, J=7.8 Hz, 6H, TES CH$_2$), 0.94 (t, J=7.8 Hz, 9H, TES CH$_3$), 0.96 (s, 9H, TBS t-Bu), 1.08 (s, 3H, CH$_3$ 17), 1.29 (m, 1H, H6), 1.38 (s, 3H, CH$_3$ 19), 1.42 (s, 3H, CH$_3$ 16), 1.66 (dd, J=4.6, 12.5 Hz, 1H, H9α), 1.83 (s, 3H, CH$_3$ 18), 1.85 (dd, J=4.5, 4.5 Hz, 1H, H14α) 2.05 (m, 1H,

H5), 2.06 (dd, J=6.4, 14.2 Hz, 1H, H5), 2.47 (m, 2H, H9α:, H6), 3.01 (dd, J=3.7, 12.3 Hz, 1H, H14β), 4.20 (m, 2H, H2α, H2β), 4.47 (d, J=7.3 Hz, 1H, H13β), 4.50 (dd, J=4.6, 11.4 Hz, 1H, H10β), 4.91 (dd, J=1.83, 10.1 Hz, 1H, H20), 4.97 (dd, J=1.8, 16.9 Hz, 1H, H20), 5.29 (dd, J=0.9, 10.1 Hz, 1H, H7), 5.73 (dddd, J=6.9, 6.9, 10.5, 16.9 Hz, 1H, H4); $^{13}$C NMR δ (ppm) −5.3 (TBS $CH_3$), −4.5 (TBS $CH_3$), 4.8 (TES $CH_2$), 6.5 (TES $CH_3$), 14.0 (OEt $CH_3$), 15.5 ($CH_3$ 19), 15.9 ($CH_3$ 18), 18.1 (TBS $\underline{C}(CH_3)_3$), 25.8 (TES C($\underline{CH}_3$)$_3$), 27.6 ($CH_3$ 17), 28.2 ($CH_3$ 16), 30.4, 30.5 (C5, C6), 34.1 (C14), 39.0 (C15), 41.1 (C2), 47.1 (C1), 47.5 (C9), 55.1 (C8), 63.8 (OEt CH2), 66.3 (C13), 68.3 (C10), 84.0 (C7), 114.8 (C20), 134.8 (C11), 138.1 (C4'), 144.9 (C12), 155.7 (Ethylcarbonate C=O), 214.8 (C3); IR ($CCl_4$) ν 3000, 2950, 2900, 1770, 1700, 1490, 1390, 1280, 1140, 1100, 1030, 910, 880, 860 cm$^{-1}$; MS (EI) 636 (M, 100), 593 (20), 538 (34), 409 (33); Anal. Calcd. for $C_{35}H_{64}O_6Si_2$: C, 65.99; H, 10.13. Found: C, 65.88, H, 10.17.

Hydroxyketone 7. To a stirred solution of ketocarbonate 6 ($P_{10}$=TES, $P_{13}$=TBS, R=Et) (4.00 g, 6.28 mmol) in THF (65 mL) under nitrogen at −35° C. was added 50 mL of a 0.2 M solution (10 mmol) of LDA in THF down the side of the flask over a 10 min period. After 30 min, the reaction mixture was cooled to −78° C. and 2.29 g of (R)-camphorylsulfonyl oxaziridine (10 nmol) in THF (18 mL) was added dropwise down the side of the flask. After 30 min, the reacion mixture was quenched with 300 mL of a saturated aqueous $NaHCO_3$ solution and extracted with 500 mL and then 150 mL of 25% ethyl acetate in hexanes. The combined organic phases were washed with brine, dried over anhydrous $Na_2SO_4$ and concentrated under reduced pressure to yield 7 g of a waxy solid. This material was purified by flash chromatography, eluting with 3% ethyl acetate in hexanes to yield 3.50 g of hydrxyketone 7 ($P_{10}$=TES, $P_{13}$=TBS, R=Et) (85%).

7 ($P_{10}$=TES, $P_{13}$=TBS, R=Et): $^1$H NMR (500 MHz, $CDCl_3$) δ 0.01 (s, 3H, TBS $CH_3$), 0.03 (s, 3H, TBS $CH_3$), 0.50 (q, J=7.8 Hz, 6H, TES $CH_2$), 0.87 (t, J=7.8 Hz, 9H, TES $CH_3$), 0.90 (s, 9H, TBS t-Bu), 1.03 (s, 3H, $CH_3$ 17), 1.25 (t, J=7.0 Hz, 3H, OEt $CH_3$), 1.35 (s, 3H, $CH_3$ 19), 1.40 (m, 1H, H6), 1.41 (s, 3H, $CH_3$ 16), 1.66 (dd, J=4.6, 12.8 Hz, 1H, H9β), 1.77 (d, J=1.4 Hz, 3H, $CH_3$ 18), 1.83 (dd, J=6.0, 14.7 Hz, 1H, H14α), 1.97 (dd, J=4.1, 8.5 Hz, 1H, H1), 2.02 (m, 2H, H5, H5), 2.44 (dd, J=11.9, 11.9 Hz, 1H, H9α), 2.75 (d, J=10.5 Hz, 1H, OH-2), 4.14 (q, J=14.2 Hz, 2H, OEt $CH_2$), 4.35 (dd, J=6.0, 8.7 Hz, 1H, H13), 4.42 (dd, J=4.6, 11.0 Hz, 1H, H10), 4.49 (dd, J=4.1, 10.1 Hz, 1H, H2), 4.86 (dd, J=1.8, 10.3 Hz, 1H, H20), 4.92 (dd, J=1.8, 16.9 Hz, 1H, H20), 5.23 (dd, J=1.4, 10.1 Hz, 1H, H7), 5.67 (dddd, J=6.9, 6.9, 10.5, 16.9 Hz, 1H, H4); $^{13}$C NMR δ (ppm) −5.3 (TBS $CH_3$), −4.5 (TBS $CH_3$), 4.7 (TES $CH_2$), 6.5 (TES $CH_3$), 14.0 (OEt $CH_3$), 15.0 ($CH_3$ 19), 16.0 ($CH_3$ 18), 18.0 (TBS $\underline{C}(CH_3)_3$), 25.8 (TBS C($\underline{CH}_3$)$_3$), 27.5, 27.8 ($CH_3$ 17), 28.1 ($CH_3$ 16), 30.4, 30.5 (C5, C6), 36.9 (C15), 47.3 (C9), 54.5 (C1), 54.7 (C8), 63.9 (OEt $CH_2$), 66.2 (C13), 67.8 (C10), 70.3 (C2), 83.6 (C7), 114.9 (C20), 135.4 (C11), 137.9 (C4'), 144.5 (C12), 155.6 (Ethylcarbonate C=O), 217.8 (C3); IR ($CCl_4$) ν 3600, 2950, 2900, 1750, 1700, 1660, 1470, 1400, 1370, 1240, 1080, 1050, 1000, 840, 680 cm$^{-1}$; MS (CI) 653 (M+1, 8), 564 (100), 431 (69), 389 (67).

Hydroxycarbonate 8. To a vigorously stirred solution of hydroxyketone 7 ($P_{10}$=TES, $P_{13}$=TBS, R=Et) (2.69 g, 4.12 mmol) in toluene (117 mL) under nitrogen at −78° C. was added dropwise down the side of the flask 85 mL of a 0.97 M solution (82.4 mmol) of RedAl in toluene. After 6 h at −78° C., the solution was allowed to gradually warm to room temperature over a period of 6 h. The mixture was recooled to −10° C. and 125 mL of a 2 M solution (250 mmol) of acetic acid in THF was added dropwise down the side of the flask. The cloudy mixture was stirred 10 min then poured into 120 mL of 50% ethyl acetate in hexanes and washed with 1 L of a saturated aqueous $NaHCO_3$ solution. The aqueous phase was extracted with four 500 mL portions of ethyl acetate and the combined organic phases were washed with brine, dried over anhydrous $Na_2SO_4$ and concentrated under reduced pressure to yield 2.29 g of 2,3,7-triol as a white solid. This material was used without further purification.

To a vigorously stirred solution of triol (2.29 g. 3.93 mmol) in $CH_2Cl_2$ (157 mL) and pyridine (15.7 mL) under nitrogen at −78 ° C. was quickly added 7.6 mL of a 3.0 M solution (23 mmol) of phosgene in toluene. The solution was allowed to warm to room temperature over a period of 1 h then poured into 250 mL of ethyl acetate, washed with two 125 mL portions of a saturated aqueous $NaHCO_3$ solution and 100 mL brine, dried over anhydrous $Na_2SO_4$ and concentrated under reduced pressure to yield 2.52 g yellow oil. This material was filtered through a 2 inch pad of silica gel with 50% ethyl acetate in hexanes and concentration under reduced pressure yielded 2.39 g (95% from 7) of hydroxy carbonate 8 ($P_{10}$=TES, $P_{13}$=TBS) as a white solid.

8 ($P_{10}$=TES, $P_{13}$=TBS): mp 155–157° C.; $^1$H NMR (500 MHz, $CDCl_3$) δ 0.09 (s, 3H, TBS $CH_3$), 0.10 (s, 3H, TBS $CH_3$), 0.59 (q, J=8.2 Hz, 6H, TES $CH_2$), 0.96 (t, J=8.2 Hz, 9H, TES $CH_3$), 0.97 (s, 9H, TBS t-Bu), 1.11 (s, 3H, $CH_3$ 19), 1.14 (s, 3H, $CH_3$ 17), 1.30 (s, 3H, $CH_3$ 16), 1.39 (dd, J=4.1, 13.3 Hz, 1H, H9β), 1.65 (m, 2H, H6, H6), 1.99 (dd, J=6.4, 15.1 Hz, 1H, H14α), 2.01 (d, J=0.9 Hz, 3H, $CH_3$ 18), 2.04 (d, J=3.7 Hz, 1H, H1), 2.11 (ddd, J=7.8, 15.6, 15.6 Hz, 1H, H5), 2.28 (ddd, J=9.6, 9.6, 14.2 Hz, 1H, H14β), 2.34 (dd, J=12.4, 13.3 Hz, 1H, H9β), 2.41 (m, 1H, H5), 3.87 (dd, J=0.9, 10.5 Hz, 1H, H7), 3.95 (d, J=3.7 Hz, 1H, H2), 4.59 (dd, J=3.7, 11.4 Hz, 1H, H10β), 4.40 (s, 1H, H3), 4.55 (dd, J=6.4, 8.7 Hz, 1H, H13), 5.03 (d, J=10.5 Hz, 1H, H20), 5.07 (dd, J=1.5, 17.0 Hz, 1H, H20), 5.77 (m, 1H, H4); $^{13}$C NMR δ (ppm) −5.4 (TBS $CH_3$), −4.4 (TBS $CH_3$), 4.8 (TES $CH_2$), 6.5 (TES $CH_3$), 15.5 ($CH_3$ 18), 17.9 (TBS $\underline{C}(CH_3)_3$), 18.2 ($CH_3$ 19), 25.6 (TBS C($\underline{CH}_3$)$_3$), 25.9 ($CH_3$ 16), 27.5 ($CH_3$ 17), 28.3 (C6), 28.4 (C5), 29.8 (C14), 30.8 (C15), 36.5 (C8), 36.8 (C9), 37.3, 50.8 (C1), 66.6 (C10), 67.8 (C13), 70.5 (C2), 91.9 (C3), 91.9 (C7), 116.3 (C20), 133.7 (C11), 137.9 (C4'), 142.6 (C12), 148.0 (cyclic carbonate C=O); IR ($CCl_4$) ν 3450, 2950, 2870, 1750, 1460, 1380, 1350, 1220, 1120, 1080, 1040, 980, 900, 820, 710 cm$^{-1}$; MS (CI) 625 (M+1-$H_2O$, 6), 551 (11), 477 (100), 459 (12), 433 (8), 344 (90); Anal. Calcd. for $C_{33}H_{60}O_6Si_2$: C, 64.92; H, 9.90; Found: C, 65.13; H, 9.88.

Ketocarbonate 9. To a vigorously stirred solution of dimethylsulfoxide (2.41 mL, 34 mmol) in $CH_2Cl_2$ (57 mL) under nitrogen at −78° C. was added 8.5 mL of a 2.0 M solution (17.0 mmol) of oxalyl chloride in $CH_2Cl_2$. After 10 min, a solution of hyroxycarbonate 8 ($P_{10}$=TES, $P_{13}$=TBS) (3.45 g, 5.67 mmol) in 16 mL $CH_2Cl_2$ was added dropwise down the side of the flask. After 30 min at −78° C., tiethylamine (6.8 mL, 49 mmol) was added and the mixture was warmed to room temperature. The mxture was diluted with 200 mL hexanes, washed with two 75 mL portions of a saturated aqueous $NaHCO_3$ solution and brine, dried over anhydrous $Na_2SO_4$ and concentrated under reduced pressure to yield 3.45 g of a yellow solid. This material was filtered though a 1 inch pad of silica gel with 10% ethyl acetate in hexanes and then recrystallized from hexanes to yield 2.62 g of ketocarbonate 9 as white crystals. The mother liquor was purified by silica gel chromatography, eluting with 10% ethyl acetate in hexanes and then recrystallization from hexanes to yield an additional 0.58 g of ketocarbonate 9 ($P_{10}$=TES, $P_{13}$=TBS) (total yield: 3.20 g, 93%).

9 ($P_{10}$=TES, $P_{13}$=TBS): mp 140.0–141.5° C.; $^1$H NMR (500 MHz, $CDCl_3$) δ 0.11 (s, 3H, TES $CH_3$), 0.12 (s, 3H, TES $CH_3$), 0.60 (q, J=7.8 Hz, 6H, TES $CH_2$), 0.96 (t, J=7.8 Hz, 9H, TES $CH_3$), 0.98 (s, 9H, TBS t-Bu), 1.06 (s, 3H, $CH_3$ 19), 1.17 (s, 6H, $CH_3$ 16, $CH_3$ 19), 1.42 (dd, J=3.7, 14.2 Hz, 1H, H9β), 1.63 (m, 2H, H6, H6), 2.12 (m, 1H, H5), 2.38 (d, J=0.9 Hz, 3H, $CH_3$ 18), 2.47 (dd, J=11.4, 13.3 Hz, 1H, H9α), 2.65 (d, J=8.2, 1H, H1), 3.94 (dd, J=1.4, 10.4 Hz, 1H, H7), 4.44 (dd, J=3.7, 11.4 Hz, 1H, H10), 4.49 (s, 1H, H3), 4.64 (dd, J=6.9, 7.8 Hz, 1H, H13), 5.04 (dd, J=1.4, 11.9 Hz, 1H, H20), 5.07 (dd, J=1.8, 17.4 Hz, 1H, H20), 5.76 (m, 1H, H4); $^{13}$C NMR δ (ppm) –5.4 (TBS $CH_3$), –4.5 (TES $CH_3$), 4.8 (TES $CH_2$), 6.5 (TES $CH_3$), 15.7 ($CH_3$ 18), 17.8 ($CH_3$ 19), 17.9 (TBS $\underline{C}(CH_3)_3$), 25.5 (TBS C($\underline{CH}_3)_3$), 28.2 ($CH_3$ 16), 28.3 ($CH_3$ 17), 28.3 (C6), 29.6 (C5), 30.4 (C14), 37.7 (C15), 38.0 (C8, C9), 62.1(C1), 66.5 (C10), 67.5 (C13), 91.3(C3), 91.5(C7), 116.4(C20), 132.8 (C11), 137.0 (C4'), 145.4 (C12), 146.6 (cyclic carbonate C=O), 206.8 (C2); IR ($CCl_4$) ν 2930, 2860, 1760, 1670, 1450, 1380, 1340, 1240, 1180, 1170, 1120, 1090, 1060, 1040, 980, 890, 860, 820, 700, 650 $cm^{-1}$; MS (CI) 607 (M+1, 6), 549 (11), 475 (100), 431 (4), 347 (45); Anal. Calcd. for $C_{33}H_{58}O_6Si_2$: C, 65.30; H, 9.63; Found: C, 65.23; H, 9.66.

2-Keto-3-Hydroxy-Lactone 10. To a strred solution of 3,7-cyclic carbonate 9 ($P_{10}$=TES, $P_{13}$=TBS) (2.246 g, 3.70 mmol) in THF (9 mL) was added 19.4 mL of 0.2 M LTMP (3.88 mmol) in THF dropwise down the sides of the flask at –25° C. The reaction mixture was allowed to warm to –10° C. over the course of 30 min. The cold reaction mixture was poured into 100 mL of 10% aqueous acetic acid and extracted with 100 mL of 10% ethyl acetate in hexanes. The organic phase was washed with 50 mL of a saturated aqueoues $NaHCO_3$ solution and 50 mL of brine. The combined aqueous phases were extracted with two 20 mL portions of 10% ethyl acetate in hexanes. The oraganic phases were combined, dried over anhydrous $Na_2SO_4$ and concentrated under reduced pressure to give 2.4 g of a yellow oil. This material was purified by silica gel chromatography, eluting with 5% then 10% ethyl acetate in hexanes to yield 2.033 g (90%) of the hydroxy lactone 10 ($P_{10}$=TES, $P_{13}$=TBS) as a foamy solid and 0.207 g (7.2%) of the 3-carbamate.

10 ($P_{10}$=TES, $P_{13}$=TBS): $^1$H NMR (500 MHz, $CDCl_3$) δ 0.12 (s, 3H, TBS $CH_3$), 0.14 (s, 3H, TBS $CH_3$), 0.61 (q, J=7.8 Hz, 6H, TES $CH_2$), 0.92 (s, 9H, TBS t-Bu), 0.97 (t, J=7.8 Hz, 9H, TES $CH_3$), 1.11 (s, 3H, $CH_3$ 17), 1.22 (s, 3H, $CH_3$ 19), 1.27 (s, 3H, $CH_3$ 16), 1.32 (dd, J=3.2, 13.3 Hz, 1H, H9β), 1.64 (ddd, J=2.3, 6.9, 9.2 Hz, 1H, H6), 2.07 (m, 2H, H6, H5), 2.17 (m, 1H, H14α), 2.33 (m, 1H, H5), 2.65 (m, 2H, H14β, H1), 2.74 (dd, J=12.4, 12.4 Hz, 1H, H9α), 3.92 (dd, J=2.8, 11.5 Hz, 1H, H7), 4.47 (dd, J=3.2, 11.0 Hz, 1H, H10), 4.55 (dd, J=2.8, 9.6 Hz, 1H, H13), 5.02 (d, J=10.1 Hz, 1H, H20), 5.07 (dd, J=1.4, 16.9 Hz, 1H, H20), 5.81 (dddd, J=6.9, 6.9, 10.5, 16.9 Hz, 1H, H4); $^{13}$C NMR δ (ppm) –5.2 (TBS $CH_3$), –4.5 (TBS $CH_3$), 4.8 (TES $CH_2$), 6.6 (TES $CH_3$), 16.4 ($CH_3$ 18), 17.9 (TBS $\underline{C}(CH_3)_3$), 24.2 ($CH_3$ 19), 25.7 (TBS C($\underline{CH}_3)_3$), 26.9 ($CH_3$ 16), 30.1 ($CH_3$ 17), 30.4 (C5), 32.7 (C6), 32.9 (C14), 39.1 (C15), 40.6 (C9), 48.1 (C8), 62.0 (C1), 67.3 (C10), 67.6 (C13), 87.9 (C3), 91.1 (C7), 115.8 (C20), 137.7 (C11), 138.5 (C4'), 143.0 (C12), 173.5 (C4), 207.6 (C2); IR ($CCl_4$) ν 3500, 2970, 2900, 1780, 1700, 1480, 1360, 1260, 1210, 1160, 1070, 1010, 910, 890, 840 $cm^{-1}$; MS (EI) 606 (M, 100), 549 (69), 474 (27), 431 (65), 417 (40); Anal. Calcd. for $C_{33}H_{58}O_6Si_2$: C, 65.30; H, 9.63; Found: C, 65.38; H, 9.64.

Keto Lactone 11. To the 2-keto-3-hydroxylactone 10 ($P_{10}$=TES, $P_{13}$=TES) (1.10 g, 1.83 mmol) was added a 0.1 M solution of $SmI_2$ in THF (82 mL, 8.2 mmol). The resulting dark blue solution was stirred at room temperature under $N_2$ for 4 h. After cooling to 0° C. an ethereal solution of HCl (0.66M; 4.2 mL, 2.77 mmol) was added; after 5 min the flask was opened to the air and the reaction mixture was diluted with 200 mL of cold ethyl acetate₉ then poured into 50 mL of ice cold 0.2N aqueous HCl. The organic phase was separated and washed with 50 mL of a 5% aqueous citric acid solution, two 50 mL portions of a saturated aqueous $NaHCO_3$ solution and 50 mL of brine, dried over anhydrous $Na_2SO_4$ and concentrated under reduced pressure. The resulting material was dissolved in 100 mL of hexanes, then silica gel (230–400 mesh; 4.3 g) was added and the mixture was vigorously stirred at room temperature for 65 min before filtering through a 1 inch pad of silica gel eluting with 300 mL of 20% ethyl acetate in hexanes. The solvent was evaporated under reduced pressure and the residue was purified by silica gel chromatography, eluting with 10% ethyl acetate in hexanes to yield 822 mg (77%) of the cis-ketolactone 11 and 164 mg (15%) of the corresponding trans isomer.

To a solution of the trans-2-ketolactone (611 mg, 1.03 mmol) stirred in 10 mL of THF under nitrogen at 0° C. was added down the side of the flask 6.8 mL of a 0.6 M solution (4.1 mmol) of t-BuOK in THF. The resulting solution was stirred for 1.5 h then 10 mL of a 10% acetic acid solution in THF was added down the side of the flask. After stirring for 5 min the mixture was diluted with 200 mL of hexanes and poured into 100 mL of a saturated aqueous $NaHCO_3$ solution. The organic layer was washed with water and brine then dried over anhydrous $Na_2SO_4$ and concentrated under reduced pressure to yield 615 mg of pale brown oil. The oil was dissolved in 10 mL of hexanes and silica gel (3.0 g) was added. The mixture was stirred vigorously for 15 min then filtered through a ½ in plug of silica gel with 20% ethyl acetate in hexanes. Concentration of the filtrate under reduced pressure yielded 576 mg of pale yellow oil. This material was purified by silica gel chromatography, eluting with 10% then 20% ethyl acetate in hexanes to yield 472 mg (77%) of pure cis-2-ketolactone 11 ($P_{10}$=TES, $P_{13}$=TBS), 84 mg (13%) of pure trans isomer and 24 mg of a 6:1 mixture of cis:trans isomers.

11 ($P_{10}$=TES, $P_{13}$=TBS): mp=86.5–88.0° C.; $^1$H NMR (500 MHz, $CDCl_3$) δ 0.05 (s, 3H, TBS $CH_3$), 0.07 (s, 3H, TBS $CH_3$), 0.54 (q, J=7.8 Hz, 6H, TES $CH_2$), 0.84 (s, 9H, TBS t-Bu), 0.90 (t, J=7.8 Hz, 9H, TES $CH_3$), 1.03 (s, 3H, $CH_3$ 17), 1.11 (s, 3H, $CH_3$ 16), 1.15 (s, 3H, $CH_3$ 19), 1.35 (dddd, J=4.6, 4.6, 7.3, 14.2 Hz, 1H, H6), 1.43 (dd, J=3.7, 12.8 Hz, 1H, H9β), 1.67 (dddd, J=3.2, 7.3, 10.1, 13.7 Hz, 1H, H6), 1.83 (dd, J=4.6, 16.0 Hz, 1H, H14α), 2.03 (m, 1H, H5), 2.07 (d, J=1.4 Hz, 3H, $CH_3$ 18), 2.25 (m, 1H, H5), 2.30 (dd, J=11.9, 12.3 Hz, 1H, H9α), 2.45 (d, J=8.2 Hz, 1H, H1), 2.58 (ddd, J=8.7, 9.2, 16.0 Hz, 1H, H14β), 3.93 (dd, J=2.8, 11.4 Hz, 1H H7β), 4.03 (s, 1H, H3α), 4.37 (dd, J=3.7, 11.0 Hz, 1H, H10β), 4.46 (ddd, J=1.4, 4.6, 9.2 Hz, 1H, H13β), 4.96 (dd, J=1.4, 10.1 Hz, 1H, H20), 5.01 (dd, J=1.4, 17.4 Hz, 1H, H20), 5.73 (dddd, J=6.4, 7.3, 10.5, 16.9 Hz, 1H, H4); $^{13}$C NMR δ (ppm) –5.3 (TBS $CH_3$), –4.6 (TBS $CH_3$), 4.5 (TES $CH_2$), 6.5 (TES $CH_3$), 15.0 ($CH_3$ 18), 18.0 (TBS $\underline{C}(CH_3)_3$), 25.7 (TBS C($\underline{CH}_3)_3$), 28.9 ($CH_3$ 19), 29.2 ($CH_3$ 16), 29.8 (C5), 29.9 ($CH_3$ 17), 30.3 (C6), 32.8 (C14), 38.5 (C15), 44.2 (C8), 44.9 (C9), 60.6 (C3), 61.2 (C1), 66.9 (C10), 67.8 (C13), 91.9 (C7), 115.7 (C20), 137.7 (C11), 138.5 (C4'), 142.4 (C12), 174.7 (C4), 204.8 (C2); IR ($CCl_4$) ν 2975, 2899, 1780, 1705, 1460, 1355, 1260, 1180, 1070, 1060, 1000, 830 cm$^{-1}$; MS (CI) 591 (M+1, 5), 523 (6), 459 (100), 441 (5); Anal. Calcd. for $C_{33}H_{58}O_5Si_2$: C, 66.07; H, 9.89; Found: C, 66.97; H, 9.91.

1-Hydroxy-2-Keto-Lactone 12. To 34.2 mL of a stirred 0.2 M solution (6.84 mmnol) of LTMP in THF under nitrogen at −10° C. was added a solution of ketolactone 11 ($P_{10}$=TES, $P_{13}$=TBS) (1.008 g, 1.71 mmol) in 10 mL of THF dropwise down the side of the flask. After 0.5 h, the reaction mixture was cooled to −40° C. and a solution of (+)-camphorsulfonyl oxaziridine (1.96 g, 8.55 mmol) in THF (10 mL) was added dropwise down the side of the flask. After 20 min, the reaction mixture was cooled to −78° C., diluted with 200 mL of hexanes and rapidly poured into 250 mL of a vigorously stirred saturated aqueous $NH_4Cl$ solution. The aqueous phase was extracted with two 50 mL portions of hexane and the combined organic phase were dried over anhydrous $Na_2SO_4$ and concetrated under reduced pressure to give 1.4 g of a waxy solid. This material was chromatographed ($CH_2Cl_2$ followed by hexanes increasing to 10% ethyl acetate in hexanes) to give 0.882 g of hydroxyketolactone 12 ($P_{10}$=TES, $P_{13}$=TBS) (85%) as a white solid, 0.083 g of the corresponding trans-hydroxyketolactone (8%) as a solid, and 31 mg of returned ketolactone 11 (3%).

12 ($P_{10}$=TES, $P_{13}$=TBS): mp 124–126° C.; 1H NMR ($C_6D_6$) δ (ppm) 0.09 (s, 3H, $CH_3$ in TBDMS), 0.17 (s, 3H, $CH_3$ in TBDMS), 0.62 (q, J=7.78 Hz, 6H $CH_2$'s in TES), 1.03 (t, J=7.78, 9H $CH_3$'s in TES), 1.05 (s, 3H, $CH_3$19), 1.13 (s, 9H, t-Bu in TBS), 1.20 (s, 3H, $CH_3$17), 1.39 (m, 1H, H6), 1.42 (s, 3H, $CH_3$16), 1.44 (dd, J=0.92, 13.28 Hz, 1H, H9β), 1.98 (dd, J=9.61, 12.82 Hz, 1H, H14β), 2.05 (m, 1H, H5), 2.06 (broad, 1H, OH1, $D_2O$ exchangable), 2.25 (m, 1H, H6), 2.27 (d, J=0.91 Hz, 3H, $CH_3$18), 2.29 (m, 1H, H5), 2.41 (dd, J=10.98, 13.28 Hz, 1H, H9α) 2.56 (dd, J=3.21, 12.82 Hz, 1H, H14α), 3.83 (dd, J=2.75, 11.90 Hz, 1H, H7), 4.04 (s, 1H, H3), 4.47 (dd, J=0.92, 10.98 Hz, 1H, H10), 4.60 (ddq, J=0.91, 3.21, 9.61 Hz, 1H, H13), 5.11 (br d, J=10.53 Hz, 1H, H20), 5.18 (br d, J=17.40 Hz, 1H, H20), 5.77 (m, 1H, H4); 13C NMR ($CDCl_3$) δ (ppm) −5.4 (TBS $CH_3$), −4.7 TBS $CH_3$), 4.5 (TES $CH_2$), 6.5 (TES $CH_3$), 15.5 ($CH_3$ 18), 17.9 (TBS $\underline{C}(CH_3)_3$), 22.5 ($CH_3$ 19), 25.7 (TBS C($\underline{CH}_3$)$_3$), 26.3 ($CH_3$ 16), 29.8 ($CH_3$ 17), 29.8 (C5), 30.4 (C6), 39.6 (C14), 41.3 (C15), 44.5 (C9), 45.0 (C8), 58.1 (C3), 66.5 (C10), 68.2 (C13), 83.0 (C1), 91.7 (C7), 115.7 (C20), 137.0 (C11), 137.6 (C4'), 145.5 (C12), 175.0 (C4), 202.4 (C2); IR ($CCl_4$) ν 3500, 3000, 1780, 1720, 1100 cm$^{-1}$; MS (CI) 607 (M+1, 10), 589 (56), 475 (100), 457 (61); Anal. Calcd for $C_{33}H_{58}O_6Si_2$: C, 65.30; H, 9.63. Found: C, 65.19; H, 9.60.

1,2-Dihydroxy-trans-lactone 13. To a stirred 1.23 M solution of Red-Al (4.6 mmol, 5.6 mmol) in THF under nitrogen at −78° C. was quickly added a solution of cis-hydroxyketone 12 ($P_{10}$=TES, $P_{13}$=TBS) (342 mg, 0.563 mmol) in THF (25 mL). After 1.5 h, 25 mL of a 15% aqueous NaOH solution was added dropwise directly to the reaction mixture. The reaction mixture was vigorously stirred at room temperature for 3 h and was then poured into 100 mL of $H_2O$ and extracted with two 100 mL portions of ether. The organic phases were combined and washed with 100 mL of $H_2O$ and 100 mL of brine, dried over anhydrous $Na_2SO_4$ and concentrated under reduced pressure to give 0.35 g of a pale yellow solid. This material was purified by silica gel chromatography eluting with 10% ether in hexanes followed by 25% ethyl acetate in hexanes to yield 290 mg trans-diol 13 as colorless needles, 14.5 mg (4.2%) of trans-hydroxyketone, and 20 mg of a mixture of cis-diol and unknown byproducts. To a solution of the mixture containing cis-diol in THF (1 mL) under nitrogen at room temperature was added 0.5 mL a 30% aqueous solution of NaOH. After 2.5 h, the reaction mixture was poured into 30 mL of $H_2O$ and extracted with 30 mL of ether. The organic phase was washed with 30 mL of $H_2O$ and 30 mL of brine, dried over anhydrous $Na_2SO_4$ and concentrated under reduced pressure to give 0.02 g of a yellow solid, which was purified by silica gel chromatography eluaing with 5% ethyl acetate in hexanes to yield an additional 12 mg (total yield: 302 mg, 88%) of trans-diol 13 ($P_{10}$=TES, $P_{13}$=TBS).

13 ($P_{10}$=TES, $P_{13}$=TBS): mp 127–128° C., $^1$H NMR (500 MHz, $CDCl_3$) δ 0.09 (s, 3H, TBS $CH_3$), 0.11 (s, 3H, TBS $CH_3$), 0.60 (q, J=8.1 Hz, 6H, TES $CH_2$), 0.87 (s, 9H, TBS $CH_3$), 0.96 (t, J=8.1 Hz, 9H, TES $CH_3$) 1.13 (s, 3H, $CH_3$ 17), 1.23 (s, 3H, $CH_3$ 16), 1.31 (s, 3H, $CH_3$ 19), 1.42 (dd, J=3.7, 12.8 Hz, 1H, H9β), 1.46 (ddd, J=4.8, 8.8, 11.4 Hz, 1H, H6), 1.74 (dddd, J=3.3, 7.3, 9.9, 12.4 Hz, 1H, H6), 1.99 (d, J=1.5 Hz, 3H, $CH_3$ 18), 2.10 (m, 1H, H5), 2.21 (dd, J=3.7, 5.4 Hz, 1H, H14α), 2.26 (m, 3H, H5, H9α, H14β), 2.92 (d, J=7.7 Hz, 1H, H3), 3.84 (dd, J=2.2, 7.7 Hz, 1H, H2), 3.85 (s, 1H, OH1), 3.97 (dd, J=2.9, 11.4 Hz, 1H, H7), 4.47 (dd, J=3.7, 11.4 Hz, 2H, H13, H10), 5.01 (dd, J=1.8, 12.2 Hz, 1H, H20), 5.07 (dd, J=1.7, 17.0 Hz, 1H, H20), 5.78 (dddd, J=7.3, 7.3, 10.1, 16.5 Hz, 1H, H4), 6.87 (d, J=2.9 Hz, 1H, OH2), $^{13}$C NMR ($CDCl_3$) δ (ppm) −5.31, −4.59, 4.79, 6.55, 16.60, 17.68, 21.24, 24.70, 25.62, 28.50, 29.52, 30.05, 40.20, 40.41, 44.18, 45.18, 45.60, 66.62, 69.25, 71.32, 88.91, 116.09, 136.96, 138.63, 139.93, 180.10, IR ($CHCl_3$) ν 3050, 1730, 1460, 1350 cm$^{-1}$, MS (EI) 608 (M, 13), 590 (26), 267 (100), Anal. Calcd. for $C_{33}H_{60}O_6Si_2$: C, 65.08; H, 9.92. Found C, 65.06; H, 9.98.

Carbonate 14. To a stirred solution of diol 13 ($P_{10}$=TES, $P_{13}$=TBS) (1.00 g, 1.64 mmol) in $CH_2Cl_2$ (58 mL) and pyridine (5.8 mL) under nitrogen at −78° C. was added dropwise 8.2 mL of 2 M solution (16.4 mmol) of phosgene in toluene. Then the reaction mixure was warmed to −23° C. and stirred for 30 min. To the resulting mixture, 50 mL of a saturated aqueous $NaHCO_3$ solution was added. After warming to room temperature for 10 min, the reaction mixture was extracted with 200 mL of 10% ethyl acetate in hexanes. The organic phase was washed with 100 mL of a 10% aqueous $CuSO_4$ solution, two 200 mL portions of a saturated aqueous $NaHCO_3$ solution and brine, dried over anhydrous $Na_2SO_4$ and concentrated under reduced pressure to give 1.1 g of a pale yellow solid. This material was filtered through a 3 inch pad of silica gel with 15% ethyl acetate in hexanes to yield 1.045 g (100%) of carbonate 14 ($P_{10}$=TES, $P_{13}$=TBS) as a white solid.

14 ($P_{10}$=TES, $P_{13}$=TBS): mp 146–147° C., $^1$H NMR (500 MHz, $CDCl_3$) δ 0.11 (s, 3H, TBS $CH_3$), 0.12 (s, 3H, TBS $CH_3$), 0.61 (q, J=7.8 Hz, 6H, TES $CH_2$), 0.88 (s, 9H, TBS t-Bu), 0.96 (t, J=7.8 Hz, 9H TES $CH_3$), 1.20 (s, 3H, $CH_3$ 17), 1.30 (s, 3H, $CH_3$ 16), 1.32 (s, 3H, $CH_3$ 19), 1.40 (ddd, J=2.7, 4.5, 9.2 Hz, 1H, H6), 1.44 (d, J=3.7, 13.3 Hz, 1H, H9β), 1.71 (dddd, J=2.7, 6.9, 9.6, 12.8 Hz, 1H, H6), 2.11 (ddd, J=7.8, 15.3, 15.3 Hz, 1H, H5), 2.29 (dd, J=3.2, 15.6 Hz, 1H, H14α), 2.31 (m, 2H, H5, H9α), 2.59 (dd, J=9.2, 15.6 Hz, 1H, H14β), 2.99 (d, J=7.3 Hz, 1H, H3α), 4.02 (dd, J=2.7, 11.4 Hz, 1H, H7β), 4.38 (dd, J=3.7, 11.0 Hz, 1H, H10β), 4.47 (d, J=7.3 Hz, 1H, H2β), 4.57 (dd, J=2.1, 9.2 Hz, 1H, H13β), 5.02 (dd, J=1.4, 10.1 Hz, 1H, H20), 5.06 (dd, J=1.4, 16.9 Hz, 1H, H20), 5.77 (dddd, J=6.9, 6.9, 10.1, 17.0 Hz, 1H, H4), $^{13}$C NMR ($CDCl_3$) δ (ppm) −5.37, −4.60, 4.75, 6.51, 17.02, 17.60, 21.24, 24.64, 25.55, 27.36, 29.50, 30.11, 37.56, 39.96, 42.89, 43.75, 45.39, 66.54, 68.29, 87.37, 90.05, 116.15, 136.54, 136.94, 144.93, 153.32, 169.89, IR ($CHCl_3$) ν3070, 1800 cm$^{-1}$, MS (EI) 634 (M, 12), 577 (100), Anal. Calcd. for $C_{34}H_{58}O_7Si_2$: C, 64.31; H, 9.21. Found C, 64.41; H, 9.22.

Ketoester 15. To a stirred solution of lactone 14 ($P_{10}$=TES, $P_{13}$=TBS) (1.05 g, 1.65 mmol) in methanol (70 mL) under nitrogen at −78° C. was added a saturated solution of ozone in methylene chloride (50 mL, 40 mL then 8 mL) until no more starting material remained by TLC analysis. Triethylamine (4.8 mL) and trimethylphosphite (3.1 mL) were added sequentially to the resulting mixture at −78° C. After stirring 5 min, the solution was warmed to 0° C. and stirred for 2 h. The resulting solution was poured into 250 mL of a saturated aqueous $NaHCO_3$ solution and extacted with three 200 mL portions of $CH_2Cl_2$. The combined organic layers were washed with 150 mL of a saturated $NaHCO_3$ solution, dried over anhydrous $Na_2SO_4$ and concentrated under reduced pressure to give 1.10 g of the aldehyde as a colorless oil. This material was used further purification.

To a stirred solution of the aldehyde (1.10 g) in t-butanol (30.8 mL), acetone (10.3 mL) and 8 mL of a 1.25 M (10 mmol) aqueous $KH_2PO_4$ solution at 0° C. was added 11.3 mL of a 1 M (11.3 mmol) aqueous $KMnO_4$ solution over the course of 2 min. The reaction mixture was stirred at 0° C. for 30 min, poured into 200 mL of a 10% aqueous $Na_2S_2O_3$ solution and extracted with three 200 mL portions of ethyl acetate. The combined organic layers were washed with 50 mL of water, dried over anhydrous $Na_2SO_4$ and concentrated under reduced pressure. To a stirred solution of the oily residue in ether (30 mL) at room temperature was added an ethereal solution of $CH_2N_2$ (20 mL). The solution was concentrated under reduced pressure to give 1.15 g of a colorless oil. This material was filtered through a 2 inch pad of silica gel with 40% ethyl acetate in hexanes and concentration under reduced pressure yielded 1.01 g (91%) of lactone ester 15 ($P_{10}$=TES, $P_{13}$=TBS, R=Me).

15 ($P_{10}$=TES, $P_{13}$=TBS, R=Me): $^1H$ NMR (500 MHz, $CDCl_3$) δ 0.12 (s, 3H, TBS $CH_3$), 0.12 (s. 3H, TBS $CH_3$), 0.60 (q, J=8.1 Hz, 6H, TES $CH_2$), 0.88 (s, 9H, TBS t-Bu), 0.96 (t. J=8.1 Hz, 9H, TES $CH_3$), 1.21 (s, 3H, $CH_3$), 1.30 (s, 3H, $CH_3$), 1.33 (s, 3H, $CH_3$), 1.51 (dd, J=3.7, 13.2 Hz, 1H, H9β), 1.53 (m, 1H, H6), 2.06 (d, J=1.1 Hz, 3H, $CH_3$ 18), 2.07 (ddd, J=2.9, 7.7, 21.6 Hz, 1H, H6), 2.29 (dd, J=3.7, 15.8 Hz, 1H, H14α), 2.31 (dd, J=13.2, 13.2 Hz, 1H, H9α), 2.46 (ddd, J=7.7, 16.8, 24.5 Hz, 1H, H5), 2.53 (ddd, J=5.5, 7.7, 16.8 Hz, 1H, H5), 2.60 (dd, J=9.2, 15.8 Hz, 1H, H14β), 2.99 (d, J=7.3 Hz, 1H, H3α), 3.68 (s, 3H, $CO_2Me$), 4.09 (dd, J=2.6, 12.1 Hz, 1H, H7β), 4.39 (dd, J=3.7, 11.0 Hz, 1H, H10β), 4.47 (d, J=7.3 Hz, 1H, H2β), 4.59 (dd, J=1.8, 9.2 Hz, 1H, H13β); Anal. Calcd. for $C_{34}H_{58}O_9Si_2$: C, 61.22; H, 8.77. Found C, 61.30; H, 8.79.

Enol ester 16. To a stirred solution of lactone ester 15 ($P_{10}$=TES, $P_{13}$=TBS, R=Me) (1.01 g, 1.51 mmol) in THF (24.5 mL) at −78° C. was added slowly a 19.4 mL of a 0.2 M solution (3.88 mmol) of LDA in THF down the side of the flask over the course of 3 min. After stirring 35 min, 10 mL of a 33% solution of acetic acid in THF was quickly added. After 5 min, the mixture was poured into 150 mL of a saturated aqueous $NaHCO_3$ solution and extracted with three 200 mL portions of $CHCl_3$. The combined organic phases were dried over anhydrous $Na_2SO_4$ and concentrated under reduced pressure to give 1.02 g of crude enol ester 16 ($P_{10}$=TES, $P_{13}$=TBS, R=Me) as a colorless oil. Approximately 3% of unreacted ester lactone 15 was still present but this material was used without further purification.

16 ($P_{10}$=TES, $P_{13}$=TBS, R=Me): $^1H$ NMR (300 MHz, $CDCl_3$) δ 0.09 (s, 3H, TBS $CH_3$), 0.10 (s, 3H, TBS $CH_3$), 0.61 (q, 6H, TES $CH_2$), 0.87 (s, 9H, TBS t-Bu), 0.96 (t, J=8.0 Hz, TES $CH_3$), 1.08 (s, 3H, $CH_3$), 1.21 (s, 3H, $CH_3$), 1.33 (S, 3H, $CH_3$), 1.61 (d, J=4.3 Hz, 1H, OH-7), 1.89 (dd, J=4.3, 13.9 Hz, 1H, H9α), 1.95 (dd, J=11.2, 11.2 Hz, 1H, H9β), 2.01 (d, J=1.1 Hz, 3H, $CH_3$ 18), 2.22 (ddd, J=2.7, 10.7, 15.5 Hz, 1H, H6β), 2.45 (dd, J=4.8, 15.5 Hz, 1H, H6α), 2.54 (dd, J=9.1, 15.0 Hz, 1H, H14β), 2.86 (dd, J=3.7, 15.0 Hz, 1H, H14α), 3.07 (s, 1H, H3α), 3.40 (ddd, J=4.8, 4.8, 9.6 Hz, 1H, H7α), 3.75 (s, 3H, $CO_2Me$ ), 4.39 (dd,J=4.3, 11.2 Hz, 1H, H10), 4.60 (d, J=4.3, 11.2 Hz, 1H, H2β), 4.67 (dd, J=2.1, 9.1 Hz, 1H, H13β), 12.24 (s, 1H, OH4).

Enol ester 17. To a stirred solution of crude enol ester 16 ($P_{10}$=TES, $P_{13}$=TBS, R=Me) (1.02 g) in THF (13 mL) and 2-methoxypropene (13 mL) under nitrogen at 0° C. was added 0.48 mL of a 0.1 M solution (0.048 mmol) of p-toluenesulfonic acid in THF. The mixture was stirred at 0° C. for 10 min and then triethylamine (0.66 mL) was added. The mixture was concentrated under reduced pressure and purified by silica gel chromatography, elutng with 7.5% ethyl acetate in hexanes increasing to 30% ethyl acetate in hexanes to yield 938 mg enol ester 17 ($P_7$=MOP, $P_{10}$=TES, $P_{13}$=TBS, R=Me) (84% from 15) and 30 mg (3%) of recovered lactone ester 15.

17 ($P_7$=MOP, $P_{10}$=TES, $P_{13}$ =TBS, R=Me): mp 95–97° C., $^1H$ NMR (300 MHz, $CDCl_3$) δ 0.08 (s, 3H, TBS $CH_3$), 0.10 (s, 3H, TBS $CH_3$), 0.59 (q, J=7.7 Hz, 6H, TES $CH_3$), 0.87 (s, 9H, TBS t-Bu), 0.95 (t, J=7.7 Hz, 9H, TES $CH_3$), 1.10 (s, 3H, $CH_3$), 1.19 (s, 3H, $CH_3$), 1.30 (s, 3H, $CH_3$), 1.34 (s, 3H, MOP $CH_3$), 1.37 (s, 3H, MOP $CH_3$), 1.84 (m, 2H, H9α), H9β), 1.98 (s, 3H, $CH_3$ 18), 2.17 (ddd, J=2.8, 10.4, 15.9 Hz, 1H, H6β), 2.52, (dd, J=9.3, 15.4 Hz, 1H, H14β), 2.63 (dd, J=4.4, 15.9 Hz, 1H, H6α), 2.88 (dd, J=3.8, 15.4 Hz, 1H, H14α), 3.06 (s, 1H, H3α), 3.26 (s, 3H, MOP OMe), 3.37 (dd, J=4.4, 10.4 Hz, 1H, H7α), 3.72 (s, 3H, $CO_2Me$), 4.36 (dd, J=6.0, 9.3 Hz, 1H, H10β), 4.57 (d, J=2.2 Hz, 1H, H2β), 4.67 (dd, J=2.8, 9.3 Hz, 1H, H13β), 12.24 (s, 1H, OH4).

Enol ester 17 ($P_7$=TES). To a solution of the enol ester 16 ($P_{10}$=TES, $P_{13}$=TBS, R=Me) (9 mg, 0.0137 mmole) and DMAP (3.5 mg, 0.0286 mmole) in pyridine (0.6 mL) at 0° C. was added triethylsilyl chloride (0.025 mL, 0.14 mmole). The solution was stirred at room temperature for 16 h, diluted with ethyl acetate (10 mL), poured into a saturated aqueous sodium bicarbonate solution (20 mL) and extracted with 20% ethyl acetate/hexane (20 mL×3). The combined organic layer was dried over anhydrous $NaSO_4$ filtered and concentrated to yield 25 mg of crude 17. Column chromatography (10% ethyl acetate/hexane) provided 10 mg (95%) of pure enol ester 17 ($P_7$=$P_{10}$=TES, $P_{13}$=TBS, R=Me).

17 ($P_7$=$P_{10}$=TES, $P_{13}$=TBS, R=Me): $^1H$ NMR (300 MHz, $CDCl_3$) δ 0.08 (s, 3H, TBS $CH_3$), 0.10 (s, 3H, TBS $CH_3$), 0.59 (q, J=8.1 Hz, 12H, TES $CH_2$), 0.87 (s, 9H, TBS t-Bu), 0.95 (t, J=7.7 Hz, 18H, TES $CH_3$), 1.05 (s, 3H, $CH_3$), 1.19 (s, 3H, $CH_3$), 1.30 (s, 3H, $CH_3$), 1.84 (m, 2H, H9α, H9β), 1.98 (s, 3H, $CH_3$ 18), 2.17 (ddd, J=2.8, 10.4, 15.9 Hz, 1H, H6β), 2.31 (dd, J=4,4, 15.9 Hz, 1H, H6α), 2.52, (dd, J=9.3, 15.4 Hz, 1H, H14β), 2.85 (dd, J=3.8, 15.4 Hz, 1H, H14α), 3.03 (br s, 1H, H3α), 3.34 (dd, J=5.0, 10.4 Hz, 1H, H7α), 3.75 (s, 3H, $CO_2Me$ OMe), 4.36 (dd, J=5.0, 10.4 Hz, 1H, H10β), 4.58 (d, J=2.7 Hz, 1H, H2β), 4.66 (br d, J=11.0 Hz, 1H, H13β), 12.22 (s, 1H, OH4).

Ketone 18. To a stirred solution of enol ester 17 ($P_7$=MOP, $P_{10}$=TES, $P_{13}$=TBS, R=Me) (963 mg, 1.3 mmol) in DMF (30 mL) under nitrogen at room temperature was added solid potassium thiophenoxide (250 mg, 1.69 mmol) followed by thiophenol (0.4 mL, 3.9 mmol). The solution was warmed to 86° C. for 3.5 hours. The solution was allowed to cool to room temperature then was poured directly into 250 mL of a saturated aqueous $NaHCO_3$ solution and extracted with three 150 mL portions of 30% ethyl acetate in hexanes. The combined organic phases were then filtered through a 2 inch silica gel pad and subsequently concentrated under reduced pressure to yield 1.29 g of crude product. This material was purified by radial chromatography, eluting with 15% then 20% and finally 25% ethyl acetate in hexanes to yield 763 mg (86%) of ketone 18 ($P_7$=MOP, $P_{10}$=TES, $P_{13}$=TBS).

18 ($P_7$=MOP, $P_{10}$=TES, $P_{13}$=TBS): $^1$H NMR (300 MHz, CDCl$_3$) δ 0.10 (s, 3H, TBS CH$_3$), 0.14 (s, 3H, TBS CH$_3$), 0.58 (q, J=8.2 Hz, 6H, TES CH$_2$), 0.94 (s, 9H, TBS t-Bu), 0.95 (t, J=8.2 Hz, 9H, TES CH$_3$), 1.22 (s, 3H, CH$_3$ 19), 1.30 (s, 3H, CH$_3$ 17), 1.32 (s, 6H, MOP CH$_3$), 1.33 (s, 3H, CH$_3$ 16), 1.80 (m, 1H, H5), 1.81 (dd, J=3.8, 3.8 Hz, 1H, H9β) 1.98 (m, 1H, H5), 1.99 (d, J=1.1 Hz, 3H, CH$_3$ 18), 2.21 (m, 1H, H6β), 2.29 (dd, J=10.4, 12.1 Hz, 1H, H9α), 2.43 (dd, J=9.3, 15.4 Hz, 1H, H14α), 2.53 (m, 1H, H6α), 2.63 (dd, J=5.0, 15.4 Hz, 1H, H14β) 2.70 (d, J=5.0 Hz, 1H, H3), 3.20 (s, 3H, MOP OMe), 3.39 (dd, J=6.1, 10.4 Hz, 1H, H7), 4.34 (dd, J=3.9, 10.4 Hz, 1H, H10), 4.55 (d, J=5.5 Hz, 1H, H2), 4.73 (dd, J=5.3, 7.7 Hz, 1H, H13). Anal. Calcd. for $C_{36}H_{64}O_8Si_2$: C, 63.49; H, 9.47. Found C, 63.56; H, 9.55.

18 ($P_7$=$P_{10}$=TES, $P_{13}$=TBS): $^1$H NMR (300 MHz, CDCl$_3$) δ 0.10 (s, 3H, TBS CH$_3$), 0.14 (s, 3H TBS CH$_3$), 0.47–0.63 (m, 12H, TES CH$_2$), 0.90–0.99 (m, 27H, TBS t-Bu, TES CH$_3$), 1.22 (s, 3H, CH$_3$), 1.25 (s, 3H, CH$_3$), 1.33 (s, 3H, CH$_3$), 1.75 (dt, J=11.6, 1.6 Hz, 1H), 1.85 (d, J=3.3 Hz, 1H), 1.90 (t, J=3.9 Hz, 1H), 1.97 (t, J=8.1 Hz, 1H), 2.00 (s, 3H, CH$_3$), 2.30 (m, 1H), 2.39–2.60 (m, 3H), 2.65 (m, 1H), 3.35 (dd, J=9.6, 7.8 Hz, 1H, H7α), 4.35 (dd, J=10.8, 3.3 Hz, 1H, H10β), 4.57 (d, J=5.1 Hz, 1H, H2β), 4.72 (m, 1H, H13β).

Ketone 18 ($P_7$=BOM). To a stirred solution of ketone 18 ($P_7$=MOP, $P_{10}$=TES, $P_{13}$=TBS) (293 mg, 0.43 mmol) in THF (28.6 mL) and methanol (9.5 mL) under nitrogen at room temperature was added dropwise 0.20 mL of a 0.1 M solution of PPTS in CH$_2$Cl$_2$ (0.02 mmol). The reaction mixture was stirred for 3 h, poured into 100 mL of a saturated aqueous NaHCO$_3$ solution and extracted with two 100 mL portions of ethyl acetate. The combined organic phases were washed with brine, dried over anhydrous Na$_2$SO$_4$ and concentrated under reduced pressure to yield 274 mg of the hydroxy ketone 18 ($P_7$=H) as a colorless oil. This material was used without further purification.

18 ($P_7$=H, $P_{10}$=TES, $P_{13}$=TBS): mp 75–77° C., $^1$H NMR (500 MHz, CDCl$_3$) δ 0.10 (s, 3H, TBS CH$_3$), 0.13 (s, 3H, TBS CH$_3$), 0.61 (q, J=8.2 Hz, 6H , TES CH$_2$), 0.93 (s, 9H, TBS t-Bu), 0.95 (t, J=7.7 Hz, 9H, TES CH$_3$), 1.19 (s, 3H, CH$_3$ 19), 1.22 (s, 3H, CH$_3$ 17), 1.35 (s, 3H, CH$_3$ 16), 1.84 (dd, J=13.7, 4.1 Hz, 1H, H9α), 1.88 (m, 2H, H9β, OH7), 1.92 (m, 1H, H6β), 2.05 (d, J=1.4 Hz, 3H, CH$_3$ 18), 2.10 (m, 1H, H6α), 2.36 (dddd, J=1.4, 4.1, 9.9, 14.4 Hz, 1H, H5α), 2.47 (dd, J=8.9, 15.4 Hz, 1H, H14β), 2.51 (m, 1H, H5β), 2.54 (dd, J=4.8, 15.4 Hz, 1H, H14β), 2.86 (d, J=5.5 Hz, 1H, H3), 3.59 (ddd, J=4.5, 6.2, 11.3 Hz, 1H, H7), 4.38 (dd, J=4.1, 9.1 Hz, 1H, H10), 4.56 (d, J=5.5 Hz, 1H, H2), 4.69 (ddd, J=1.4, 4.8, 9.3 Hz 1H, H13). Anal. Calcd. for $C_{32}H_{56}O_7Si_2$·5H$_2$O: C, 62.19; H, 9.30. Found C, 62.16; H, 9.22.

To a stirred solution of hydroxy ketone 18 ($P_7$=H) (179 mg, 0.29 mmol) in CH$_2$Cl$_2$ (9.5 mL), diisopropylethylamine (1.49 mL, 8.6 mmmol) and tetabutylammonium iodide (253 mg, 0.69 mmol) under nitrogen was added dropwise benzyloxymethylchloride (0.42 mL, 2.86 mmol). The reaction mixture was brought to reflux for 32 h, cooled to room temperature, poured into 100 mL of a satuated aqueous NaHCO$_3$ solution and extracted with two 100 mL portions of 50% ethyl acetate in hexanes. The combined organic phases were washed with brine, dried over anhydrous Na$_2$SO$_4$ and concentrated under reduced pressure to yield 249 mg of the hydroxy ketone as a yellowish oil. This material was purified by silica gel chromatography to yield 196 mg (92%) of ketone 18 ($P_7$=BOM, $P_{10}$=TES, $P_{13}$=TBS) as a colorless oil.

18 ($P_7$=BOM, $P_{10}$=TES, $P_{13}$=TBS): $^1$H NMR (500 MHz, CDCl$_3$) δ 0.10 (s, 3H, TBS CH$_3$), 0.13 (s, 3H, TBS CH$_3$), 0.59 (q, J=7.7 Hz, 6H, TES CH$_2$), 0.94 (s, 9H, TBS t-Bu), 0.94 (t, J=7.7 Hz, 9H, TES CH$_3$), 1.22 (s, 3H, CH$_3$ 17), 1.31 (s, 3H, CH$_3$ 19), 1.33 (s, 3H, CH$_3$ 16), 1.87 (dd, J=12.1, 3.8 Hz, 1H, H9α), 1.98 (d, J=1.4 Hz, 3H, CH$_3$ 18), 1.99 (m, 2H, H6β, H9β), 2.21 (m, 1H, H6α), 2.34 (dd, J=10.4, 12.1 Hz, 1H, H5α), 2.43 (dd, J=9.3, 15.4 Hz, 1H, H14α), 2.55 (ddd, J=5.5, 11.0, 13.7 Hz, 1H, H5β), 2.62 (dd, J=5.0, 15.4 Hz, 1H, H14β), 2.74 (d, J=5.0 Hz, 1H, H3), 3.38 (dd, J=6.6, 11 Hz, 1H, H7), 4.38 (dd, J=3.8, 10.4 Hz, 1H, H10), 4.56 (d, J=5.0 Hz, 1H, H2), 4.58 (d, J=11.5 Hz 1H, CH$_2$Ph), 4.64 (d, J=11.5 Hz 1H, CH$_2$Ph), 4.68 (m, 2H, H13, OCH$_2$O), 4.82 (d, J=7.2 Hz 1H, OCH$_2$O), 7.31 (m, 5H, Ph).

Ketone 22a ($P_5$=TMS). To a vigorously stirred solution of ketone 18 ($P_7$=BOM, $P_{10}$=TES, $P_{13}$=TBS) (315 mg, 0.42 mmol) in THF (10.5 mL), triethylamine (0.88 mL, 6.3 mmol) and trimethylsilyl chloride (0.53 mL, 4.2 mmol) under nitrogen at −78° C. was added dropwise down the side of the flask 1.35 mL of a 0.5 M solution (0.68 mmol) of LDA in THF. After 25 min, 2 mL of a saturated aqueous NaHCO$_3$ solution was added. The reaction mixture was diluted with 150 mL of hexanes and washed with 20 mL of a saturated aqueous NaHCO$_3$ solution and brine, dried over anhydrous Na$_2$SO$_4$ and concentrated under reduced pressure. The resulting oil was filtered through celite with hexanes and the filtrate was concentrated under reduced pressure to give 338 mg (99%) of the TMS enol ether 21a ($P_7$=BOM, $P_{10}$=TES, $P_{13}$=TBS, $P_4$=TMS) as a colorlessoil. To a vigorously stirred solution of TMS enolether 21a ($P_7$=BOM, $P_{10}$TES, $P_{13}$=TBS, $P_4$=TMS) (224 mg, 0.274 mmol) in hexanes (2.8 mL) under nitrogen at room temperature was added dropwise 14.9 mL of a 0.02 M solution (0.30 mmol) of MCPBA in hexanes. After 5 h, 2 mL of a saturated aqueous NaHCO$_3$ solution and 2 mL of a 10% aqueous Na$_2$S$_2$O$_3$ solution were added. The reaction mixture was diluted with 150 mL of ethyl acetate and washed with 20 mL of a saturated aqueous NaHCO$_3$ solution, 20 mL of a 10% aqueous Na$_2$S$_2$O$_3$ solution, 20 mL of a saturated aqueous NaHCO$_3$ solution and brine, dried over anhydrous Na$_2$SO$_4$ and concentrated under reduced pressure to give 231 mg of the crude material as a colorless oil. This material was used without further purification, or, alternatively, was purified by flash chromatography on silica gel to give 168 mg (74%) of 22a ($P_7$=BOM, $P_{10}$=TES, $P_{13}$=TBS, $P_5$=TMS) along with a mixture (15%) of 21a and 18 which could be recycled. 22a ($P_7$=BOM, $P_{10}$=TES, $_{13}$=TBS, $P_5$=TMS): mp 50.5–52° C., $^1$H NMR (500 MHz, CDCl$_3$) δ 0.10 (s, 3H, TBS CH$_3$), 0.13 (s, 9H, TMS CH$_3$), 0.14 (s, 3H, TBS CH$_3$), 0.59 (q, J=8.2 Hz, 6H, TES CH$_2$), 0.94 (s, 9H, TBS t-Bu), 0.94 (t, J=8.2 Hz, 9H, TES CH$_3$), 1.24 (s, 3H, CH$_3$ 17), 1.32 (s, 3H, CH$_3$ 19), 1.33 (s, 3H, CH$_3$ 16), 1.82 (dd, J=11.3, 13.7 Hz, 1H, H9α), 1.95 (d, J=1.4 Hz, 3H, CH$_3$ 18), 1.98 (dd, J=3.4, 13.7 Hz, 1H, H9β), 2.16 (ddd, J=6.2, 7.2, 13.3 Hz, 1H, H6α), 2.40 (dt, J=11.4, 13.3 Hz, 6β), 2.43 (dd, J=9.2, 15.2 Hz, 1H, H14β), 2.63 (dd, J=5.5, 15.2 Hz, 1H, H14α), 2.74 (d, J=5.5 Hz, 1H, H3α), 3.40 (dd, J=7.2, 10.6 Hz, 1H, H7α),4.36 (dd, J=3.4, 11.3 Hz, 1H, H10β), 4.40 (dd, J=6.2, 12.0 Hz, 1H, H5α), 4.54 (d, J=5.5 Hz, 1H, H2β), 4.57 (d, J=11.7 Hz 1H, CH$_2$Ph), 4.64 (d, J=11.7 Hz 1H, CH$_2$Ph), 4.68 (d, J=7.0 Hz 1H, OCH$_2$O), 4.74 (m, 1H, H13), 4.78 (d, J=7.0 Hz, 1H, OCH$_2$O), 7.31 (m, 5H, Ph). Anal. Calcd. for $C_{43}H_{72}O_9Si_3$: C, 63.19; H, 8.88. Found C, 63.19; H, 8.92.

Ketone 22a ($P_5$=H). To a vigorously stirred solution of crude 22a ($P_7$=BOM, $P_{10}$=TES, $P_{13}$=TBS, $P_5$=TMS) (231 mg, 0.274 mmol) in acetonitrile (7 mL) at 0° C. was added dropwise 7 mL of a 1:10:10 (by volume) mixture of 48% aqueous HF:pyridine:acetonitrile. After stirring for 20 min, 2 mL of a saturated aqueous $NaHCO_3$ solution was added. The reaction mixture was diluted with 150 mL of ethyl acetate and washed with 30 mL of a saturated aqueous $NaHCO_3$ solution and brine, dried over anhydrous $Na_2SO_4$ and concentrated under reduced pressure to give 223 mg of the crude alcohol as a colorless oil. This material was purified by silica gel chromatography to yield 155 mg (74%) of ketone 22a ($P_7$=BOM, $P_{10}$=TES, $P_{13}$=TBS, $P_5$=H), 15 mg (7%) of the 5β-hydroxy ketone and 33 mg (14% recoverable material) of a 1:1 mixture of TMS enol ether 21a and ketone 18.

22a ($P_7$ =BOM, $P_{10}$=TES, $P_{13}$=TBS, $P_5$=H): $^1$H NMR (500 MHz, $CDCl_3$)$_3$) δ 0.10 (s, 3H, TBS $CH_3$), 0.14 (s, 3H, TBS $CH_3$), 0.59 (q, J=8.2 Hz, 6H, TES $CH_2$), 0.94 (s, 9H, TBS t-Bu), 0.94 (t, J=8.2 Hz, 9H, TES $CH_3$), 1.23 (s, 3H, $CH_3$ 19), 1.32 (s, 3H, $CH_3$ 17), 1.33 (s, 3H, $CH_3$ 16), 1.83 (dd, J=11.09 13.7 Hz, 1H, H6β), 1.97 (d, J=1.4 Hz, 3H, H18), 2.01 (dd, J=3.2, 13.7 Hz, 1H, H9β), 2.11 (ddd, J=5.5, 7.7, 13.7 Hz, 1H, H6α), 2.47 (dd, J=8.7, 15.4 Hz, 1H, H14β), 2.57 (m, 2H, H14α, H9α), 2.88 (d, J=5.5 Hz, 1H, H3α), 3.39 (dd, J=7.7, 11.0 Hz, 1H, H7α), 3.41 (d, J=3.3 Hz, 1H, OH-5), 4.38 (m, 2H, H5β, H10), 4.55 (d, J=5.5 Hz, 1H, H2β) 4.57 (d, J=11.5 Hz 1H, C$\underline{H}_2$Ph), 4.62 (d, J=11.5 Hz 1H, C$\underline{H}_2$Ph), 4.72 (m, 2H, H13β, $OCH_2O$), 4.80 (d, J=7.1 Hz 1H, $OCH_2O$), 7.31 (m, 5H, Ph).

Ketone 22a ($P_5$=TMS) from ketone 22a ($P_5$=H). To a vigorously stirred soluton of 5-hydroxy-4-ketone 22a ($P_7$=BOM, $P_{10}$=TES, $P_{13}$=TES, $P_5$=H) (51 mg, 0.067 mmol) in $CH_2Cl_2$ (2.2 mL) and triethylamine (0.14 mL, 1.0 mmol) under nitrogen at 0° C. was added trimethylsilylchloride (0.041 mL, 0.34 mmol). After 0.5 h, the reaction mixture was quenched with 5 mL of a saturated aqueous $NaHCO_3$ solution and extracted with 150 mL hexanes. The organic phase was washed with 50 mL of a saturated aqueous $NaHCO_3$ soluton and brine, dried over anhydrous $Na_2SO_4$ and concentrated under reduced pressure to give 56 mg a colorless oil. This material was filtered through silica gel and the filtrate was concentrated under reduced pressure to yield 54 mg (96%) of ketone 22a ($P_7$=BOM, $P_{10}$=TES, $P_{13}$=TBS, $P_5$=TMS).

Alcohol 23a. To a stirred solution of ketone 22a ($P_7$=BOM, $P_{10}$=TES, $P_{13}$=TBS, $P_5$=TMS) (18.9 mg, 0.023 mmol) in $CH_2Cl_2$ (4 mL) under nitrogen at −65° C. was added dropwise a 0.073 mL of a 3.1 M solution of MeMgBr in ether (0.23 mmol). The reaction mixture was allowed to warm to −48° C., stirred for 16.5 h and then quenched with 0.13 mL of a 2.0M solution of AcOH in THF (0.25 mmol) and then poured into a stirring mixture of 50 mL of a saturated aqueous $NaHCO_3$ solution and 50 mL of ethyl acetate. The aqueous phase was extracted with 50 mL ethyl acetate. The combined organic phases were washed with brine, dried over anhydrous $Na_2SO_4$ and concentrated under reduced pressure to yield 20.5 mg of a colorless oil. This material was purified by silica gel chromatography to yield 8.4 mg (95%) of alcohol 23a ($P_7$=BOM, $P_{10}$=TES, $P_{13}$=TBS, $P_5$=TMS) as a colorless oil.

23a ($P_7$=BOM, $P_{10}$=TES, $P_{13}$=TBS, $P_5$=TMS): $^1$H NMR (500 MHz, $CDCl_3$) δ 0.09 (s, 9H, TMS), 0.11 (s, 3H, TBS $CH_3$), 0.12 (s, 3H, TBS $CH_3$), 0.56 (q, J=7.9 Hz, 6H, TES $CH_2$), 0.92 (t, J=7.9 Hz, 9H, TES $CH_3$), 0.93 (s, 9H, TBS t-Bu), 1.25 (s, 3H, $CH_3$ 17), 1.28 (s, 3H, $CH_3$ 19), 1.33 (s, 3H, $CH_3$ 20), 1.34 (s, 3H, $CH_3$ 16), 1.74 (ddd, J=3.8, 4.1, 13.0 Hz, 1H, H6α), 1.99 (d, J=1.4 Hz, 3H, H18), 2.01 (dd, J=11.3, 13.0 Hz, 1H, H9α), 2.06 (m, 2H, H3, H9β), 2.13 (ddd, J=1.7, 12.3, 13.0 Hz, 1H, H6β), 2.37 (dd J=5.5, 15.0 Hz, 1H, H14α), 2.54 (dd, J=9.2, 15.0 Hz, 1H, H14β), 2.96 (s, 1H, OH-4), 3.51 (dd, J=1.7, 4.1 Hz, 1H, H5), 3.73 (dd, J=3.8, 12.3 Hz, 1H, H7α), 4.32 (dd, J=4.19 11.3 Hz, 1H, H10β), 4.64 (s, 2H, C$\underline{H}_2$Ph), 4.72 (d, J=6.8 Hz, 1H, $OCH_2O$), 4.80 (m, 3H, H2, H13, $OCH_2O$), 7.31 (m, 5H, Ph). Anal. Calcd. for $C_{44}H_{76}O_9Si_3$: C, 63.42; H, 9.19. Found C, 63.40; H, 9.15.

Hydroxy olefin 24a. To a refluxing solution of alcohol 23a ($P_7$=BOM, $P_{10}$=TES, $P_{13}$=TBS, $P_5$=TMS) (46.7 mg, 0.055 mmol) in toluene (1.1 mL) was added 1.1 mL of a 0.1M solution of Burgess reagent in toluene (0.11 mmol). The mixture was refluxed for 20 min then cooled to room temperature, diluted with ethyl acetate, washed with a saturated solution of $NaHCO_3$ and brine, dried over anhydrous $Na_2SO_4$ and filtered. Concentration of the filtrate under vacuum yielded 46 mg of crude olefin. This material was used without further purification.

To a stirred solution of this crude olefin (46 mg, 0.055 mmol) in acetonitile (2.5 mL) at 0° C. was added 2.5 mL of a 1:10:10 (by volume) mixture of 48% aqueous HF: pyridine:acetonitrile. The mixture was stirred at 0° C. for 20 min, quenched with a saturated solution of $NaHCO_3$ and extracted twice with ethyl acetate. The combined organic phases were washed with brine, dried over anhydrous $Na_2SO_4$ and filtered. Concentration of the filtate under vacuum yielded 48 mg of a colorless oil which was purified by silica gel chromatography to yield 25.9 mg (62%) of hydroxy olefin 24a ($P_7$=BOM, $P_{10}$=TES, $P_{13}$=TBS, R=H) as well as 2.1 mg of unreacted alcohol 23a (4%).

24a ($P_7$=BOM, $P_{10}$=TES, $P_{13}$=TBS, R=H): mp 66–68° C. $^1$H NMR (500 MHz, $CDCl_3$) δ 0.12 (s, 3H, TBS $CH_3$), 0.13 (s, 3H, TBS $CH_3$) 0.59 (q, J=7.9 Hz, 6H, TES $CH_2$), 0.94 (t, J=7.9 Hz, 9H, TES $CH_3$), 0.95 (s, 9H, TBS t-Bu), 1.18 (s, 3H, $CH_3$ 19), 1.23 (s, 3H, $CH_3$ 17), 1.35 (s, 3H, $CH_3$ 16), 1.73 (d, 1H, J=3.4 Hz, OH5), 1.83 (dd, J=9.9, 10.5 Hz, 1H, H9α), 1.91 (ddd, J=7.2, 7.5, 13.4 Hz, 1H, H6α), 1.97 (dd, J=3.8, 9.9 Hz, 1H, H9β), 2.03 (d, J=1.4 Hz, 3H, 18), 2.14 (ddd, J=9.6, 9.6, 13.4 Hz, 1H, H6β) 2.35 (dd, J=5.1, 15.4 Hz, 1H, H14α), 2.50 (dd, J=9.6, 15.4 Hz, 1H, H14β), 3.03 (d, J=5.8 Hz, 1H, H3α), 3.44 (dd, J=7.5, 9.6, Hz, 1H, H7α), 4.38 (m, 2H, H10, H5), 4.54 (d, J=5.8 Hz, 1H, H2), 4.58 (d, J=11.6 Hz, 1H, C$\underline{H}_2$Ph), 4.62 (d, J=11.6 Hz, 1H, C$\underline{H}_2$Ph), 4.73 (d, J=7.0 Hz, 1H, $OCH_2O$), 4.75 (m, 1H, H13), 4.79 (d, J=7.0 Hz, 1H, $OCH_2O$), 5.00 (s, 1H, H20E), 5.18 (s, 1H, H20Z), 7.31 (m, 5H, Ph). Anal. Calcd. for $C_{41}H_{66}O_8Si_2$×0.5$H_2O$: C, 65.47; H, 8.98. Found C, 65.63; H, 8.97.

Allyl mesylate 24aa. To a stirred solution of allyl alcohol 24a ($P_7$=BOM, $P_{10}$=TES, $P_{13}$=TBS, R=H) (11.5 mg, 0.0154 mmol) in pyridine (0.6 mL) under nitrogen at 0° C. was added dropwise methanesulfonyl chloride (0.02 mL, 0.258 mmol). After 45 min, a saturated aqueous $NaHCO_3$ solution (0.05 mL) was added. The mixture was stirred for 10 min, poured into 20 mL of a saturated aqueous $NaHCO_3$ solution and extracted with 40% ethyl acetate/hexane (20 mL×3). The combined organic phase was dried over anhydrous $Na_2SO_4$ and concentrated under reduced pressure to give 13 mg of 24aa ($P_7$=BOM, $P_{10}$=TES, $P_{13}$=TBS, R=Ms) as a colorless oil. This material was used without further purification.

24aa ($P_7$=BOM, $P_{10}$=TES, $P_{13}$=TBS, R=Ms): $^1$H NMR (300 MHz, $CDCl_3$); δ 0.12 (s, 3H, TBS $CH_3$), δ 0.13 (s, 3H, TBS $CH_3$), 0.58 (q, J=7.9 Hz, 6H, TES $CH_2$), 0.93 (s, 9H, TBS t-Bu), 0.94 (t, J=7.9 Hz, 9H, TES $CH_3$), 1.23 (s, 3H,

CH₃ 17), 1.22 (s, 3H, CH₃ 19), 1.34 (s, 3H, CH₃ 16), 1.80 (br t, J=13 Hz, 1H, H9α), 1.98 (m, 1H, H6), 1.79 (ddd, J=2.2, 5.5, 15.1 Hz, 1H, H14α), 2.01 (d, J=1.1 Hz, 1H, CH₃18), 2.06 (dd, J=3.3, 13.7 Hz, 1H, H9β), 2.01 (br s, 3H, CH3 18), 2.22–2.32 (m, 3H, H14α, H6α, H6β), 2.54 (dd, J=9.9, 15.4 Hz, 1H, H14β), 3.02 (s, 3H, OSO₂CH₃), 3.05 (d, J=6.0 Hz, 1H, H3α), 3.45 (t, J=8.5 Hz, 1H, H7α), 4.37 (dd, J=3.6, 11.0 Hz, 1H, H10β), 4.57 (d, J=6.0 Hz, 1H, H2β), 4.59 (q, 2H, PhCH₂O), 4.69 (d, J=7.1 Hz, 1H, OCH₂O), 4.74 (m, 1H, H13β), 4.76 (d, J=7.1 Hz, 1H, OCH₂O), 5.03 (br t, J=8.5 Hz, 1H, H5β), 5,09 (br s, 1H, H20), 5.24 (br s, 1H, H20), 7.35 (m, 5H, Ph).

Triol 25a. To a stirred solution of allyl alcohol 24a (P₇=BOM, P₁₀=TES, P₁₃=TBS, R=H) (45 mg, 0.0606 mmol) in a mixture of pyridine (0.32 mL) and ether (3.2 mL) under nitrogen at 0° C. was added a 0.157 M solution of OsO₄ in THF (0.42 mL, 0.066 mmole). After 12 h at 0° C., NaHSO₃ (530 mg), pyridine (0.3 mL), THF (2 mL) and water (3 mL) were added. The mixture was vigorously stirred at room temperature for 14 h, poured into 50 mL of a saturated aqueous NaHCO₃ solution and extracted with ethyl acetate (40 mL×3). The combined organic phase was dried over anhydrous Na₂SO₄ and concentrated under reduced pressure to give 60 mg of a pale yellow oil, which was column chromatographed (30% ethyl acetate/hexane) to yield 34.3 mg (73%) of triol 25a (P₇=BOM, P₁₀=TES, P₁₃=TBS).

25a (P₇=BOM, P₁₀=TES, P₁₃=TBS): ¹H NMR (500 MHz, CDCl₃); δ 0.11 (s, 6H1, TBS CH₃), 0.60 (ddd, J=9.0 Hz, 6H, TES CH₂), 0.79 (s, 3H, CH₃ 19), 0.93 (s, 9H, TBS t-Bu), 0.94 (dd, J=9.0 Hz, 9H, TES CH₃), 1.22 (s, 3H, CH₃ 17), 1.35 (s, 3H, CH₃ 16), 1.64 (dd, J=5.6, 16.4 Hz, 1H, H9β), 1.70 (m, 1H, H6β), 2.22 (dd, J=2.7, 16.8 Hz, 1H, H9α), 2.23 (d, J=0.7 Hz, 3H, CH₃ 18),, 2.36 (dd, J=9.2, 15.0 Hz, 1H, H14β), 2.45 (m, 1H, H6α), 2.96 (s, 1H, OH5), 3.21 (dd, 6.9, 15.0 Hz, 1H, H14α), 3.42 (d, J=5.0 Hz, 1H, H3α), 3.53 (m, 1H, H20), 3.38 (s, 1H, OH4), 3.70 (t, J=3.0 Hz, 1H, H5β), 4.04 (br d, J=11 Hz, 1H, H20), 4.06 (dd, J=11.5, 5.0 Hz, 1H, H7α), 4.48 (d, J=5.0 Hz, 1H, H2β), 4.49 (d, J=12.0 Hz, 1H, PhCH₂O), 4.53 (br s, 1H, H10β), 4.71 (m, 1H, H13β), 4.72 (d, J=12.0 Hz, 1H, PhCH₂O), 4.85 (d, J=6.8 Hz, 1H, OCH₂O), 4.98 (d, J=6.8 Hz, 1H, OCH₂O), 7.34 (m, 5H, Ph). Anal. Calcd. for C₄₁H₆₈O₁₀Si₂: C, 63.36; 9 8.82. Found C, 63.19; H, 8.75.

Diol mesylate 26a. To a stirred solution of allyl mesylate 24,a (P₇=BOM, P₁₀=TES, P₁₃=TBS, R=Ms) (5 mg, 0.0064 mmol) in a mixture of pyridine (0.4 mL) and THF (0.4 mL) under nitrogen at room temperature was added a 0.157 M solution of OsO₄ in THF (0.06 mL). After 7 h, NaHSO₃ (150 mg) and water (0.2 mL) were added. The mixture was vigorously stirred for 14 h, poured into 20 mL of a saturated aqueous NaHCO₃ solution and extracted with ethyl acetate (20 mL×3). The combined organic phase was dried over anhydrous Na₂SO₄ and concentrated under reduced pressure to give 6 mg of a pale yellow oil. The oil was column chromatographed (40% ethyl acetate/hexane) to yield 2.7 mg (50%) of diol mesylate 26a (P₇=BOM, P₁₀=TES, P₁₃=TBS, R=Ms).

26a (P₇=BOM, P₁₀=TES, P₁₃=TBS, R=Ms): ¹H NMR (500 MHz, CDCl₃); δ 0.14 (s, 6H, TBS CH₃), 0.58 (ddd, J=8.0 Hz, 6H, TES CH₂), 0.89 (s, 3H, CH₃ 19), 0.93 (s, 9H, TBS t-Bu), 0.94 (dd, J=8.0 Hz, 9H, TES CH₃), 1.31 (s, 3H, CH₃ 17), 1.37 (s, 3H, CH₃ 16), 1.76 (dd, J=5.5, 15.1, 1 Hz, H9β), 1.95 (m, 1H, H6β), 2.23 (d, J=0.7 Hz, 3H, CH₃ 18), 2.25 (dd, J=4.8, 15.1 Hz, 1H, H9α), 2.39 (dd, J=9.2, 15.1 Hz, 1H, H14β), 2.45 (m 1H, H6α), 2.89 (dd, 6.8, 15.1 Hz, 1H, H14α), 3.05 (d, J=3.4 Hz, 1H, H3α), 3.06 (s, 3H, OSO₂CH₃), 3.35 (s, 1H, OH4), 3.52 (m, 1H, H20), 3.92 (dd, J=4.5, 11.6 Hz, 1H, H7α), 4.13 (dd, J=1.0, 11.3 Hz, 1H, H20), 4.46 (br d, J=4.5 Hz, 1H, H10), 4.52 (d, J=3.4 Hz, 1H, H2), 4.54 (d, J=12.0 Hz, 1H, PhCH₂O), 4.70 (d, J=12.0 Hz, 1H, PhCH₂O), 4.83 (d, J=6.9 Hz, 1H, OCH₂O), 4.84 (m, 1H, H5β), 4.92 (m, 1H, H13β), 4.93 (d, J=6.9 Hz, 1H, OCH₂O), 7.34 (m, 5H, Ph).

Diol tosylate 26aa. To a stirred solution of triol 25a (P₇=BOM, P₁₀=TES, P₁₃ =TBS) (37 mg, 0.0476 mmole) in CH₂Cl₂ (0.4 mL) under nitrogen at −78° C. was added triethylamine (0.25 mL) followed by trimethylchlorosilane (0.075 mL). The solution was stirred at −78° C. for 1h, poured into 20 mL of a saturated aqueous NaHCO₃ solution and extracted with chloroform (30 mL×3). The combined organic phase was dried over anhydrous Na₂SO₄, and concentrated under reduced pressure to give 38.2 mg of a colorless oil. This oil was dissolved in THF (0.5 mL) and cooled to −78° C. To this solution was added a 0.2 M solution of LDA in THF (0.9 mL, 0.18 mmole). After 20 min at −78° C., p-toluenesulfonyl chloride (35 mg, 0.183 mmole) was added. After strrng at −35° C. for 3 h, MeOH (0.2 mL) and diethylane (0.3 mL) were added. The solution was stirred at −35° C. for 30 min and poured into 30 mL of a saturated aqueous NaHCO₃ solution and extracted with chloroform (40 mL×3). The combined organic phases were dried over anhydrous Na₂SO₄, and concentrated under reduced pressure to give 58 mg of a colorless oil. The oil was dissolved in acetonitrile (3.6 mi) and pyridine (3.6 mL). To this solution at 0° C. was added 48% aqueous solution of HF (0.36 mL). The solution was stirred at 0° C. for 15 min, poured into 30 mL of a saturated aqueous NaHCO₃ solution and extracted with chloroform (40 mL×3). The combined organic phase was dried over anhydrous Na₂SO₄, and concentrated under reduced pressure to give 56 mg of crude diol tosylate 26aa. Column chromatography (40% ethylacetate/hexane) yielded 34 mg (80%) diol tosylate 26aa (P₇=BOM, P₁₀=TES, P₁₃=TBS, R=Ts).

26aa (P₇=BOM, P₁₀=TES, P₁₃=TBS, R=Ts). ¹H NMR (300 MHz, CDCl₃); δ 0.18 (s, 6H, TBS CH₃), 0.58 (d, J=12.5 Hz, 6H, TES CH₂), 0.82 (s, 3H, CH₃ 19), 0.94 (dd, J=13.0 Hz, 9H, TES CH₃), 0.97 (s, 9H, TBS t-Bu), 1.28 (s, 3H, CH₃ 17), 1.34 (s, 3H, CH₃ 16), 1.67 (dd, J=16.5, 4.4 Hz, 1H, H9β), 1.80 (m, 1H, H6β), 2.13 (dd, J=16.5, 4.4 Hz, 1H, H9α), 2.18 (m, 1H, H6α), 2.24 (s, 3H, CH₃ 18), 2.33 (s, 3H, CH₃Ph), 2.42 (dd, J=14.8, 9.3 Hz, 1H, H14β), 2.90 (m, 1H, H14α), 2.93 (br s, 1H, OH4), 3.08 (br d, J=3.3 Hz, 1H, H3α), 3.38 (br t, J=1.0 Hz, 1H, H7α), 3.87 (m, 1H, H20), 4.09 (br d, J=9.9 Hz, 1H, H20), 4.52 (d, J=3.3 Hz, 1H, H2β), 4.45 (br d, J=4.4 Hz, 1H, H10), 4.46 (d, J=12.1 Hz, 1H, PhCH₂O), 4.59 (d, J=12.1 Hz, 1H, PhCH₂O), 4.66 (br t, J=3.8 Hz, 1H, H5β), 4.75 (d, J=7.1 Hz, 1H, OCH₂O), 4.83 (d, J=7.1 Hz, 1H, OCH₂O), 4.89 (br dd, J=7.7, 6.6 Hz, 1H, H13β), 7.14 (d, J=8.2 Hz, 2H, SO₂Ph), 7.34 (m, 5H, OCH₂Ph), 7.75 (d, J=8.2 Hz, 2H, SO₂Ph).

Oxetane 27a from diol mesylate 26a. To a stirred solution of diol mesylate 26a (P₇=BOM, P₁₀=TES, P₁₃=TBS, R=Ms) (2.7 mg) in toluene (0.4 mL) under nitrogen at room temperature was added diisopropyl ethylamine (0.008 mL). The solution was refluxed for 3.5 h, cooled to room temperature, poured into 20 mL of a saturated aqueous NaHCO₃ solution and extracted with ethyl acetate (20 mL×3). The combined organic phase was dried over anhydrous Na₂SO₄, and concentrated under reduced pressure to give 3 mg of a pale yellow oil. The oil was column chromatographed (30% ethyl acetate/hexane) to yield 1 mg (42%) of oxetane 27a.

27a (P₇=BOM, P₁₀=TES, P₁₃TBS): ¹H NMR (500 MHz, CDCl₃); δ 0.10 (s, 6H, TBS CH₃), 0.59 (dd, J=8.0 Hz, 6H,

TES CH$_2$), 0.92 (s, 9H, TBS t-Bu), 0.94 (dd, J=8.0 Hz, 9H, TES CH$_3$), 1.20 (s, 3H, CH$_3$ 17), 1.26 (s, 3H, CH$_3$ 19), 1.32 (s, 3H, CH$_3$ 16), 1.93 (dd, J=11.3, 13.4 Hz, 1H, H9α), 1.98 (d, J=1.4 Hz, 3H, CH$_3$ 18), 2.06 (dd, J=6.0, 18.6 Hz, 1H, H6β), 2.11 (dd, J=4.5, 13.4 Hz, 1H, H9β), 2.14 (d, J=5.5 Hz, 1H, H3α), 2.41 (dd, J=9.2, 15.1 Hz, 1H, H14β), 2.43 (m, 1H, H6α), 2.54 (s, 1H, OH4), 2.76 (dd, J=5.2, 15.1 Hz, H14α), 3.21 (dd, J=3.4, 13.0 Hz, 1H, H7α), 4.36 (d, J=8.6 Hz, 1H, H20α), 4.37 (dd, J=4.1, 11.3 Hz, 1H, H10β), 4.40 (br d, J=8.2 Hz, 1H, H5α), 4.60 (d, J=5.5 Hz, 1H, H2β), 4.61 (d, J=12.6 Hz, 1H, PhCH$_2$O), 4.67 (m, 1H, H13β), 4.69 (d, J=12.6 Hz, 1H, PhCH$_2$O), 4.75 (d, J=7.5 Hz, 1H, OCH$_2$O), 4.86 (d, J=7.5 Hz, 1H, OCH$_2$O), 4.91 (dd, J=0.7, 8.6 Hz, 1H, H20β), 7.34 (m, 5H, Ph). Anal. Calcd. for C$_{41}$H$_{66}$O$_9$Si$_2$: C, 64.87; H, 8.76. Found C, 64.61; H, 8.78.

Oxetane 27a from diol tosylate 26aa. To a stirred solution of diol tosylate 26aa (P$_7$=BOM, P$_{10}$=TES, P$_{13}$=TBS, R=Ts) (33 mg, 0.0354 mmole) in toluene (3.3 mL) under nitrogen at room temperature was added DBU (0.11 mL, 0.73 mmole). The solution was heated at 80° C. for 10 min, then the temperature was increased up to 110° C. during a 40 min period, maintained at 110° C. for 30 more min and cooled to room temperature. The solution was filtered through a short pad of silica gel using 30% ethyl acetate/hexane as eluent. The filtrate was concentrated to give 25 mg of crude 27a, which was column chromatographed (30% ethyl acetate/hexane) to yield 21 mg (78%) of oxetane 27a (P$_7$=BOM, P$_{10}$=TES, P$_{13}$ =TBS).

Oxetane 29. To a stirred solution of oxetane 27a (P$_7$=BOM, P$_{10}$=TES, P$_{13}$=TBS) (21 mg 0.0276 mmloe) and dimethylaminopyridine (3.4 mg, 0.0278 mmole) in pyridine (110 μL, 1.37 mmole) under nitrogen at room temperature was added acetic anhydride (26 μL, 0.276 mmole). The solution was stirred for 25 h, diluted with ethyl acetate, poured into 20 mL of saturated aqueous NaHCO$_3$ solution and extracted with ethyl acetate (20 mL×3). The combined organic phases were dried over anhydrous Na$_2$SO$_4$ and concentrated under reduced pressure to give 26 mg of a pale yellow oil, which was column chromatographed (25% ethyl acetate/hexane) to yield 16 mg (72%) of oxetane 29 (P$_7$=BOM, P$_{10}$=TES, P$_{13}$=TBS).

29 (P$_7$=BOM, P$_{10}$=TES, P$_{13}$=TBS): $^1$H NMR (500 MHz, CDCl$_3$); δ 0.10 (s, 3H, TBS CH$_3$), 0.12 (s, 3H, TBS CH$_3$), 0.56 (q, 6H, TES CH$_2$), 0.92 (t, 9H, TES CH$_3$), 0.94 (s, 9H, TBS t-Bu), 1.35 (s, 3H, CH$_3$ 16), 1.30 (s, 3H, CH$_3$ 17), 1.29 (s, 3H, CH$_3$ 19), 1.96 (br t, J=13.0 Hz, 1H, H9α), 1.98 (d, J=1.4 Hz, 3H, CH$_3$ 18), 2.02 (dd, J=7.5, 13.0, 1H, H9β), 2.07 (dt, J=8.0, 13.0 Hz, 1H, H6β), 2.13 (s, 3H, OAc), 2.24 (dd, J=3.4, 15.0, 1H, H14α), 2.40 (dd, J=8.6, 15.0 Hz, 1H, H14β), 2.51 (ddd, J=4.1, 9.2, 15.0 Hz, 1H, H6α), 2.63 (d, J=6.5 Hz, 1H, H3α), 3.69 (dd, J=4.1, 13.0 Hz, 1H, H7α), 4.35 (dd, J=3.4, 11.3 Hz, 1H, H10β), 4.64 (m, 4H, PhCH$_2$O, H2β, H5α), 4.75 (d, J=7.2 Hz, 1H, OCH$_2$O), 4.76 (br d, J=9.2 Hz, 1H, H20), 4.83 (d, J=7.2 Hz, 1H, OCH$_2$O), 4.85 (br d, J=9.2 Hz, 1H, H20), 4.88 (br t, J=8.2 Hz, 1H, H13β), 7.35 (m, 5H, Ph).

Benzoate 30. To a stirred solution of oxetane 29 (P$_7$=BOM, P$_{10}$=TES, P$_{13}$ =TBS) (6 mg, 0.0075 mmol) in THF (0.5 mL) under nitrogen at −78° C. was added a 0.3M solution of phenyllithium in ether (44 μL, 0.013 mmol). The solution was stirred at −78° C. for 15 min and quenched with a 10% solution of acetic acid in THF. The solution was diluted with ethyl acetate, poured into 20 mL of a saturated aqueous NaHCO$_3$ solution and extracted with ethyl acetate (20 mL×3). The combined organic phases were dried over anhydrous Na$_2$SO$_4$ and concentrated under reduced pressure to give 8 mg of a pale yellow oil. The oil was column chromatographed (25% ethyl acetate/hexane) to yield 6.2 mng (94%) of benzoate 30 (P$_7$=BOM, P$_{13}$=TBS, R=TES).

30 (P$_7$=BOM, P$_{13}$=TBS, R=TES): $^1$H NMR (500 MHz, CDCl$_3$); δ 0.09 (s, 3H, TBS CH$_3$), 0.14 (s, 3H, TBS CH$_3$), 0.60 (ddd, 6H, TES CH$_2$), 0.94 (s, 9H, TBS t-Bu), 0.96 (t, 6H, TES CH$_3$), 1.23 (s, 3H, CH$_3$ 17), 1.38 (s, 3H, CH$_3$ 19), 1.46 (s, 3H, CH$_3$ 16), 1.69 (s, 1H, OH1), 1.97 (ddd, J=14.5, 10.0, 3.1 Hz, 1H, H6β), 2.05 (dd, J=16.1, 5.1 Hz, 1H, H9β), 2.09 (dd, J=15.1, 6.2 Hz, 1H, H14β), 2.13 (s, 3H, CH$_3$ 18), 2.22 (dd, J=15.1, 8.2 Hz, 1H, H14α), 2.23 (dd, J=15.0, 8.5 Hz, 1H, H9β), 2.24 (s, 1H, OAc 4), 2.38 (dd, J=16.1, 4.1 Hz, 1H, H9α), 2.67 (m, 1H, H6α), 3.40 (d, J=6.2 Hz, 1H, H3α), 3.99 (dd, J=10.1, 6.8 Hz, 1H, H7α), 4.20 (d, J=8.2 Hz, 1H, H20β), 4.29 (d, J=8.2 Hz, 1H, H20α), 4.49 (d, J=12.0 Hz, 1H, PhCH$_2$O), 4.63 (br t, 1H, H10β), 4.74 (d, J=12.0 Hz, 1H, PhCH$_2$O), 4.92 (d, J=6.9 Hz, 1H, OCH$_2$O), 4.91–4.95 (m, 2H, H13β & H5α), 5.0 (d, J=6.9 Hz, 1H, OCH$_2$O) 5.66 (d, J=6.2 Hz, 1H, H2β), 7.28 (m, 1H, PhCH$_2$), 7.35 (m, 4H, PhCH$_2$), 7.48 (m, 2H, PhCOO-m), 7.59 (m, 1H, PhCO¢ -p), 8.11 (m, 2H, PhCOO-o).

Alcohol 31. To a solution of benzoate 30 (P$_7$=BOM, P$_{13}$=TBS, R=TES) (6.2 mg, 0.007 mmol) in 2 mL of THF was added 0.1 mL of a 0.1 M solution of TBAF in THF. The mixture was stirred for 2 h at 25° C. under nitrogen. The reaction mixture was diluted with 10 mL of ethyl acetate, then poured into 10 mL of a saturated aqueous NaHCO$_3$ solution. The organic phase was washed with 10 mL of a saturated aqueous NaHCO$_3$ solution, dried over anhydrous Na$_2$SO$_4$ and concentrated under reduced pressure to give 4.5 mg (93%) of alcohol 31 (P$_7$=BOM, P$_{13}$=TBS, R=H).

31 (P$_7$=BOM, P$_{13}$=TBS, R=H): mp 213–216° C. $^1$H NMR (500 MHz, CDCl$_3$), δ 0.10 (s, 3H, TBS CH$_3$), 0.15 (s, 3H, TBS CH$_3$), 0.94 (s, 9H, TBS t-Bu), 1.26 (s, 3H, CH$_3$ 17), 1.39 (s, 3H, CH$_3$ 19), 1.45 (s, 3H, CH$_3$ 16), 1.68 (s, 1H, OH1), 1.89 (ddd, J=14.5, 10.0, 2.5 Hz, 1H, H6β), 2.10 (dd, J=15.0, 9.0 Hz, 1H, H14β), 2.15 (dd, J=15.0, 8.0 Hz, 1H, H14α), 2.18 (s, 3H, CH$_3$ 18), 2.23 (dd, J=15.0, 8.5 Hz, 1H, H9β), 2.26 (s, 1H, OAc 4), 2.40 (dd, J=15.0, 3.5 Hz, 1H, H9α), 2.68 (m, 1H, H6α), 2.90 (br s, 1H, OH10), 3.54 (d, J=6.0 Hz, 1H, H3α), 4.16 (d, J=8.0 Hz, 1H, H20β), 4.23 (dd, J=10.0, 7.0 Hz, 1H, H7α), 4.30 (d, J=8.0 Hz, 1H, H20α), 4.68 (dd, J=15 Hz, 2H, PhCH$_2$O), 4.78 (m, 1H, H10β), 4.87 (d, J=6.5 Hz, 1H, OCH$_2$O), 4.95 (t, J=2.0 Hz, 1H, H20α), 4.92 (d, J=7.0 Hz, 1H, OCH$_2$O), 4.93 (br d, J=2.0 Hz, 1H, H13β), 4.96 (br d, J=6.5 Hz, 1H, H5α), 4.97 (d, J=6.5 Hz, 1H, OCH$_2$O), 5.68 (d, J=6.0 Hz, 1H, H2β), 7.28 (m, 1H, PhCH$_2$O), 7.35 (m, 4H, PhCH$_2$O), 7.40 (m, 2H, PhCOO-m), 7.59 (m, 1H, PhCOO-p), 8.13 (m, 2H, PhCOO-o). Anal. Calcd. for C$_{43}$H$_{60}$O$_{10}$Si×0.5H$_2$O: C, 66.72; H, 7.94. Found C, 66.75; H, 7.96.

Alcohol 31 through Alcohol 30a. To a stirred solution of oxetane 29 (P$_7$=BOM, P$_{10}$=TES, P$_{13}$=TBS) (16 mg, 0.02 mmole) in acetonitrile (0.33 mL) at 0° C. was added a 4% solution of HF-pyridine complex in acetonitfile (0.8 mL). The solution was stirred at 0° C. for 11 h, diluted with ethyl acetate, poured into 20 mL of a saturated aqueous NaHCO3 solution and extracted with CHCl$_3$ (30 mL×3). The combined organic phases were dried over anhydrous Na$_2$SO$_4$ and concentrated under reduced pressure to give 13.5 mg (0.0196 mmole) of 30a as an oil. This oil was dissolved in THF (1 mL) and cooled to −78° C. To this solution at −78° C. was added a 0.285 M solution of phenyllithium in THF (0.144 mL, 2.2 eq.). After 10 min, the solution was poured into 20 mL of saturated aqueous NaHCO$_3$ solution and CHCl$_3$ (30 mL×3). The combined organic phase was dried over anhydrous Na$_2$SO$_4$ and concentrated under reduced pressure to give 16 mg of a pale yellow oil, which was crystalized to yield 12.7 mg (85%) of benzoate 31 ($P_7$=BOM, $P_{13}$=TBS, R=H).

Ketone 32. To a solution of benzoate 32 ($P_7$=BOM, $P_{13}$=TBS, R=H) (18 mg, 0.235 mmole) and 4methylmorpholine N-oxide (18 mg, 0.154 mmole) in $CH_2Cl_2$ (2.6 mL) at room temperature was added tetrapropylammonium perruthenate (6 mg, 0.017 mmole). The solution was stirred at room temperature for 15 min and filtered through silica gel with 30% ethyl acetate/hexane. The filtrate was concentrated under reduced pressure to yield ketobenzoate 32 ($P_7$=BOM, $P_{13}$=TBS) (18 mg, 100%).

32 ($P_7$=MOP, $P_{13}$=TBS): $^1$H NMR (300 MHz, $CDCl_3$) δ 0.12 (s, 3H, TBS $CH_3$), 0.16 (s, 3H, TBS $CH_3$), 0.94 (s, 9H, TBS t-Bu), 1.25 (s, 3H, $CH_3$), 1.42 (s, 3H, $CH_3$), 1.44 (s, 6H, MOP $CH_3$), 1.49 (s, 3H, $CH_3$), 1.75 (s, 1H, OH1), 1.76 (m, 1H, H6), 1.83 (s, 3H, $CH_3$ 18), 2.21 (dd, J=7, 15 Hz, 1H, H14), 2.25 (s, 3H, OAc), 2.29 (dd, J=8, 15 Hz, 1H, H14), 2.61 (d, J=16 Hz, 1H, H9), 2.74 (ddd, J=8, 9, 17 Hz, 1H, H6), 3.19 (s, 3H, MOP $OCH_3$), 3.20 (d, J=6 Hz, 1H, H3α), 3.32 (d, J=16 Hz, 1H, H9), 3.78 (dd, J=8, 10 Hz, 1H, H7), 4.15 (d, J=8 Hz, 1H, H20), 4.34 (d, J=8 Hz, 1H, H20), 4.89 (d, J=9 Hz, 1H, H5), 5.04 (m, 1H, H13), 5.90 (d, J=6 Hz, 1H, H2), 7.50 (m, 2H, PhCOO-m), 7.62 (m, 1H, PhCOO-p), 8.24 (m, 2H, PhCOO-o).

32 ($P_7$=TES, $P_{13}$=TBS): $^1$H NMR (300 MHz, $CDCl_3$) δ 0.12 (s, 3H, TBS $CH_3$), 0.16 (s, 3H, TBS $CH_3$), 0.65 (q, J=8 Hz, 3H, TES $CH_3$), 0.66 (q J=8 Hz, 3H, TES $CH_3$), 0.94 (s, 9H, TBS t-Bu), 1.00 (t, J=8 Hz, 3H, TES $CH_2$), 1.24 (s, 3H, $CH_3$), 1.38 (s, 3H, $CH_3$) 1.49 (s, 3H, $CH_3$), 1.75 (s, 1H, OH1), 1.80 (m, 1H, H6), 1.81 (s, 3H, $CH_3$ 18), 2.20 (dd, J=9, 15 Hz, 1H, H14), 2.26 (s, 3H, OAc $CH_3$), 2.29 (dd, J=8, 15 Hz, 1H, H14), 2.48 (ddd, J=8, 9,17 Hz, 1H, H6), 2.58 (d, J=17 Hz, 1H, H9), 3.15 (d, J=6 Hz, 1H, H3α), 3.36 (d, J=17 Hz, 1H, H9), 3.79 (dd, J=7, 9 Hz, 1H, H7), 4.14 (d, J=8 Hz, 1H, H20), 4.33 (d, J=8 Hz, 1H, H20), 4.90 (d, J=9 Hz, 1H, H5), 5.04 (m, 1H, H13), 5.90 (d, J=6 Hz, 1H, H2), 7.49 (m, 2H, PhCOOO-m) 7.61 (m, 1H, PhCOO-p), 8.13 (m, 2H, PhOOO-o).

32 ($P_7$=BOM, $P_{13}$=TBS): $^1$H NMR (500 MHz, $CDCl_3$); δ 0.16 (s, 3H, TTBS $CH_3$), 0.18 (s, 3H, TBS $CH_3$), 0.94 (s, 9H, TBS t-Bu), 1.26 (s, 3H, $CH_3$ 17), 1.47 (s, 3H, $CH_3$ 19), 1.52 (s, 3H, $CH_3$ 16), 1.76 (s, 1H, OH1), 1.83 (d, 3H, J=0.5 Hz, $CH_3$ 18), 1.89 (ddd, J=15.0, 9.5, 1.5 Hz, 1H, H6β), 2.21 (dd, J=15.0, 9.0 Hz, 1H, H14β), 2.26 (s, 1H, OAc 4), 2.29 (dd, J=15.0, 8.0 Hz, 1H, H14α), 2.72 (m, 1H, H6α), 2.75 (d, J=16 Hz, 1H, H9α), 3.18 (d, J=6.5 Hz, 1H, H3α), 3.26 (d, J=16.5 Hz, H9α), 3.65 (dd, J=9.0, 7.5 Hz, 1H, H7α), 4.15 (d, J=7.5 Hz, 1H, H20β), 4.34 (d, J=7.5 Hz, 1H, H20 α), 4.61 (d, J=12.0 Hz, 1H, PhC$\underline{H}_2$O), 4.72 (d, J=12.0 Hz, 1H, PhC$\underline{H}_2$O), 4.81 (d, J=7.0 Hz, 1H, $OCH_2$O), 4.92 (d, J=7.0 Hz, 1H, $OCH_2$O), 4.93 (br d, J=6.5 Hz, 1H, H5α), 5.05 (br t, J=6.5 Hz, 1H, H13β), 5.91 (d, J=6.0 Hz, 1H, H2β), 7.28 (m, 1H, PhC$\underline{H}_2$O), 7.35 (m, 4H, PhC$\underline{H}_2$O), 7.50 (m, 2H, PhCOO-m), 7.62 (m, 1H, PhCOO-p), 8.13 (m, 2H, PhCOO-o)

Hydroxyketone 33. To a THF (1.3 mL) solution of 32 ($P_7$=BOM, $P_{13}$=TES) (16.2 mg, 0.02 mmol) at −78° C. was added 4 equivalents of a 0.24M t-BuOK solution in THF (0.33 mL, 0.08 mmol.). The solution was warmed to −20° C. for 40 min and then briefly warmed to 0° C. before being cannulated into a 0° C. THF (1.3 mL) suspension of benzeneseleninic anhydride (57 mg, 0.16 mmol.). The reaction was stirred for 40 min. at 0° C. before being diluted with 20 mL of ethyl acetate and poured into 50 mL of aqueous saturated $NaHCO_3$. The organic layer was then washed with 50 mL of aqueous saturated $Na_2S_2O_3$ followed by 50 mL of aqueous saturated $NaHCO_3$. The organic layer was then dried with $Na_2SO_4$, filtered and evaporated to give 18.8 mg of the hydroxyketone as an oil. To a THF (1.3 mL) solution of the crude hydroxyketone (18.8 mg) was added 0.33 mL of a 0.24M solution of t-BuOK (0.08 mmol) at −78° C. The reaction was stirred 20 min. and then 0.25 mL of a 0.8M AcOH/THF solution was added at −78° C. and stirred 5 min. The mixture was dIluted with 20 mL of ethyl acetate and was poured into 50 mL of aqueous satated $NaHCO_3$. The organic layer was then dried with $Na_2SO_4$, filtered and evaporated to give 18.6 mg of a yellow solid which was then plug filtered through silica gel with 2% ethyl acetate/hexanes followed by 30% ethyl acetate/hexanes to give 15.9 mg of 33 ($P_7$=BOM, $P_{13}$=TBS) (96% yield).

33 ($P_7$=BOM, $P_{13}$=TBS); m.p. 234–236° C., $^1$NMR (500 MHz, $CDCl_3$) δ 0.13 (s, 3H, TBS $CH_3$), 0.15 (s, 3H, TBS $CH_3$), 0.95 (s, 9H, TBS t-Bu), 1.11 (s, 3H, $CH_3$ 16), 1.18 (s, 3H, $CH_3$ 17), 1.59 (s, 1H, OH1), 1.82 (s, 3H, $CH_3$ 18), 1.89 (ddd, J=2.1, 12.4, 14.4 Hz, 1H, H6β), 1.97 (d, J=2.0 Hz, 3H, $CH_3$ 18), 2.14 (dd, J=8.6, 15.4 Hz, 1H, H14β), 2.21 (dd, J=8.9, 15.4 Hz, 1H, H14α), 2.29 (s, 3H, Ac), 2.70 (ddd, J=6.5, 9.6, 14.4 Hz, 1H, H6α), 3.93 (d, J=6.9 Hz, 1H, H3α), 4.17 (d, J=8.6 Hz, 1H, H20β), 4.28 (d, J=2.4 Hz, 1H, OH10β), 4.31 (dd, J=6.5, 12.4 Hz, 1H, H7α), 4.32 (d, J=8.6 Hz, 1H, H20α), 4.45 (d, J=12.2 Hz, 1H, PhC$\underline{H}_2$O), 4.60 (d, J=12.2 Hz, 1H, PhC$\underline{H}_2$O), 4.60 (d, J=7.3 Hz, 1H, $OCH_2$O), 4.73 (d, J=7.3 Hz, 1H, $OCH_2$O), 4.97 (dd, J=2.1, 9.6 Hz, 1H, H5α), 5.01 (ddd, J=2.0, 8.6, 8.9 Hz, 1H, H13β), 5.35 (d, J=2.4 Hz, 1H, H10α), 5.64 (d, J=6.9 Hz, 1H, H2β), 7.3 (m, 5H, P$\underline{h}$C$H_2$), 7.49 (tt, J=1.7, 7.9 Hz, 2H, PhCOO-m), 7.61 (tt, J=1.7, 7.6 Hz, 1H, PhCOO-p), 8.10 (dd, J=1.2, 7.9 Hz, PhCOO-o).

33 ($P_7$=MOP, $P_{13}$=TBS): $^1$H NMR (300 MHz, $CDCl_3$) δ 0.13 (s, 3H, TBS $CH_3$), 0.15 (s, 3H, TBS $CH_3$), 0.95 (s, 9H, TBS t-Bu), 1.00 (s, 3H, $CH_3$ 16), 1.09 (s, 3H, $CH_3$ 17), 1.23 (s, 3H, MOP $CH_3$), 1.37 (s, 3H, MOP $CH_3$), 1.58 (s, 1H, OH1), 1.79 (s, 3H, $CH_3$ 19), 1.90 (ddd, J=2.6, 8.8, 13.7 Hz, 1H, H6β), 2.04 (s, 3H, $CH_3$ 18), 2.13 (dd, J=8.8, 15.5 Hz, 1H, H14β), 2.22 (dd, J=8.8, 15.5 Hz, 1H, H14α), 2.29 (s, 3H, OAc), 2.79 (ddd, 6.3, 9.9, 14.8 Hz, 1H, H6α), 3.17 (s, 3H, MOP $OCH_3$), 3.90 (d, J=7.1 Hz, 1H, H3α), 4.16 (d, J=8.2 Hz, 1H, H20α), 4.25 (d, J=2.2 Hz, 1H, OH4), 4.32 (d, J=8.8 Hz, 1H, H20β), 4.41 (dd, J=6.6, 11.0 Hz, 1H, H7α), 4.94 (dd, J=2.2, 9.9 Hz, 1H, H5α), 5.03 (ddd, J=1.1, 8.2, 8.8 Hz, 1H, H13β), 5.20 (d, J=6.2 Hz, 1H, H10α), 5.60 (d, J=7.2 Hz, 1H, H2β), 7.48 (t, J=7.7 Hz, 2H, PhCOO-m), 7.61 (t, J=7.7 Hz, 1H, PhCOO-p), 8.10 (d, J=7.1 Hz, 2H, PhCOO-o).

Acetate 34. To a pyridine (0.1 mL) solution of 33 ($P_7$=BOM, $P_{13}$=TBS) (15.9 mg, 0.02 mmol) and DMAP (1.2 mg, 0.01 mmol) at room temperature was added acetic anhydride (38 μL, 0.4 mmol) and the reaction smed 19 h. The mixture was then diluted with 20 mL of ethyl acetate and poured into 50 mL of aqueous saturated $NaHCO_3$. The organic layer was dried with $Na_2SO_4$, filtered and evaporated to give 18.1 mg of crude product. The material was plug filtered through silica gel with 20% ethyl acetate/hexanes to give 16.8 mg of 34 ($P_7$=BOM, $P_{13}$=TBS) (100% yield).

34 ($P_7$=BOM, $P_{13}$=TBS): $^1$H NMR (500 MHz, $CDCl_3$) δ 0.14 (s, 3H, TBS Me), 0.16 (s, 3H, TBS Me), 0.95 (s, 9H, TBS t-Bu), 1.17 (s, 3H, $CH_3$ 17), 1.18 (s, 3H, $CH_3$ 16), 1.63 (s, 1H, OH1), 1.76 (s, 3H, $CH_3$ 19), 1.99 (ddd, J=2.1, 10.6, 14.7 Hz, 1H, H6β), 2.04 (d, J=1.0 Hz, 3H, $CH_3$ 18), 2.17 (dd, J=8.6, 15.1 Hz, 1H, H14β), 2.19 (s, 3H, AcO10), 2.24 (dd, J=8.6, 15.1 Hz, 1H, H14α), 2.28 (s, 3H, AcO4), 2.88 (ddd, J=6.5, 9.8, 14.7 Hz, 1H, H6α), 3.87 (d, J=7.0 Hz, 1H, H3α), 4.15 (d, J=8.2 Hz, 1H, H20 β), 4.24 (dd, J=6.5, 10.6 Hz, 1H, H7α), 4.31 (d, J=8.2 Hz, 1H, H20α), 4.44 (d, J=12.0 Hz, 1H, PhCH$_2$O), 4.68 (d, J=12.0 Hz, 1H, PhCH$_2$O), 4.85 (s, 2H, OCH$_2$O), 4.95 (dd, J=2.1, 9.8 Hz, 1H, H5α), 5.65 (d, J=7.0 Hz, 1H, H2β), 6.39 (s, 1H, H10α), 7.30 (m, 5H, PhCH$_2$), 7.49 (tt, J=1.4, 8.2 Hz, 2H, PhCOO-m), 7.61 (tt, J=1.4, 7.2 Hz, 1H, PhCOO-p), 8.05 (dd, J=1.2, 8.2 Hz, 1H, PhCOO-o), IR (CHCl$_3$) ν 3600, 3050, 2975, 2880, 1750, 1730, 1460, 1379, 1250, 1100, 1020, 860 cm$^{-1}$.

34 (P$_7$=P$_{13}$=TES): $^1$H NMR (300 MHz, CDCl$_3$) δ 0.57 (q, J=7.7 Hz, 6H, TES CH$_2$), 0.67 (q, J=7.7 Hz, TES CH$_2$), 0.92 (t, J=7.7 Hz, 9H, TES CH$_3$), 1.01 (t, J=7.7 Hz, 9H, TES CH$_3$), 1.11 (s, 3H, CH$_3$ 17), 1.19 (s, 3H, CH$_3$ 19), 1.61 (s, 1H, OH1), 1.67 (s, 3H, CH$_3$ 16), 1.86 (ddd, J=2.2, 10.4, 14.3 Hz, 1H, H6β), 2.11 (d, J=1.1 Hz, 3H, CH$_3$ 18), 2.12 (m, 1H, H14β), 2.17 (s, 3H, OAc10), 2.23 (dd, J=7.6, 14.9 Hz, 1H, H14α), 2.28 (s, 3H, OAc4), 2.51 (ddd, J=6.9, 9.6, 14.3 Hz, 1H, H6α), 3.82 (d, J=7.2 Hz, 1H, H3α), 4.14 (d, J=8.3 Hz, 1H, H20β), 4.30 (d, J=8.3 Hz, 1H, H20α), 4.48 (dd, J=6.6, 10.4 Hz, 1H, H7α), 4.92 (dd, J=7.7, 8.8 Hz, 1H, H5α), 4.96 (d, J=8.2 Hz, 1H, H13β), 5.63 (d, J=6.6 Hz, 1H, H2α), 6.47 (s, 1H, H10α), 7.47 (t, J=7.1 Hz, 2H, PHCOO-m), 7.60 (t, J=7.1 Hz, PhCOO-p), 8.10 (d, J=7.1 Hz, PhCOO-o).

Diol 35. A solution of 34 (P$_7$=BOM, P$_{13}$=TBS) (16.3 mg, 0.0199 mmol) in (0.5 mL) was added to tris(diethylamino)sulfoniumdifluorotrimethylsilicate (TASF) (37 mg, 0.134 mmole) at room temperature under nitrogen atmosphere. The solution was stirred for 40 m, diluted with ethyl acetate, poured into 20 mL of a saturated aqueous NaHCO$_3$ solution and extacted with CHCl$_3$ (30 mL×3). The combined organic phase was dried over anhydrous Na$_2$SO$_4$ and concentrated under reduced pressure to give 16 mg of a pale yellow oil, which was filtered through a pad of silica gel using 70% ethyl acetate/hexane as eluent. The filtrate was concentrated to yield 13.5 mg (94%) of 7-BOM BIII (35).

35 (P$_7$=BOM) mp. 224–225° C., $^1$H NMR (500 MHz, CDCl$_3$), δ 1.08 (s, 3H, CH$_3$ 17), 1.18 (s, 3H, CH$_3$ 16), 1.61 (s, 1H, OH1), 1.77 (s, 3H, CH$_3$ 19), 1.99 (ddd, J=2, 10.5, 14.5 Hz, 1H, H6β), 2.02 (d, J=5 Hz, 1H, OH13), 2.10 (d, J=1.5 Hz, 3H, CH$_3$ 18), 2.20 (s, 3H, AcO), 2.28 (s, 3H, AcO), 2.27–2.29 (m, 2H, H14), 2.89 (ddd, J=7, 10, 16.5 Hz, 1H, H6α), 3.94 (d, J=7 Hz, 1H, H3), 4.16 (dd, J=1, 8.5 Hz, 1H, H20β), 4.24 (dd, J=6.5, 10.5 Hz, 1H, H7), 4.31 (d, J=8 Hz, 1H, H20α), 4.45 (d, J=12.0 Hz, 1H, OCH$_2$Ph), 4.67 (d, J=12.0 Hz, 1H, OCH$_2$Ph), 4.84 (d, J=5 Hz, 1H, OCH$_2$O), 4.86 (d, J=5 Hz, 1H, OCH$_2$O), 4.87 (m, 1H, H13β), 4.95 (dd, J=2.0, 9.5 Hz, 1H, H5α), 5.63 (d, J=7 Hz, 1H, H2β), 6.40 (s, 1H, H10α), 7.30 (m, 5H, PhCH$_2$), 7.48 (m, 2H, PhCOO-m), 7.61 (m, 1H, PhCOO-p), 8.10 (2H, m, PhCOO-o). $^{13}$C NMR (CDCl$_3$) δ (ppm) 10.3, 14.9, 20.0, 20.7, 22.4, 26.6, 35.3, 38.4, 42.7, 47.2, 57.4, 67.8, 69.9, 74.6, 75.8, 76.4, 78.7, 80.3, 80.3, 80.9, 84.4, 96.7, 127.7, 127.9, 128.5, 128.8, 129.6, 130.3, 132.4, 133.8, 138.0, 144.4, 167.3, 169.8, 171.0, 203.0. IR (CHCl$_3$) ν 1720, 1460 cm$^{-1}$. Anal. Calcd. for C$_{39}$H$_{46}$O$_{12}$: C, 66.28; H, 6.56. Found C, 66.09; H, 6.59.

7-BOM-Taxol. To a solution of 7-BOM baccatin III (35) (13.2 mg, 0.018 mmol) in 0.25 mL of THF at −45° C. was added dropwise 21 μL of a 1.03 M solution of lithium bis(trimethyisilyl)amide in THF. After 1 h at −45° C., a solution of (S)-cis-1-benzoyl-3-triethylsilyloxy-4-azetidin-2-one (15 mg, 0.039 mmnol) in 0.25 mL of THF was added dropwise to the mixture. The solution was warmed to 0° C. and kept at that temperature for 1 h before 0.2 mL of a 10% solution of AcOH in THF was added. The mixture was partitioned between saturated aqueous NaHCO$_3$ and 60% ethyl acetate/hexane. Evaporation of the organic layer gave a residue which was purified by filtration through silica gel to give 20.2 mg of crude (2'R,3'S)-2'-triethylsilyl-7-BOM taxol.

To a solution of 20.2 mg (0.018 mmol) of (2'R,3'S)-2'-triethylsily-7-BOM taxol in 0.8 mL of acetonitrile and 0.3 mL of pyridine at 0° C. was added 0.10 mL of 48% aqueous HF. The mixture was sired at 0° C. for 1 h and then partitioned between saturated aqueous sodium bicarbonate and ethyl acetate. Evaporation of the ethyl acetate solution gave 17.7 mg of material which was purified by flash chromatography to give 15.4 mg (86%) of 7-BOM-taxol.

7-BOM-Taxol: m.p 169–172° C., $^1$H NMR (CDCl$_3$, 300 MHz) δ 8.11 (d, J=7.1 Hz,2H, benzoate ortho), 7.76 (d, J=7.1 Hz, 1H, benzamide ortho), 7.61–7.26 (m, 11 H, aromatic), 7.06 (d, J=8.8 Hz, 1H, NH), 6.33 (s, 1H, H10), 6.17 (dd, J=8.8, 8.8 Hz, 1H, H13), 5.79 (dd, J=8.8, 2.2 Hz, 1H, H3'), 5.67 (d, J=6.6 Hz, 1H, H2b), 4.91 (d, J=8.8 Hz, 1H, H5), 4.87–4.77(m, 3H, H2', OCH2Ph), 4.67 (d, J=12 Hz, OCH20) 4.43 (d, J=12 Hz, OCH20), 4.30 (d, J=8.2 Hz, H, H20α), 4.19 (d, J=8.2 Hz, 1H, H20b), 4.15 (m, 1H, H7), 3.70 (d, J=6.6 Hz, 1H, H3), 3.61 (d, J=2.5 Hz, 1H, 2'OH), 2.85 (m, 1H, H6α), 2.35 (s, 3H, 4Ac), 2.30 (m, 2H, H14), 2.19 (s, 3H, 10AC), 2.05 (m, 1H, H6b), 1.78 (br s, 6H, Me18, Me19), 1.72 (s, 1H, 10H), 1.19 (br s, 6H, Me16, Me17). Anal. Calcd. for C$_{55}$H$_{59}$O$_{15}$×0.5H$_2$O: C, 67.20; H, 6.15. Found C, 67.08; H, 6.16.

Taxol. To a suspension of 10% Pd on carbon (50 mg) in ethanol (0.6 mL) saturated with hydrogen at room temperature was added a solution of 7-BOM-taxol (14.4 mg, 0.0148 mmol) in ethanol (0.2 mL×4). The reaction mixture was refluxed for 45 min under hydrogen and then filtered through silica gel eluting with ethyl acetate. The solvent was evaporated under reduced pressure to give 11.9 mg of taxol (94%) as colorless needles, which exhibited spectra identical with an authentic sample of taxol.

Taxol: mp. 210–212° C., $^1$H NMR (500 MHz, CDCl$_3$) δ 1.15 (s, 3H, CH$_3$ 16), 1.24 (s, 3H, CH$_3$ 17), 1.68 (s, 3H, CH$_3$ 19), 1.75 (s, 1H, OH1), 1.79 (s, 3H, CH$_3$ 18), 1.90 (ddd, J=14.6, 11.0, 2.3 Hz, 1H, H6β), 2.26 (s, 3H, AcO10), 2.33 (dd, J=15.4, 8.9 Hz, 1H, H14β), 2.38 (dd, J=15.4, 8.9 Hz, 1H, H14α), 2.41 (s, 3H, AcO4), 2.46 (d, J=4.1 Hz, 1H, OH7), 2.57 (ddd, J=10.0, 14.6, 6.5 Hz, 1H, H6α), 3.54 (d, J=5.0 Hz, 1H, OH2'), 3.82 (d, J=6.9 Hz, 1H, H3α), 4.22 (d, =8.5 Hz, 1H, H20α), 4.32 (d, J=8.5 Hz, 1H, H20β), 4.42 (ddd, J=11.0, 6.5, 4.1 Hz, 1H, H7α), 4.81 (dd, J=5.0, 2.5 Hz, 1H, H2'), 4.96 (dd, J=10.0, 2.3 Hz, 1H, H5α), 5.69 (d, J=6.9 Hz, 1H, H2β), 5.81 (dd, J=8.7, 2.5 Hz, 1H, H3'), 6.25 (dd, J=8.9, 8.9 Hz, 1H, H13β), 6.29 (s, 1H, H10α), 6.98 (d, J=8.7 Hz, 1H, NH), 7.37 (m, 1H, PhCON-p), 7.46 (m, 9H, Ph 3', PhCOO 2'-m, PhCON-m), 7.62 (m, 1H, PHCOO-p), 7.76 (br d, J=8.7 Hz, 1H, PhCON-o), 8.16 (br d, J=7.3 Hz, 1H, PhCOO-o). IR (CHCl$_3$) ν 2730, 1650 cm$^{-1}$.

10Deacetyl baccatin III (36). To a mixture of ketone 33 (P$_7$=MOP, P$_{13}$=TES) (2.2 mg, 0.003 mmol) in pyridine (30 μL, 0.36 mmol) and acetonitrile (20 μL) at 0° C. was added 48% aqueous HF (12 μL, 0.32 mmol) and the solution was then warmed to room temperature and stirred for 36 hours. The mixture was then diluted with 2 mL of ethyl acetate and poured in to a separatory funnel containing 30 mL of aqueous saturated Na$_2$CO$_3$ and 20 mL ethyl acetate. The aqueous layer was extracted twice with 20 mL of ethyl acetate and the organic layers were combined, dried with Na$_2$SO$_4$, filtered, and concentrated to give 2.7 mg of a yellow oil. The material was purified by plug silica gel column chromatography by eluting with a 50% ethyl acetate/hexanes mixture followed by ethyl acetate to give 1.5 mg of 36, which exhibited spectra identical with an authentic sample of 10-DAB.

Baccatin III (37). To a mixture of ketone 34 (P$_7$=MOP) (2.1 mg, 0.003 mmol) in pyridine (30 μL, 0.36 mmol) and acetonitrile (20 μL) at 0° C. was added 48% aqueous HF (12 μL, 0.32 mmol) and the solution was then warmed to room temperature and stirred for 36 hours. The mixture was then diluted with 2 mL of ethyl acetate and poured in to a separatory funnel containing 30 mL of aqueous saturated $Na_2CO_3$ and 20 mL ethyl acetate. The aqueous layer was extracted twice with 20 mL of ethyl acetate and the organic layers were combined, dried with $Na_2SO_4$, filtered, and concentrated to give 2.7 mg of a yellow oil. The material was purified by plug silica gel column chromatography by elutng with an ethyl acetate/hexanes mixture to give 1.7 mg of 37, which exhibited spectra identical with an authentic sample of baccatin III.

REACTION SCHEME A'

Hydroxyketone 19. To a vigorously stirTed solution of ketone 18 ($P_7$=MOP) (181 mg, 0.265 mmol) in THF (2.2 mL) under nitrogen at −78° C. was added dropwise down the side of the flask 2.13 mL of a 0.2 M solution (0.426 mmol) of LDA in THF. After 10 min, a solution of 116 mg of (S)-camphorsulfonyloxaziridine (116 mg, 0.396 mmol) in 1.5 mL THF was added dropwase down the side of the flask. The reaction mixture was cooled to 40° C. and, after stirring 1 h, 2 mL of a saturated aqueous $NaHCO_3$ solution was added. The reaction mixture was diluted with 50 mL of 30% ethyl acetate in hexanes and washed with 20 mL of a saturated aqueous $NaHCO_3$ solution and brine, dried over anhydrous $Na_2SO_4$ and concentrated under reduced pressure. The resulting oil was filtered through silica gel with 30% ethyl acetate in hexanes and concentrated to give 210 mg of a colorless oil. This material was purified by radial chromatography, eluting with 25% ethyl acetate in hexanes to yield 150 mg (81%) 5β-hydroxyketone 19 as a white solid, 15 mg (8%) returned starting ketone 18 and 10 mg (5%) of the corresponding 5α-hydroxyketone.

19 ($P_7$=MOP): $^1$H NMR (500 MHz, $CDCl_3$) δ 0.08 (s, 3H, TBS $CH_3$), 0.12 (s, 3H, TBS $CH_3$), 0.62 (q, J=8.2 Hz, 6H, TES $CH_2$), 0.90 (s, 9H, TBS t-Bu), 0.96 (t, J=8.2 Hz, 9H, TES $CH_3$), 1.05 (s, 3H, $CH_3$ 19), 1.19 (s, 3H, $CH_3$ 17), 1.33 (s, 3H, $CH_3$ 16), 1.35 (s, 3H, MOP $CH_3$), 1.43 (s, 3H, MOP $CH_3$), 1.67 (dd, J=5.0, 14.7 Hz, 1H, H9β), 1.87 (m, 1H, H6β), 2.12 (dd, J=4.1, 15.1 Hz, 1H, H14α), 2.14 (d, J=1.4 Hz, 3H, $CH_3$ 18), 2.23 (dd, J=7.3, 14.7 Hz, 1H, H9α), 2.55 (dd, J=9.2, 15.1 Hz, 1H, H14β), 2.76 (ddd, J=3.7, 7.3, 13.7 Hz, 1H, H6α), 3.22 (s, 3H, MOP $OCH_3$), 3.24 (d, J=4.1 Hz, 1H, OH5), 3.28 (d, J=6.0 Hz, 1H, H3α), 3.83 (dd, J=3.7, 9.2 Hz, 1H, H7α), 4.06 (ddd, J=4.1, 7.3, 7.3 Hz, 1H, H5α), 4.46 (dd, J=5.0, 7.3 Hz, 1H, H10β), 4.53 (d, J=6.0 Hz, 1H, H2β), 4.63 (dd, J=2.8, 9.2 Hz, 1H, H13β).

Ketone 20. To a vigorously stirred solution of 5-hydroxy-4-ketone 19 ($P_7$=MOP) (420 mg, 0.602 mmol) in $CH_2Cl_2$ (20 mL) and triethylamine (1.18 mL, 8.5 mmol) under nitrogen at 0° C. was added trimethylsilychloride (0.40 mL, 3.3 mmol). After 0.5 h, the reaction mixture was quenched with 5 mL of a saturated aqueous $NaHCO_3$ solution and extracted with 50 mL $CHCL_3$. The organic phase was washed with brine, dried over anhydrous $Na_2SO_4$ and concentrated under reduced pressure to give 453 mg (98%) of ketone 20 as a colorless oil. This material was used without further purification.

20 ($P_7$=MOP): $^1$H NMR (500 MHz, $CDCl_3$) δ 0.11 (s, 6H, TBS $CH_3$), 0.12 (s, 9H, TMS $CH_3$), 0.59 (q, J=7.8 Hz, 6H, TES $CH_2$), 0.94 (s, 9H, TBS t-Bu), 0.96 (t, J=7.8 Hz, 9H, TES $CH_3$), 1.23 (s, 3H, $CH_3$ 17), 1.32 (s, 3H, $CH_3$ 19), 1.33 (s, 3H, MOP $CH_3$), 1.35 (s, 3H, $CH_3$ 16), 1.37 (s, 3H, MOP $CH_3$), 1.86 (m, 3H, H6β, H9α, H9β), 2.05 (d, J=1.4 Hz, 3H, $CH_3$ 18), 2.43 (d, J=3.7 Hz, 1H, H14β), 2.45 (d, J=4.6 Hz, 1H, H14α), 2.59 (ddd, J=6.0, 8.2, 14.2 Hz, 1H, H6α), 2.84 (d, J=6.0 Hz, 1H, H3α), 3.21 (s, 3H, MOP OMe), 3.51 (dd, J=6.0, 11.0 Hz, 1H, H7α), 3.94 (dd, J=4.1, 8.2 Hz, 1H, H5α), 4.38 (dd, J=5.0, 8.7 Hz, 1H, H10β), 4.54 (d, J=6.0 Hz, 1H, H2β), 4.74 (dd, J=6.4, 6.4 Hz, 1H, H13β).

Diol 21. To a stirred solution of ketone 20 ($P_7$=MOP) (453 mg, 0.588 mmol) in THF (23 mL) under nitrogen at −78° C. was added dropwise 1.95 mL of a 3 M solution of MeMgBr in ether (5.85 mmol). The reaction mixture was stirred for 5.5 h, poured into 100 mL of a saturated aqueous $NaHCO_3$ solution and extracted with three 100 mL portions of $CHCl_3$. The combined organic phases were dried over anhydrous $Na_2SO_4$ and concentrated under reduced pressure to yield 453 mg of the hydroxy trimethylsilyl ether as a colorless oil. This material was used without further purification.

To a stirred solution of the trimethylsilyl ether (453 mg) in pyridine (8 mL) and acetonitrile (8 mL) at 0° C. was added 0.8 mL of a 48% aqueous HF solution. After stirring 20 min, the resulting mixture was poured into 100 mL of a saturated aqueous $NaHCO_3$ solution and extracted with three 150 mL portions of $CHCl_3$. The combined organic layers were dried over anhydrous $Na_2SO_4$ and concentrated under reduced pressure to yield 422 mg of diol 21. This material used without further purification.

21 ($P_7$=MOP): $^1$H NMR (300 MHz, $CDCl_3$) δ 0.08 (s, 3H, TBS $CH_3$), 0.10 (s, 3H, TBS $CH_3$), 0.56 (q, J=7.7 Hz, 6H, TES $CH_2$), 0.90 (s, 9H, TBS t-Bu), 0.93 (t, J=7.7 Hz, 9H, TES $CH_3$), 1.16 (s, 3H, $CH_3$ 17), 1.25 (s, 3H, $CH_3$ 16), 1.29 (s, 3H, $CH_3$ 19), 1.31 (s, 3H, $CH_3$ 20), 1.38 (s, 3H, MOP $CH_3$), 1.46 (s, 3H, MOP $CH_3$), 1.81 (d, J=3.8 Hz, 1H, H3α), 1.86 (d, J=9.9 Hz, 1H, H9β), 1.90 (dd, J=6.1, 8.3 Hz, 1H, H9α), 1.96 (s, 3H, $CH_3$ 18), 2.12 (ddd, J=3.3, 3.3, 10.4 Hz, 1H, H6α), 2.30 (m, 1H, H6β), 2.42 (dd, J=3.9, 15.4 Hz, 1H, H14α), 2.61 (dd, J=9.3, 15.4 Hz, 1H, H14β), 2.81 (s, 1H, OH4), 3.04 (m, 1H, OH5), 3.40 (dd, J=3.9, 15.8 Hz, 1H, H7α), 4.28 (dd, J=6.6, 8.2 Hz, 1H, H10β), 4.62 (dd, J=1.6, 7.8 Hz, 1H, H13β), 4.66 (d, J=3.8, 1H, H2β).

Acetate 22. To a stirred soluton of diol 21 ($P_7$=MOP) (470 mg, 0.66 mmol) in pyridine (12 mL) under nitrogen at room temperature was added acetic anhydride (4.5 mL). After 11 h, the reaction mixture was diluted with 50 mL of $CHCl_3$, then poured into 50 mL of saturated aqueous sodium bicarbonate solution. The aqueous phase was extracted with $CHCl_3$ then the combined extracts were washed with brine, dried with $Na_2SO_4$ and filtered. Concentration of the filtrate under vacuum yielded 470 mg (94% from 20) of crude material which was pure acetate 22 by $^1$H NMR and TLC analysis.

22 ($P_5$=Ac, $P_7$=MOP): $^1$H NMR (500 MHz, $CDCl_3$) δ 0.10 (s, 3H, TBS $CH_3$), 0.13 (s, 3H, TBS $CH_3$), 0.59 (q, J=7.8 Hz, 6H, TES $CH_2$), 0.94 (s, 9H, TBS t-Bu), 0.95 (t, J=7.8 Hz, 9H, TES $CH_3$), 1.18 (s, 3H, $CH_3$ 17), 1.30 (s, 3H, $CH_3$ 16), 1.32 (s, 3H, $CH_3$ 19), 1.33 (s, 6H, $CH_3$ 20, MOP $CH_3$), 1.41 (s, 3H, MOP $CH_3$), 1.91 (d, J=3.4 Hz, 1H, H3α), 1.94 (m, 2H, H9, H9), 2.00 (d, J=1.5 Hz, 3H, $CH_3$ 18), 2.06 (ddd, J=3.9, 3.9, 11.7 Hz, 1H, H6α), 2.10 (s, 3H, OAc), 2.14 (dd, J=11.7, 23.9 Hz, 1H, H6β), 2.38 (dd, J=3.9, 15.1 Hz, 1H, H14α), 2.63 (dd, J=9.3, 15.1 Hz, 1H, H14β), 2.78 (d, J=1.5 Hz, 1H, OH4), 3.20 (s, 3H, OMe $CH_3$), 3.38 (dd, J=3.9, 11.7 Hz, 1H, H7α), 4.30 (dd, J=4.9, 10.3 Hz, 1H, H10β), 4.50 (ddd, J=1.5, 3.9, 12.2 Hz, 1H, H5α), 4.64 (dd, J=1.5, 1.5 Hz, 1H, H13β), 4.66 (d, J=3.4 Hz, 1H, H2β).

Olefin 23. To a stirred solution of alcohol 22 ($P_5$=Ac, $P_7$=MOP) (26 mg, 0.034 mmol) in $CH_2Cl_2$ (1.48 mL) and pyridine (0.37 mL) under nitrogen at 10° C. was added SOCl$_2$ (0.037 mL, 5.1 mmol) over a period of three minutes. The mixture was warmed to room temperature and stirred for 2.3 h then diluted with CHCl$_3$ and poured into saturated aqueous sodium bicarbonate solution. The aqueous phase was extracted with CHCl$_3$ and the combined extracts were washed with brine, dried over anhydrous Na$_2$SO$_4$ and filtered. Concentration of the filtrate under vacuum yielded 24 mg of crude material which was purified by silica gel chromatography to give 13 mg (52%) of a 4:1 mixture of 7-MOP-ex;endo cyclic olefins and 6 mg (27%) of a 4:1 mixture of 7-hydroxy-exo;endo cyclic olefins.

23 (P$_5$=Ac, P$_7$=MOP): $^1$H (500 MHz, CDCl$_3$) δ 0.10 (s, 3H, TBS CH$_3$), 0.12 (s, 3H, TBS CH$_3$), 0.59 (q, J=7.9, 6H, TES CH$_2$), 0.93 (s, 9H, TBS t-Bu), 0.96 (t, J=7.9, 9H, TES CH$_3$), 1.21 (s, 3H, CH$_3$ 17), 1.30 (s, 3H, CH$_3$ 19), 1.32 (s, 3H, MOP CH$_3$), 1.34 (s, 3H, MOP CH$_3$), 1.37 (s, 3H, CH$_3$ 16), 1.72 (m, 2H, H6β, H9β), 1.89 (dd, J=3.8, 13.4 Hz, 1H, H9β), 2.03 (d, J=1.37 Hz, 3H, CH$_3$ 18), 2.05 (s, 3H, OAc CH$_3$), 2.33 (dd, J=5.1, 15.4 Hz, 1H, H14α), 2.47 (m, 2H, H6α, H14β), 3.06 (d, J=5.8 Hz, 1H, H3α), 3.20 (s, 3H, MOP OMe), 3.38 (dd, J=6.9, 11.0 Hz, 1H, H7α), 4.37 (dd, J=3.8, 11.0 Hz, 1H, H10β), 4.53 (d, J=5.8 Hz, 1H, H2β), 4.74 (m, 1H, H13β), 5.15 (s, 1H, H20E), 5.21 (d, J=1.37 Hz, 1H, H20Z), 5.36 (d, J=9.3 Hz, 1H, H5α).

Diol 24. To a stirred solution of a 4:1 mixture of the exo,endocyclic olefins 23 (P$_5$=Ac, P$_7$=MOP) (249 mg, 0.337 mmol) in pyridine (4.6 mL) under nitrogen at 0° C. was added 2.35 mL of a 0.157 M solution (0.368 mmol) of OsO$_4$ in THF. After 1 h, NaHSO$_3$ was added along with 6.2 mL of water and the mixture was stirred for 1 h at room temperature. The mixture was then diluted with ethyl acetate and poured into saturated aqueous sodium bicarbonate. The aqueous layer was extracted with ethyl acetate and the combined extracts were washed with brine, dried over anhydrous Na$_2$SO$_4$ and concentrated under reduced pressure to yield 281 mg of crude material which was purified by silica gel chromatography, eluting with 50% ethyl acetate/hexane to yield 190 mg (73%) of pure diol 24 and 48 mg (19%) of the enol acetate.

24 (P$_5$=Ac, P$_7$=MOP): $^1$H NMR (500 MHz, CDCl$_3$) δ 0.10 (s, 3H, TBS CH$_3$), 0.11 (s, 3H, TBS CH$_3$), 0.60 (dq, J=1.5, 7.8 Hz, 6H, TES CH$_2$), 0.87 (s, 3H, CH$_3$ 19), 0.93 (s, 9H, TBS t-Bu), 0.95 (t, J=7.8 Hz, 9H, TES CH$_3$), 1.20 (s, 3H, CH$_3$ 17), 1.31 (s, 3H, CH$_3$ 16), 1.33 (s, 3H, MOP CH$_3$), 1.47 (s, 3H, MOP CH$_3$) 1.54 (dd, J=12.3, 25.0 Hz, 1H, H6β), 1.63 (dd, J=5.5, 15.1 Hz, 1H, H9β), 2.05 (s, 3H, OAc), 2.15 (s, 3H, CH$_3$ 18), 2.26 (m, 2H, H9α, OH20) 2.37 (dd, J=9.2, 14.7 Hz, 1H, H14β), 2.46 (ddd, J=4.8, 4.8, 13.4 Hz, 1H, H6α), 2.69 (d, J=4.5 Hz, 1H, H3α), 3.18 (s, 3H, MOP CH$_3$), 3.28 (dd, J=3.8, 14.7 Hz, 1H, H14α), 3.76 (dd, J=4.0, 11.6 Hz, 1H, H7α), 3.84 (m, 2H, H20, H20), 3.95 (s, 1H, OH4), 4.42 (dd, J=5.1, 5.8 Hz, 1H, H10β), 4.44 (d, J=4.1 Hz, 1H, H2β), 4.63 (dd, J=4.1, 12.3 Hz, 1H, H5α), 4.67 (dd, J=4.1, 9.2 Hz, 1H, H13β).

24 (P$_7$=BOM: $^1$H NMR (300 MHz, CDCl$_3$) δ 0.09 (s, 3H, TBS CH$_3$), 0.10 (s, 3H, TBS CH$_3$), 0.58 (q, J=7.9 Hz, 2H, TES CH$_2$), 0.83 (s, 3H, CH$_3$ 19), 0.92 (s, 9H, TBS t-Bu), 0.93 (t, J=7.9 Hz, TES CH$_3$), 1.20 (s, 3H, CH$_3$ 17), 1.33 (s, 3H, CH$_3$ 16), 1.58 (q, J=13.2 Hz, 1H, H6β), 1.71 (dd, J=10.4, 5.5 Hz, H9β), 2.04 (s, 3H, OAc), 2.17 (br s, 3H, CH$_3$ 18), 2.20 (dd, J=10.4, 3.8 Hz, 1H, H9α), 2.35 (dd, J=14.8, 9.1 Hz, 1H, H14β), 2.43 (dt, J=13.2, 5.0 Hz, 1H, H6α), 2.80 (d, J=4.6 Hz, 1H, H3 α), 3.31 (dd, J=4.4, 14.8 Hz, 1H, H14α), 3.71 (dd, J=4.9, 13.0 Hz, 1H, H7α), 3.83 (m, 2H, H20), 3.98 (s, 1H, OH1), 4.46 (d, J=4.8 Hz, 1H, H2β), 4.48 (m, 1H, H10β), 4.51 (d, J=12.1 Hz, 1H, PhCH$_2$O), 4.64 (dd, J=13.2, 5.0 Hz, 1H, H5α), 4.66 (m, 1H, H13β), 4.70 (d, J=12.1 Hz, 1H, PhCH$_2$O), 4.83 (d, J=7.1 Hz, 1H, OCH$_2$O), 4.94 (d, J=7.1 Hz, 1H, OCH$_2$O), 7.33 (m, 5H, Ph).

Triol 25. To a stirred soluton of acetoxydiol 24 (P$_5$=Ac, P$_7$=MOP) (26.5 mg, 0.035 mmol) in anhydrous methanol (0.9 mL) at −5° C. under nitrogen was added 0.060 mL of a 0.166 M (0.01 mmol) methanolic solution of sodium methoxide. After 2.5 h, the reaction mixture was diluted with 10 mL of ethyl acetate, then poured into 10 mL of a saturated aqueous NaHCO$_3$ solution. The organic phase was washed with 10 mL of a saturated aqueous NaHCO$_3$ solution, dried over anhydrous Na$_2$SO$_4$ and concentrated under reduced pressure to give 25 mg of pure triol 25 (100%).

25 (P$_7$=MOP): $^1$H NMR (500 MHz, CDCl$_3$) δ 0.10 (s, 3H, TBS CH$_3$), 0.11 (s, 3H, TBS CH$_3$), 0.60 (q, J=8.06 Hz, 6H, TES CH$_2$), 0.87 (s, 3H, CH$_3$ 19), 0.94 (s, 9H, TBS t-Bu), 0.95 (t, J=8.1 Hz, 9H, TES CH$_3$), 1.19 (s, 3H, CH$_3$ 17), 1.31 (s, 3H, CH$_3$ 16), 1.33 (s, 3H, MOP CH$_3$), 1.47 (s, 3H, MOP CH$_3$), 1.59 (dd, J=11.7, 11.7 HZ, 1H, H6β), 1.62 (dd, J=5.5, 16.1 HZ, 1H, H9β), 2.11 (dt, J=0.7 Hz, 3H, CH$_3$ 18), 2.24 (dd, J=5.5, 16.1 Hz, 1H, H9α), 2.38 (dd, J=9.5, 15.0 Hz, 1H, H14β), 2.45 (ddd, J=4.4, 4.4, 13.6 Hz, 1H, H6α), 2.60 (d, J=4.4 Hz, 1H, H3α), 3.21 (s, 3H, MOP OMe), 3.25 (dd, J=4.4, 15.0 Hz, 1H, H14α), 3.52 (dd, J=4.4, 12.8 Hz, 1H, H7α), 3.72 (dd, J=4.4, 11.4 Hz, 1H, H5α), 3.79 (s, 1H, OH4), 3.86 (d, J=11.0, 1H, H20), 3.93 (d, J=11.4 Hz, 1H, H20), 4.42 (dd, J=5.1, 5.1 Hz, 1H, H10β), 4.45 (d, J=4.4 Hz, 1H, H2β), 4.66 (dd, J=4.0, 9.2 Hz, 1H, H13β).

p-Methoxybenzylidene acetal 25b: To a solution of the diol 24 (P$_5$=Ac, P$_7$=BOM) (6.5 mg, 0.0079 mmol) and anisaldehyde dimethyl acetal (0.013 ml, 0.076 mmol) stirred in CH$_2$Cl$_2$ was added a solution of p-toluenesulfonic acid (0.002 ml, 0.1M in THF, 0.0002 mmol). The resulting solution was stirred at room temperature for 15 min then triethylamine (0.1 ml) was added and stirring was continued for 10 min. The mixture was rinsed into 30% ethyl acetate in hexanes (15 ml) then the aqueous phase was extracted with 30% ethyl acetate in hexanes (2×5 ml). The combined extracts were washed with brine, dried over Na$_2$SO$_4$, and filtered. Concentration of the filtrate under vacuum yielded 12 mg of colorless oil which was purified by silica gel chromatography to yield 6.9 mg (96%) of p-methoxybenzylidene acetal 25b as a 5:1 mixture of diasteromers.

25b (P$_5$=Ac, P$_7$=BOM, major diasteromer): $^1$H NMR (500 MHz, CDCl$_3$) δ −0.05 (s, 3H, TBS CH$_3$), 0.07 (s, 3H, TBS CH$_3$), 0.60 (q, J=7.9 Hz, 2H, TES CH$_2$), 0.78 (s, 3H, CH$_3$ 19) 0.82 (s, 9H, TBS t-Bu), 0.95 (t, J=7.9 Hz, TES CH$_3$), 1.25 (s, 3H, CH$_3$ 17), 1.37 (s, 3H, CH$_3$ 16), 1.58 (m, H6β), 1.70 (dd, J=16.8, 5.8 Hz, H9β), 1.74 (s, 3H, OAc), 2.26 (s, 3H, CH$_3$ 18), 2.28 (dd, J=16.8, 1.4 Hz, 1H, H9α), 2.38 (dd, J=15.1, 9.7 Hz, 1H, H14β), 2.57 (dt, J=5.1, 9.9 Hz, 1H, H6α), 3.10 (dd, J=5.1, 14.7 Hz, 1H, H14α), 3.11 (d, J=4.8 Hz, 1H, H3α), 3.79 (s, 3H, OCH$_3$), 3.84 (dd, J=5.0, 11.5 Hz, 1H, H7α), 4.15 (d, J=8.2 Hz, 1H, H20), 4.20 (d, J=8.2 Hz, 1H, H20), 4.48 (d, J=12.0 Hz, 1H, OCH$_2$Ph), 4.55 (d, J=4.8 Hz, 1H, H2β), 4.57 (m, 1H, H10β), 4.71 (d, J=12.0 Hz, 1H, OCH$_2$Ph), 4.73 (m, 1H, H13β), 4.78 (dd, J=12.4, 4.9 Hz, 1H, H5α), 4.84 (d, J=6.7 Hz, 1H, OCH$_2$O), 4.99 (d, J=6.7 Hz, 1H, OCH$_2$O), 6.05 (s, 1H, acetal CH), 6.80 (d, J=7.5 Hz, 2H, p-MeOPh-o), 7.27–7.36 (m, 7H, p-MeOPh-m and Ph).

Acetonide 26b. To a solution of the p-methoxybenzylidene acetal 25b (P$_5$=Ac, P$_7$=BOM) (11.5 mg, 0.012 mmol) in 0.4 mL of toluene stirred at 0° C. was added a solution of diisobutylaluminum hydride (0.082 ml, 2.0M in toluene, 0.12 mmol). The resulting solution was stirred for 3.5 h then methanol (0.1 ml) was added. The mixture was diluted with ethyl acetate (5 ml) and stirred with saturated aqueous sodium potassium tartrate for 1.5 hours. The aqueous phase was separated and extracted with ethyl acetate (2×10 ml) then the combined extracts were washed with brine and dried with $Na_2SO_4$. Filtration followed by concentration of the filtrate under vacuum yielded 12 mg of crude material that was purified by silica gel chromatography (30% ethyl acetate in hexanes eluent) to yield 4.7 mg of a mixture of formate acetals, 1.1 mg of 4-MPM-1,2,5,20-tetraol, and 5.2 mg of a mixture of formate p-methoxybenzyl ethers.

The mixture of formate acetals was dissolved in methanol (0.1 ml) and 3% aqueous $NH_4OH$ was added. The cloudy mixture was stirred at room temperature for 30 min then rinsed into ethyl acetate over saturated aqueous $NaHCO_3$. The aqueous phase was extracted with ethyl acetate (2×10 ml) and the combined extracts were washed with brine, dried over $Na_2SO_4$, and filtered. Concentration of the filtrate under vacuum yielded a mixture of p-methoxybenzylidene acetals. The mixture of acetals was dissolved in toluene (0.4 ml) and the solution was cooled to 0° C. then a solution of diisobutylaluminum hydride (0.02 ml, 2.0M in toluene, 0.08 mmol) was added. The resulting solution was stirred for 3.5 hours then methanol (0.1 ml) was added. The mixture was diluted with ethyl acetate (5 ml) and stirred with saturated aqueous sodium potassium tartrate for 1.5 hours. The aqueous phase was separated and extracted with ethyl acetate (2×10 ml) and the combined extracts were washed with brine and dried over $Na_2SO_4$. Filtration followed by concentration of the filtrate under vacuum yielded 4.5 mg of crude material that was purified by silica gel chromatography (30% ethyl acetate in hexanes eluent) to yield 2.8 mg of 4-MPM-1,2,5,20-tetraol.

The mixture of formatae p-methoxybenzyl ethers was dissolved in methanol (0.1 ml) and 3% aqueous $NH_4OH$ (0.1 ml) was added. The cloudy mixture was stirred at room temperature for 30 minutes then rinsed into ethyl acetate over saturated aqueous $NaHCO_3$. The aqueous phase was extracted with ethyl acetate (2×10 ml) and the combined extracts were washed with brine, dried over $Na_2SO_4$, and filtered. Concentration of the filtrate under vacuum yielded 4.8 mg of crude material which was purified by silica gel chromatography to yield 3.2 mg of 4-MPM-1,2,5,20-tetraol. Total combined yield of 4-MPM-1,2,5,20-tetraol: 68% from 25b.

4-MPM-1,2,5,20-tetraol: $^1$H NMR (500 MHz, $CDCl_3$) δ 0.13 (s, 3H, TBS $CH_3$), 0.06 (s, 3H, TBS $CH_3$), 0.60 (q, J=8.0 Hz, 2H, TES $CH_2$), 0.89 (s, 9H, TBS t-Bu), 0.95 (t, J=8.0 Hz, TES $CH_3$), 0.97 (s, 3H, $CH_3$ 19), 1.22 (s, 3H, $CH_3$ 17), 1.30 (s, 3H, $CH_3$ 16), 1.83 (dd, J=16.8, 5.8 Hz, H9α), 1.91 (q, J=12.4 Hz, 1H, H6β), 2.12 (m, 2H, H9α and 14β), 2.18 (s, 3H, $CH_3$ 18), 2.55 (m, 2H, H14β and 6α), 2.79 (d, J=5.3 Hz, 1H, H3α), 2.95 (d, J=3.0 Hz, 1H, OH5), 3.54 (m, 1H, OH20), 3.66 (dd, J=10.3, 5.3 Hz, 1H, H2β), 3.81 (s, 3H, $OCH_3$), 3.85 (dd, J=5.2, 11.6 Hz, 1H, H7α), 3.91 (dt, J=5.9, 12.4, 1H, H5α), 4.18 (s, 1H, OH1), 4.13 (d, J=13 Hz, 1H, H20), 4.20 (dd, J=7.22, 12.9 Hz, 1H, H20), 4.47 (d, J=11.8 Hz, 1H, O$\underline{CH}_2$Ph), 4.58 (m, 1H, H10β), 4.79 (d, J=11.8 Hz, 1H, O$\underline{CH}_2$Ph), 4.85 (m, 1H, H13β), 4.87 (d, J=6.8 Hz, 1H, O$CH_2$O), 5.01 (d, J=10.6 Hz, 1H, MPM $\underline{CH}_2$), 5.10 (d, J=6.8 Hz, 1H, O$CH_2$O), 5.11 (d, J=10.6 Hz, 1H, MPM $\underline{CH}_2$), 5.49 (d, J=10.5 Hz, 1H, OH2), 6.87 (d, J=8.7 Hz, 2H), 7.30 (d, J=8.7 Hz, 2H, p-MeO$\underline{Ph}$-o), 7.27–7.36 (m, 5H, p-MeO$\underline{Ph}$-m and $\underline{Ph}$ $CH_2$).

To a solution of the 4-MPM-1,2,5,20-tetraol (2.0 mg, 0.0023 mmol) stirred in 0.2 ml of $CH_2Cl_2$ and 0.02 ml of 2,2-dimethoxypropane at 0° C. was added a solution of p-toluenesulfonic acid (0.002 ml, 0.1M in THF, 0.0002 mmol). The resulting solution was stirred for 20 min then triethylamine (0.1 ml) was added and stirring was continued for 10 min. The mixture was rinsed into ethyl acetate (10 ml) over saturated aqueous $NaHCO_3$ then the aqueous phase was extracted with ethyl acetate (2×5 ml). The combined extracts were washed with brine, dried with $Na_2SO_4$, and filtered. Concentration of the filtrate under vacuum yielded 2.1 mg of crude material which was purified by silica gel chromatography to yield 1.1 mg of acetonide 26b.

26b ($P_{520}$=C($CH_3$)$_2$, $P_7$=BOM): $^1$H NMR (500 MHz, $CDCl_3$) δ −0.073 (s, 3H, TBS $CH_3$), 0.008 (s, 3H, TBS $CH_3$), 0.60 (q, J=7.9 Hz, 6H, TES $CH_2$), 0.79 (s, 9H, TBS t-Bu), 0.95 (t, J=7.9 Hz, 9H, TES $CH_3$), 1.10 (s, 3H, $CH_3$ 19), 1.25 (s, 3H, $CH_3$ 17), 1.34 (s, 3H, $CH_3$ 16), 1.41 (s, 3H, $CH_3$ acetonide), 1.46 (s, 3H, $CH_3$ acetonide), 1.88 (dd, J=16.7, 5.5 Hz, H9β), 2.08 (dd, J=14.3, 9.2 Hz, 1H, H14β), 2.17 (s, 3H, $CH_3$ 18), 2.21 (dd, J=17.1, 1.7 Hz, 1H, H9α), 2.42 (dd, J=14.3, 7.2 Hz, 1H, H14α), 2.61 (d, J=5.1 Hz, 1H, H3α), 2.62 (m, 1H, H6β), 3.71 (dd, J=11.3, 5.1 Hz, 1H, H2β), 3.75 (dd, J=5.0, 11.3 Hz, 1H, H7α), 3.80 (s, 3H, $OCH_3$), 3.99 (dd, J=12.0, 6.2 Hz, 1H, H5α), 4.01 (d, J=14.2 Hz, 1H, H20), 4.17 (s, 1H, OH1), 4.44 (d, J=14.2 Hz, 1H, H20), 4.47 (d, J=11.6 Hz, 1H, O$\underline{CH}_2$Ph), 4.58 (m, 1H, H10β), 4.80 (d, J=11.6 Hz, 1H, O$\underline{CH}_2$Ph), 4.84 (d, J=11.3 Hz, 1H, OH2), 4.85 (m, 1H, H13β), 4.88 (d, J=10.3 Hz, 1H, O$CH_2$O), 4.89 (d, J=6.8 Hz, 1H, MPM $C\underline{H}_2$), 5.00 (d, J=10.3 Hz, 1H, O$C\underline{H}_2$Ph), 5.10 (d, J=6.8 Hz, 1H, MPM $C\underline{H}_2$), 6.85 (d, J=8.9 Hz, 2H, p-MeO$\underline{Ph}$-o), 7.27 (d, J=8.9 Hz, 2H, p-MeO$\underline{Ph}$-m), 7.27–7.36 (m, 5H, $\underline{Ph}$ $CH_2$).

Diolcarbonate 27b: To a solution of the diol 26b ($P_{520}$=C($CH_3$)$_2$, $P_7$=BOM) (1.1 mg) in 0.2 mL of $CH_2Cl_2$ and 0.02 mL of pyridine stirred at −78° C. was added a solution of phosgene (0.010 mL, 2M in toluene, 0.02 mmol). The resulting solution was stirred at −78° C. for 10 min then warmed to 0° C. for 3 h. The mixture was diluted with 30% ethyl acetate in hexanes (5 mL) then poured into 30% ethyl acetate in hexanes (10 mL) over saturated aqueous $NaHCO_3$. The aqueous phase was extracted with 30% ethyl acetate in hexanes (2×5 mL) then the combined extracts were washed with brine, dried with $Na_2SO_4$, and filtered. Concentration of the filtrate under vacuum yielded 1.3 mg of crude material. Purification by silica gel chromatography yielded 0.9 mg of pure 1,2-cyclic carbonate.

To a solution of the carbonate stirred in 0.1 ml of THF and 0.05 mL of methanol was added a solution of pyridinium tosylate (0.005 ml, 0.1M in $CH_2Cl_2$). The mixture was stirred at room temperature for 24 h and partitioned between saturated sodium bicarbonate and ethyl acetate. The ethyl acetate layer was dried over sodium sulfate and evaporated to give 0.9 mg of diol 27b.

27b ($P_7$=BOM): $^1$H NMR (500 MHz, $CDCl_3$) δ −0.24 (s, 3H, TBS $CH_3$), −0.038 (s, 3H, TBS $CH_3$), 0.58 (q, J=8.1 Hz, 6H, TES $CH_2$), 0.84 (s, 9H, TBS t-Bu), 0.93 (t, J=8.1 Hz, 9H, TES $CH_3$), 1.14 (s, 3H, $CH_3$ 19), 1.19 (s, 3H, $CH_3$ 17), 1.34 (s, 3H, $CH_3$ 16), 1.88 (br d, J=17 Hz, H9β), 2.00 (br q, J=12 Hz, 1H, H6β), 2.08 (d, J=1.4 Hz, 3H, $CH_3$ 18), 2.2 (m, 2H, H9α and 14β), 2.35 (br s, 1H, H3α), 2.39 (dt, J=4.8, 13 Hz, H6α), 2.74 (br s, 1H, 20 OH), 2.87 (dd, J=15.1, 5.1 Hz, 1H, H14α), 3.71 (dd, J=11.3, 5.1 Hz, 1H, H2β), 3.58 (br s, 2H, H7α and 20 OH), 3.78 (s, 3H, $OCH_3$), 3.78 (br m, 1H, H5α), 4.37 (dd, J=13.0, 5.8 Hz, 1H, H20) 4.39 (dd, J=4.8, 5.8 Hz, 1H, 10β), 4.47 (m, 2H, H20 and 2β), 4.59 (d, J=11.6 Hz, 1H, O$\underline{CH}_2$Ph), 4.63 (br m, 1H, H13β), 4.71 (d, J=11.6 Hz, 1H, O$\underline{CH}_2$Ph), 4.88 (d, J=7.2 Hz, 1H, O$CH_2$O), 4.91 (d, J=7.2 Hz, 1H, O$CH_2$O), 4.93 (m, 2H, MPM $C\underline{H}_2$), 6.84 (d, J=8.6 Hz, 2H, p-MeOPh-o), 7.23 (d, J=8.6 Hz, 2H, p-MeO Ph-m), 7.27–7.36 (m, 5H, Ph CH$_2$).

Mesylate 28b. To a stirred solution of diol 27b (0.9 mg) in pyridine (0.6 mL) under nitrogen at 0° C. was added dropwise methanesulfonyl chloride (0.02 mL). After 12 h, a saturated aqueous NaHCO$_3$ solution (0.05 mL) was added. The mixture was stirred for 10 min, poured into 20 mL of a saturated aqueous NaHCO$_3$ solution and extracted with 40% ethyl acetate/hexane (20 mL×3). The combined organic phase was dried over anhydrous Na$_2$SO$_4$ and concentrated under reduced pressure to give 1 mg of 28b as a colorless oil.

Oxetane 29. To a stirred solution of mesylate 28b (1 mg) in toluene (0.4 mL) under nitrogen at room temperature was added diisopropyl ethylamine (0.008 mL). The solution was refluxed for 3.5 h, cooled to room temperature, poured into 20 mL of a saturated aqueous NaHCO$_3$ solution and extracted with ethyl acetate (20 mL×3). The combined organic phase was dried over anhydrous Na$_2$SO$_4$, and concentrated under reduced pressure to give 1.5 mg of a pale yellow oil. The oil was column chromatographed (30% ethyl acetate/hexane) to yield 1 mg of MPM oxetane. This material was dissolved in 1 mL of methylene chloride, 0.1 mL of 0.1 M phosphate buffer and 1 mg of DDQ were added, and the mixture was stirred at ambient temperature for 2 h. The mixture was poured into 20 mL of a saturated aqueous NaHCO$_3$ solution and extracted with ethyl acetate (20 mL×3). The combined organic phase was dried over anhydrous Na$_2$SO$_4$, and concentrated under reduced pressure to give 1.0 mg of an oil. To a stirred solution of this material (1 mg) and dimethyl aminopyridine (1.5 mg) in pyridine (10 μL) under nitrogen at room temperature was added acetic anhydride (5 μL). The solution was stirred for 15 h, diluted with ethyl acetate, poured into 20 mL of a 10% aqueous CuSO$_4$ solution and extracted with ethyl acetate (20 mL×3). The combined organic phase was washed with a saturated aqueous NaHCO$_3$ solution, dried over anhydrous Na$_2$SO$_4$ and concentrated under reduced pressure to give 2 mg of a pale yellow oil. The oil was column chrometographed (25% ethyl acetate/hexane) to yield 0.6 mg of oxetane 29.

In view of the above, it will be seen that the several objects of the invention are achieved As various changes could be made in the above compositions without departing from the scope of the invention, it is intended that all matter contained in the above description be interpreted as illustrative and not in a limiting sense

What we claim is:

1. An intermediate for use in the preparation of a tricyclic or tetracyclic taxane having the formula

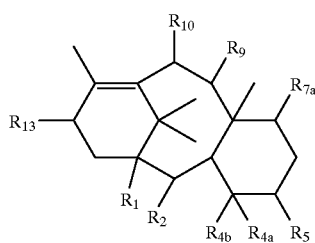

26a wherein

R$_1$ together with R$_2$ is a carbonate;

R$_{4a}$ is hydrogen, alkyl, hydroxy, protected hydroxy, or —OCOR$_{27}$, together with R$_{4b}$ is an oxo, or together with R$_2$, R$_{4b}$, or R$_5$ is a carbonate;

R$_{4b}$ is hydrogen, alkyl, alkenyl, alkynyl, aryl, heteroaryl, or cyano, together with R$_{4a}$ is an oxo, or together with R$_{4a}$ or R$_5$ is a carbonate;

R$_5$ is hydrogen, hydroxy, protected hydroxy, —OCOR$_{37}$, oxo, or together with R$_{40}$ or R$_{4b}$ is a carbonate;

R$_{7a}$ is hydrogen, halogen, hydroxy, protected hydroxy, —OR$_{28}$, or —OCOR$_{34}$, or together with R$_9$ is a carbonate;

R$_9$ is hydrogen, oxo, hydroxy, protected hydroxy, —OR$_{28}$, or —OCOR$_{33}$, or together with R$_{7a}$ or R$_{10}$ is a carbonate;

R$_{10}$ is hydrogen, oxo, hydroxy, protected hydroxy, —OR$_{28}$, or —OCOR$_{29}$, or together with R$_9$ is a carbonate;

R$_{13}$ is hydrogen, hydroxy, protected hydroxy, —OCOR$_{35}$, MO- or

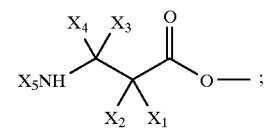

R$_{28}$ is a functional group which increases the solubility of the taxane derivative;

R$_{27}$, R$_{29}$, R$_{30}$, R$_{31}$, R$_{33}$, R$_{34}$, R$_{35}$ and R$_{37}$ are independently hydrogen, alkyl, alkenyl, alkynyl, alkoxy, aryloxy, —NX$_8$X$_{10}$, —SX$_{10}$, or monocyclic aryl or monocyclic heteroaryl;

X$_1$ is —OX$_5$, —SX$_7$, or —NX$_8$X$_9$;

X$_2$ is hydrogen, alkyl, alkenyl, alkynyl, aryl, or heteroaryl;

X$_3$ and X$_4$ are independently hydrogen, alkyl, alkenyl, alkynyl, aryl, or heteroaryl;

X$_5$ is —COX$_{10}$, —COOX$_{10}$, —COSX$_{10}$, —CONX$_8$X$_{10}$, or —SO$_2$X$_{11}$;

X$_6$ is hydrogen, alkyl, alkenyl, alkynyl, aryl, heteroaryl, hydroxy protecting group, or a functional group which increases the water solubility of the taxane derivative, X$_7$ is alkyl, alkenyl, alkynyl, aryl, heteroaryl, or sulfhydryl protecting group;

X$_8$ is hydrogen, alkyl, alkenyl, alkynyl, aryl, or heteroaryl;

X$_9$ is an amino protecting group;

X$_{10}$ is alkyl, alkenyl, alkynyl, aryl, or heteroaryl;

X$_{11}$ is alkyl, alkenyl, alkynyl, aryl, heteroaryl, —OX$_{10}$, or —NX$_8$X$_{14}$;

X$_{14}$ is hydrogen, alkyl, alkenyl, alkynyl, aryl, or heteroaryl; and

M comprises ammonium or is a metal.

2. An intermediate for use in the preparation of taxol or other tricyclic or tetracyclic taxanes selected from the group consisting of

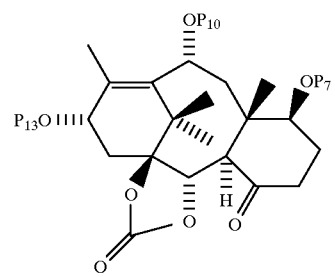

18

-continued

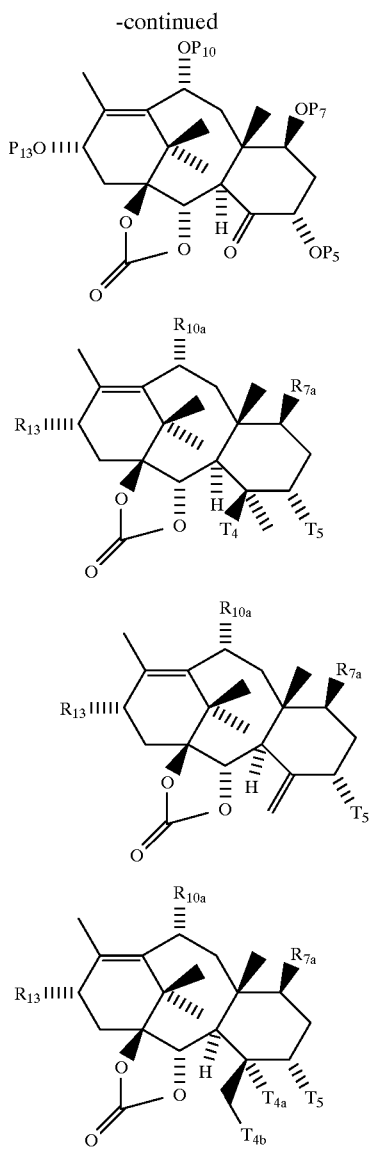

wherein
$T_4$ is hydroxy or protected hydroxy;
$T_{4a}$ and $T_{4b}$ are independently alkoxy, alkoxycarbonyloxy, acyloxy, sulfonyloxy, hydroxy, or protected hydroxy, or together form a carbonate;
$T_5$ is alkoxy, alkoxycarbonyloxy, acyloxy, sulfonyloxy, hydroxy, or protected hydroxy;
$P_5$, $P_7$, $P_{10}$ and $P_{13}$ are each a hydroxy protecting group;
$R_{7a}$ is hydrogen, halogen, protected hydroxy, or —$OR_{28}$;
$R_{10a}$ is hydrogen, —$OCOR_{29}$, hydroxy, or protected hydroxy;
$R_{13}$ is hydroxy, protected hydroxy, MO- or

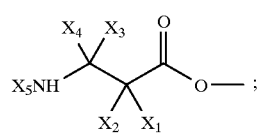

$R_{28}$ is hydrogen, acyl, hydroxy protecting group or a functional group which increases the solubility of the taxane derivative;

$R_{29}$ and $R_{30}$ are independently hydrogen, alkyl, alkenyl, alkynyl, monocyclic aryl or monocyclic heteroaryl;
$X_1$ is —$OX_6$, —$SX_7$, —$NX_8X_9$;
$X_2$ is hydrogen, alkyl, alkenyl, alkynyl, aryl, or heteroaryl;
$X_3$ and $X_4$ are independently hydrogen, alkyl, alkenyl, alkynyl, aryl, or heteroaryl;
$X_5$ is —$COX_{10}$, —$COOX_{10}$, —$COSX_{10}$, —$CONX_8X_{10}$, or —$SO_2X_{11}$;
$X_6$ is hydrogen, alkyl, alkenyl, alkynyl, aryl, heteroaryl, hydroxy protecting group, or a functional group which increases the water solubility of the taxane derivative;
$X_7$ is alkyl, alkenyl, alkynyl, aryl, heteroaryl, or sulfhydryl protecting group;
$X_8$ is hydrogen, alkyl, alkenyl, alkynyl, aryl, heteroaryl, or heterosubstituted alkyl, alkenyl, alkynyl, aryl or heteroaryl;
$X_9$ is an amino protecting group;
$X_{10}$ is alkyl, alkenyl, alkynyl, aryl, heteroaryl, or heterosubatituted alkyl, alkenyl alkynyl, aryl or heteroaryl;
$X_{11}$ is alkyl, alkenyl, alkynyl, aryl, heteroaryl, —$OX_{10}$, or —$NX_8X_{14}$;
$X_{14}$ is hydrogen, alkyl, alkenyl, alkynyl, aryl, or heteroaryl; and
M comprises ammonium or is a metal.

3. An intermediate for use in the preparation of a taxane having the formula;

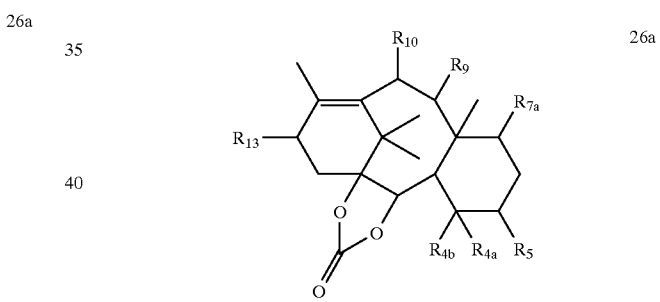

wherein
$R_{4a}$ is hydrogen, alkyl, hydroxy, protected hydroxy, or —$OCOR_{27}$, or together with $R_{4b}$ is an oxo;
$R_{4b}$ is hydrogen, alkyl, alkenyl, alkynyl, aryl, heteroaryl, or cyano, or together with $R_{4a}$ is an oxo;
$R_5$ is hydrogen, hydroxy, protected hydroxy, —$OCOR_{37}$, or oxo;
$R_{7a}$ is hydrogen, halogen, hydroxy, protected hydroxy, —$OR_{28}$, or —$OCOR_{34}$, or together with $R_9$ is a carbonate;
$R_9$ is hydrogen, oxo, hydroxy, protected hydroxy, —$OR_{28}$, or —$OCOR_{33}$, or together with $R_{7a}$ or $R_{10}$ is a carbonate;
$R_{10}$ is hydrogen, oxo, hydroxy, protected hydroxy, —$OR_{28}$, or —$OCOR_{29}$, or together with $R_9$ is a carbonate;
$R_{13}$ is hydrogen, hydroxy, protected hydroxy, —$OCOR_{35}$, MO- or

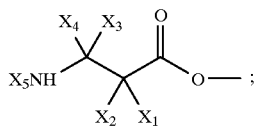

$R_{28}$ is a functional group which increases the solubility of the taxane derivative;

$R_{27}$, $R_{29}$, $R_{33}$, $R_{34}$, $R_{35}$, and $R_{37}$ are independently hydrogen, alkyl, alkenyl, alkynyl, alkoxy, aryloxy, —$NX_8X_{10}$, —$SX_{10}$, monocyclic aryl or monocyclic heteroaryl;

$X_1$ is —$OX_6$, —$SX_7$, or —$NX_8X_9$;

$X_2$ is hydrogen, alkyl, alkenyl, alkynyl, aryl, or heteroaryl;

$X_3$ and $X_4$ are independently hydrogen, alkyl, alkenyl, alkynyl, aryl, or heteroaryl;

$X_5$ is —$COX_{10}$, —$COOX_{10}$, —$COSX_{10}$, —$CONX_8X_{10}$, or —$SO_2X_{11}$;

$X_6$ is hydrogen, alkyl, alkenyl, alkynyl, aryl, heteroaryl, hydroxy protecting group, or a functional group which increases the water solubility of the taxane derivative;

$X_7$ is alkyl, alkenyl, alkynyl, aryl, heteroaryl, or sulfhydryl protecting group;

$X_8$ is hydrogen, alkyl, alkenyl, alkynyl, aryl, or heteroaryl;

$X_9$ is an amino protecting group;

$X_{10}$ is alkyl, alkenyl, alkynyl, aryl, or heteroaryl;

$X_{11}$ is alkyl, alkenyl, alkynyl, aryl, heteroaryl, —$OX_{10}$, or —$NX_8X_{14}$;

$X_{14}$ is hydrogen, alkyl, alkenyl, alkynyl, aryl, or heteroaryl; and

M comprises ammonium or is a metal.

4. The intermediate of claim 3 wherein $R_{4a}$ is hydrogen, alkyl, hydroxy, protected hydroxy, or together with $R_{4b}$ is an oxo; and $R_{4b}$ is hydrogen, alkyl, or together with $R_{4a}$ is an oxo.

5. The intermediate of claim 3 wherein $R_5$ is hydrogen, hydroxy or protected hydroxy.

6. The intermediate of claim 3 wherein $R_{7a}$ is hydroxy or protected hydroxy.

7. The intermediate of claim 3 wherein $R_9$ is hydrogen or oxo.

8. The intermediate of claim 3 wherein $R_9$ is hydrogen.

9. The intermediate of claim 3 wherein $R_{13}$ is hydroxy or protected hydroxy.

10. The intermediate of claim 3 wherein $R_{4a}$ is hydrogen, alkyl, hydroxy, protected hydroxy, or together with $R_{4b}$ is an oxo;

$R_{4b}$ is hydrogen, alkyl, or together with $R_{4a}$ is an oxo;

$R_5$ is hydrogen, hydroxy or protected hydroxy;

$R_{7a}$ is hydroxy or protected hydroxy;

$R_9$ is hydrogen; and $R_{10}$ is hydroxy or protected hydroxy.

11. The intermediate of claim 3 wherein $R_{4a}$ together with $R_{4b}$ is an oxo;

$R_5$ is hydrogen;

$R_{7a}$ is hydroxy or protected hydroxy;

$R_9$ is hydrogen;

$R_{10}$ is hydroxy or protected hydroxy; and $R_{13}$ is hydroxy or protected hydroxy.

12. The intermediate of claim 3 wherein $R_{4a}$ together with $R_{4b}$ is an oxo;

$R_5$ is hydroxy or protected hydroxy;

$R_{7a}$ is hydroxy or protected hydroxy;

$R_9$ is hydrogen;

$R_{10}$ is hydroxy or protected hydroxy; and $R_{13}$ is hydroxy or protected hydroxy.

13. The intermediate of claim 3 wherein $R_{4a}$ is hydroxy or protected hydroxy;

$R_{4b}$ is alkyl;

$R_5$ is hydroxy or protected hydroxy;

$R_{7a}$ is hydroxy or protected hydroxy;

$R_9$ is hydrogen;

$R_{10}$ is hydroxy or protected hydroxy; and $R_{13}$ is hydroxy or protected hydroxy.

14. The intermediate of claim 3 wherein $R_{4a}$ is alkyl;

$R_{4b}$ is alkyl;

$R_5$ is hydroxy or protected hydroxy;

$R_{7a}$ is hydroxy or protected hydroxy;

$R_9$ is hydrogen;

$R_{10}$ is hydroxy or protected hydroxy; and $R_{13}$ is hydroxy or protected hydroxy.

15. The intermediate of claim 3 wherein $R_{13}$ is

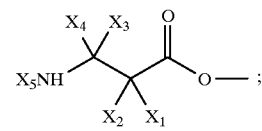

$X_1$ ia —$OX_6$;

$X_2$ is hydrogen or alkyl;

$X_6$ is hydrogen or hydroxy protecting group; and $X_3$, $X_4$ and $X_5$ are as defined in claim 3.

16. The intermediate of claim 10 wherein $R_5$ is trimethylsilyloxy;

$R_{7a}$ is 2-methoxy-2-propyloxy or benzyloxymethyloxy;

$R_{10}$ is triethylsilyloxy; and $R_{13}$ is (dimethyl,tert-butyl)-silyloxy.

* * * * *

UNITED STATES PATENT AND TRADEMARK OFFICE
CERTIFICATE OF CORRECTION

PATENT NO. : 6,005,120
DATED : December 21, 1999
INVENTOR(S) : Robert A. Holton et al.

It is certified that error appears in the above-identified patent and that said Letters Patent is hereby corrected as shown below:

Column 1,
Lines 40-48, the chemical structure should read:

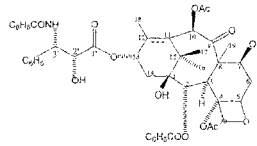

Column 5,
Lines 15-23, the chemical structure should read:

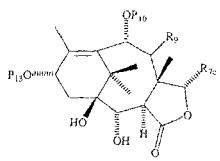

Column 10,
Line 14, "R36" should read -- $R_{36}$ --.

Column 15,
Lines 52-63, structure 26a should read:

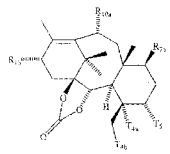

Column 28,
Structure 37, that portion reading "Baccatin IIIII" should read -- Baccatin III --.

Column 42,
Chemical structure 14 should read:

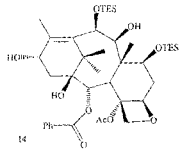

Column 50,
Between chemical structures 26 and 27 should read:

$$\xrightarrow{\underset{DMAP}{Ac_2O}}$$

The last recited structure should read:

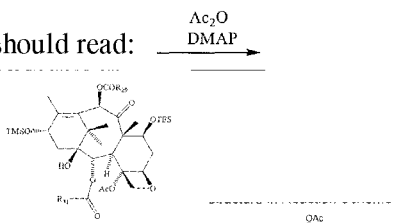

Column 55,
The second structure in Reaction Scheme 13 should read:

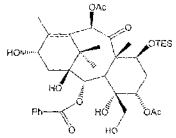

UNITED STATES PATENT AND TRADEMARK OFFICE
CERTIFICATE OF CORRECTION

PATENT NO. : 6,005,120
DATED : December 21, 1999
INVENTOR(S) : Robert A. Holton et al.

It is certified that error appears in the above-identified patent and that said Letters Patent is hereby corrected as shown below:

Column 85,
Line 64, should read -- with $R_{4b}$ or $R_5$ is carbonate; --

Column 86,
Line 2, "$R_{40}$" should read -- $R_{4a}$ --.
Line 29, "-$OX_5$," should read -- -$OX_6$, --.

Column 87,
Line 65, "hydrogeri," should read -- hydrogen, --.

Column 88,
Line 24, "subatituted" should read -- substituted --.
Line 32, "formula;" should read -- formula: --.

Column 90,
Line 48, "ia" should read -- is --.

Signed and Sealed this

Seventeenth Day of August, 2004

JON W. DUDAS
*Acting Director of the United States Patent and Trademark Office*